United States Patent [19]
De Lencastre et al.

[11] Patent Number: 6,030,807
[45] Date of Patent: Feb. 29, 2000

[54] HIGHLY REGULABLE PROMOTER FOR HETEROLOGOUS GENE EXPRESSION

[75] Inventors: Herminia De Lencastre, New York, N.Y.; Isabel De Sá-Nogueira, Oeiras, Portugal

[73] Assignee: The Rockefeller University, New York, N.Y.

[21] Appl. No.: 08/926,842

[22] Filed: Sep. 10, 1997

Related U.S. Application Data

[60] Provisional application No. 60/031,077, Sep. 10, 1996.

[51] Int. Cl.[7] .......................... C12N 15/11; C12N 15/75; C12N 1/21; C12N 15/67
[52] U.S. Cl. .................. 435/69.1; 435/252.3; 435/320.1; 435/471; 536/24.1; 536/24.32
[58] Field of Search ............................... 536/24.1, 24.32; 435/320.1, 252.3, 69.1, 471

[56] References Cited

FOREIGN PATENT DOCUMENTS

WO 86/04356   7/1986   WIPO.

OTHER PUBLICATIONS

Reeck et al., Cell 50:667 (1987).
George et al., "Current methods in sequence comparison and analysis," in *Macromolecular Sequencing and Synthesis, Selected methods and Applications,* 1988, D.H. Schlesinger (ed.), Alan R. Liss, Inc. New York, NY, pp. 127–149.
Boswell et al., "Sequence comparison and alignment: the measurement and interpretation of sequence similarity," in *Computational Molecular Biology: Sources and Methods for Sequence Analysis,* 1988, Arthur M. Lesk (ed.), Oxford University Press, New York, NY, pp. 161–178.
Brakhage et al. (1997) EMBL Seq. Database: Z75208.
Brown et al. (1972) J. Bact. 111:606–13.
Brunell et al. (1989) J. Mol. Biol. 209:607–22.
Chambliss (1993) In: B. subtilis and other gram–positive bacteria: biochem., physiol., mol. gen., Am. Soc. Microbiol., DC, pp.:213–219.
Dassa et al. (1985) EMBO J. 4:2287–93.
Deutscher et al. (1995) Mol. Microbiol. 15:1049–53.
Deutscher et al. (1994) J. Bacteriol. 176:3336–44.
Englesberg et al. (1969) Proc. Natl. Acad. Sci. USA 69:1100–7.
Fisher et al. (1994) J. Bacteriol. 176:1903–12.
Fujita et al. (1987) Proc. Natl. Acad. Sci. 84:4524–8.
Gartner et al. (1992) Mol. Gen. Genet. 232:415–22.
Henkin et al. (1990) Mol. Microbiol. 5:575–84.
Higgins et al. (1990) J. Bioenerg. Biomemb. 22:571–92.
Horazdowvsky et al. (1989) J. Bact. 171:3053–9.
Hueck et al. (1995) Mol. Microbiol. 15:395–401.
Kaji et al. (1975) Biochim. Biophys. Acta. 410:354–60.
Kolodrubetz et al. (1981) J. Bact. 148:472–9.
Miwa et al. (1988) J. Biol. Chem. 263:13252–7.
Moran et al. (1993) In: B. subtilis and other gram–positive bacteria: biochem., physiol., mol. gen., Am. Soc. Microbiol., DC, pp. 653–667.
Novotny et al. (1996) Biochim. Biophys. Acta. 117:217–30.
Ogden et al. (1980) Natl. Acad. Sci. USA 77:3346–50.
Paveia et al. (1992) Broteria Genetica XIII(LXXX):149–59.
Paveia et al. (1992) Broteria Genetica XIII(LXXX):161–7.
Saier et al. (1996) Microbiol. 142:217–30.
Sa–Noguiera et al. (1997) Microbiol. 143:957–69.
Sa–Noguiera et al. (1989) J. Bacteriol. 171:4088–91.
Sa–Noguiera et al. (1988) J. Bacteriol. 170:2855–7.
Saurin et al. (1994) Mol. Microbiol. 12:993–1004.
Tam et al. (1993) Microbiol. Rev. 57:320–46.
Weickert et al. (1990) Proc. Natl. Acad. Sci. 87:6238–42.
Weinstein et al. (1979) Physiol. 63:425–32.

*Primary Examiner*—Johnny F. Railey, II
*Attorney, Agent, or Firm*—Klauber & Jackson

[57] ABSTRACT

The invention relates to an operon encoding enzymes involved in the utilization of L-arabinose, to the promoter derived therefrom, and to expression systems utilizing the promoter. The promoter is particularly useful for expression of DNA sequences in prokaryotes because of their inducibility and repressibility of the promoter. The invention also relates to the enzymes of the operon, and antibodies thereto.

22 Claims, 28 Drawing Sheets

```
                                                                                                                       -35
                                                                                      >>>>>>>>>>>>>>>>>>>>>>>>>>>>>>>>>>>>>
  1 AAGCTTCTCATCAATGATTTGAATTGAGCTGGGCTGGCGTCGGCCTTATTGAATTAAAAAGCCGGCTCGCCCCGGCTTTTTTAAAAGAAAAGATTGAC
                                     -10       +1                          >>    IR <<<<<<<<
101 AGTATAATAGTCAATTACTATAATAAAATTGTTCGTACAAATATTTATTTATAGTTTATTTTCTATCATTAGTGTATCTTTGTATTTGAAAGGTT
    > IR <  <<<<<
    >>>  >>>>>  >IR<  <<<<<  <<<
            rbs         araA- M  L  Q  T  K  D  Y  E  F  W  F  V  T  G  S  Q  H  L  Y  G  E  E  T  L  E
                             *****PrimerA******
201 TTATTTATGAGAGAAGGGCAGTTACAATGCTTCAGACAAAGGATTATGAATTCTGGTTTGTGACAGGAAGCCAGCACCTATACGGGGAAGAGACCCTGG
                                                                                     *****PrimerB*** ***
    L  V  D  Q  H  A  K  S  I  C  E  G  L  S  G  I  S  S  R  Y  K  I  T  H  K  P  V  V  T  S  P  E  T
301 AACTCGTAGATCAGCATGCTAAAAGCATTTGTGAGGGCTTCAGCGGGATTTCTTCCAGATATAAAATCACTCATAAGCCCGTCACTTCACCGGAAAC I  R  E  L  L  R  E  A  E  Y  S  E  T  C  A  G  I  I  T  W  M  H  T  F  S  P  A  K  M  W  I  E  G
401 CATTCGAGAGCTGTTAAGAGAGGCGGAGTACAGTGAGACATGTGCTGGCATCATTACATGGATGCACACATTTCCCGCCAAAATGTGGATAGAAGGC
                                                                       araA'-lacZ fusion
    L  S  S  Y  Q  K  P  L  M  H  L  H  T  Q  Y  N  R  D  I  P  W  G  T  I  D  M  D  F  M  N  S  N  Q  S
501 CTTTCCTCTTATCAAAAACCGCTTATGCATTTGCATACACAATATAATCGCATACCGCGGGTACGATTGACATTGATGACTTTATGAACAGCAACCAAT A  H  G  D  R  E  Y  G  Y  I  N  S  R  M  G  L  S  R  K  V  I  A  G  Y  W  D  D  E  E  V  K  K  E
601 CCGGGCATGGCGATCGAGAGTACGGTTACATCGAGAATGGGCTTAGCCGTAAAAGTCATTGCCGGCTATTGGGATGATGAAGAAGTGAAAAAAGA M  S  Q  W  M  D  T  A  A  A  L  N  E  S  R  H  I  K  V  A  R  F  G  D  N  M  R  H  V  A  V  T  D
701 AATGTCCCAGTGGATGGATACGGCCGCCGCTCTGAATGAAAGCAGACATATTAAGGTTGCCAGATTTGGAGATAACATGCGGCATGTCGCGGTAACGGAC
```

FIG.2A-1

```
       G  D  K  V  G  A  H  I  Q  F  G  W  Q  V  D  G  Y  G  I  G  D  L  V  E  V  M  D  R  I  T  D  D  E  V
 801 GGAGACAAGGTGGAGCGCATATTCAATTGGCTGGCAGGTTGACGGATCTGTTGAAGTAGATGGATACGGAGACGAGG

D  T  L  Y  A  E  Y  D  R  L  Y  V  I  S  E  E  T  K  R  D  E  A  K  V  A  S  I  K  E  Q  A  K  I
 901 TTGACACGCTTTATGCCGAGTATGACAGACTATATGTCATCAGTGAGGAAACAAAACGTGACGAAGCAAAGGTAGCGTCCATTAAAGAACAGGCGAAAT

E  L  G  L  T  A  F  L  E  Q  G  G  Y  T  A  F  T  T  S  F  E  V  L  H  G  M  K  Q  L  P  Q  L  A
1001 TGAACTTGGATTAACCGCTTTTCTTGAGCAAGGCGGATACACAGCGTTTACGACATGTTCGTTGAAGTGCTGCACGGAATGAAACAGCTGCCGGACTTGCC

V  Q  R  L  M  E  K  G  Y  G  F  A  G  E  G  D  W  K  T  A  A  L  V  R  M  M  K  I  M  A  K  G  K  R
1101 GTTCAGCGCCTGATGGAGAAAGGCTATGGGTTCGCCGGTGAAGGAGACTGGAAGACAGCGGCGCTTGTACGGATGATGAAAATCATGGCTAAAGGAAAA

T  S  F  M  E  D  Y  T  Y  H  F  E  P  G  N  E  M  I  L  G  S  H  M  L  E  V  C  P  T  V  A  L  D
1201 GAACTTCCTTCATGGAAGATTACACGTACCATTTTGAACCGGGAAATGAATTCTGGCCTCTCACATGCTTGAAGTGTGTCCGACTGTCGCTTGGA

Q  P  K  I  E  V  H  S  L  S  I  G  G  K  E  D  P  A  R  L  V  F  N  G  I  S  G  S  A  I  Q  A  S
1301 TCAGCCCGAAAATCGAGGTTCATTCGATTGGCGGCAAAGAGGACCCTGCCGCGTTTGGTATTTAACGGCATCAGCGGTTCTGCCATTCAAGCTAGC

I  V  D  I  G  G  R  F  R  L  V  L  N  E  V  N  G  Q  E  I  E  K  D  M  P  N  L  P  V  A  R  V  L  W
1401 ATTGTTGATATTGGGGGCCGGTTCCGCTGCTCGAATGAAGTCAACGGCCAGGAAATTGAAAAAGACATGCCGAATTTACCGGTTGCCCGTGTTCTCT

K  P  E  P  S  L  K  T  A  A  E  A  W  I  L  A  G  G  A  H  H  T  C  L  S  Y  E  L  T  A  E  Q  M
1501 GGAAGCCCGAGCCGTCATTGAAAAACAGCCGCAGAGCATGGATTTAGCCGGCGGCGCACCATACCTGCCTGTCTTATGAACTGACAGCGGAGCAAAT
```

FIG.2A-2

```
            L  D  W  A  E  M  A  G  I  E  S  V  L  I  S  R  D  T  T  I  H  K  L  K  H  E  L  K  W  N  E  A  L
1601 GCTTGATTGGGCGGAAATGGCGGGAATCGAAAGTGTTCTCATTTCCGTGATACGAAACGAGTTAAAATGAAACGAGGCGCTT

Y  R  L  Q  K  *   rbs    araB- M  A  Y  T  I  G  V  D  F  G  T  L  S  G  R  A  V  L  V  H  V  Q  T
1701 TACCGGCTTCAAAAGTAGACGGGATGTCACATGGCTTACACAATAGGGTTGATTTTGAACTTATCAGGAGCAGTCGTTCATGTCCAAACA G  E  E  L  A  A  A  V  K  E  Y  R  H  A  V  I  D  T  V  L  P  K  T  G  Q  K  L  P  R  D  W  A  L  Q
1801 GGGGAGGAACTTGCGGCTGCTGTAAAAGAATACCGGCATGCTGTCATTGATACGGTCCTTCCAAAACGGGTCAAAAGCTGCCGCGTGACTGGGCGCTGC >>>>  >>>    IR    <<<  <<
       H  P  A  D  Y  L  E  V  L  E  T  T  I  P  S  L  L  E  Q  T  G  V  D  P  K  D  I  I  G  I  D
1901 AGCACCCTGCTGATTACCTGGAAGTCTTGGAAACAACCATTCCGTCTTTACTGGAACAGACGGGCGTTGACCCGAAAGACATTATCGGATTGAATTGA
       <<<

F  T  A  C  T  I  L  P  I  D  S  S  G  Q  P  L  C  M  L  P  E  Y  E  E  E  P  H  S  Y  V  K  L  W
2001 TTTCACGGCATGTACGATCCTTCCTATTGACAGCAGCGGCCAGCCGCTGTGCATGCTGCCAGAATATGAAGAGGAGCCCCACAGCTATGTGAAGCTCTGG
```

FIG.2A-3

```
       K  H  H  A  A  Q  K  H  A  D  R  L  N  Q  I  A  E  E  E  G  E  A  F  L  Q  R  Y  G  G  K  I  S  S  E
2101 AAGCATCATGCGGCCCAAAAACATGCTGATCGGCTCAATCAATCCGGAAGAAGAAGGAGGAGCCTTTTTACAGCGGTACGGAGGAAAAATTCATCAG

W  M  I  P  K  V  M  Q  I  A  E  E  A  P  H  I  Y  E  A  A  D  R  I  I  E  A  A  D  W  I  V  Y  Q
2201 AATGGATGATTCCAAAGGTCATGCAGATAGCTGAAGAAGCCCTCACATTTATGAGGCTGCAGACCGGATCATCGAGGCTGCGGACTGGATCGTGTACCA

L  C  G  S  L  K  R  S  N  C  T  A  G  Y  K  A  M  W  S  E  K  A  G  Y  P  S  D  D  F  F  E  K  L
2301 GCTGTGCGGCTCCCTGAAGCGAAGCAATTGTACCGCAGGTTATAAAGCGATGTGGAGTGAAAAAGCCGGATATCCGTCAGATGATTCTTTGAGAATTA

N  P  S  M  K  T  I  T  K  D  K  L  S  G  S  I  H  S  V  G  E  K  A  G  S  L  T  E  K  M  A  K  L  T
2401 AATCCTTCAATGAAAACGATTACAAAGGACAAATTGTCAGGTTCATTCATTCAGTAGGAGAAAAAGCCGGCAGTCTGACTGAAAAATGCAAAGCTGA

G  L  L  P  G  T  A  V  A  V  A  N  V  D  A  H  V  S  V  P  A  V  G  I  T  E  P  G  K  M  L  M  I
2501 CAGGGCTTCTCCCGGAACGGCTGTTGCGGTTGCCAATGTCGACGCTCATGTTTCGTACCGGCGTCCCATTACGAGCCAGGAAAATGCTGATGAT

M  G  T  S  T  C  H  V  L  L  G  E  E  V  H  I  V  P  G  M  C  G  V  V  D  N  G  I  L  P  G  Y  A
2601 TATGGAACCTCGACGTGCCATGTCTACTTGGTGAAGAGGTCCATATCGTTCCAGGAATGTGCGGCGTTGTGGACAACGGCATTCTCCCGGCTATGCG

G  Y  E  A  G  Q  S  C  V  G  D  H  F  D  W  F  V  K  T  C  V  P  P  A  Y  Q  E  E  A  K  E  K  N  I
2701 GGATATGAAGCCGGCCAGTCCTGTGTCGGGGATCATTTCGATTGGTTTGTGAAAACATGTGTCCCGCCAGCTTATCAAGAAGAAGCAAAGGAAAAAAACA
```

FIG.2B-1

```
         G V H E L L S E K A N H Q A P G E S G L L A L D W W N G N R S T L
2801 TTGGGTTCATGAGCTGCTGAGTGAGAAAGCAAACCATCAGGCCCTGGTGAAGGGCCTTGCTGCTTGATGTGGAATGGTAACCGTTCAACTCT

V D A D L T G M L L G M T L L T K P E E I Y R A L V E A T A Y G T
2901 TGTTGATGCAGATTTAACAGGATGCTGCTTGGCATGACACTGCTTGACCAAGCCTGAGGAGATTTATAGAGCGTTAGTTGAAGCGACAGCTTACGGAACC

R M I I E T F K E S G V P I E E L F A A G G I A E K N P F V M Q I Y
3001 CGGATGATTATCGAAACATTCAAAGAAAGCGGTGTTCCGATTGAAGAACTGTTCGCAGCGGGGATAGCTGAGAAAAACCCGTTTGTCATGCAGATTT

A D V T N M D I K I S G S P Q A P A L G S A I F G A L A A G K E K
3101 ATGCGGATGTGACAAACATGGACATTAAAATCTCGGTTCACCGCAGCCTAGGATCTGCCATTTTCGGCGCCTTGGCAGCAGGCAAAGAAAA araAB'-lacZ fusion
         G G Y D D↓I K K A A A N M G K L K D I T Y T P N A E N A A V Y E K
3201 AGGCGGCTACGATGATATCAAAAAGGCAGCGGCGAACATGGGAAAACTGAAAGATATAACTTATACGCCGAAAATGCCGAAAATGCCGTTTATGAAAA L Y A E Y K E L V H Y F G K E N H V M K R L K T I K N L Q F S S A A
3301 TTGTACGCCGAATATAAAGAGCTGGTTCATTATTTCGGAAAGAAAATGATCAAAAATCTCAATTTTCAATCGCCG K K N * * rbs  araD - M L E T L K K E V L A A N L K L Q E H Q L V T F
3401 CCAAAAAGAATTGATTAAAGGTGATGGAGCATGTTGAAACATTAAAAAAGAAGTGCTGGCCGCAACCTGAAGCTTCAAGCTTCAAGAGCATCACCTGTAACCT
```

FIG.2B-2

```
        T  W  G  N  V  S  G  I  D  R  E  K  E  R  I  V  I  K  L  A  E  S  N  T  S  D  L  T  A  D  D  L  V
3501 TTACGTGGGGAATGTCAGCGGCATTGACCGTGAAAAGAATTGTCATCAAACTAGCGGAGTCGAATACCAGCCGATGACCGATGACTTGT

V  L  N  L  D  G  E  V  V  E  G  S  L  K  P  S  S  D  T  P  T  H  V  Y  L  Y  K  A  F  P  N  I  G
3601 TGTTTTGAACCTTGATGGCGAGAGGTCGTCGAGAGTCTCGCTTAAACCTTCCAGATACCACTACCATGTTTATCTATAAAGCTTTCCGAATATCGGG

G  I  V  H  T  H  S  Q  W  A  T  S  W  A  Q  S  G  D  R  I  P  P  L  G  T  T  H  A  D  Y  F  D  S  A
3701 GGAATTGTCCATACCCATTCTCAATGGGCCACAAGCTGGGCCAAAGCGGCGACATCCCGTTAGGCACGACCCATGCTGATTATTTTGACAGTG

I  P  C  T  R  E  M  Y  D  E  E  I  I  H  D  Y  E  L  N  T  G  K  V  I  A  E  T  F  Q  H  H  N  Y
3801 CGATTCCATGTACTCGAGAAATGTACGATGAGGAAATCATTCATGACTACGAACTGAATACAGGAAAAGTCATAGCGGAAACTTTCCAGCATCATAATTA

E  Q  V  P  G  V  L  V  N  N  H  G  P  F  C  W  G  T  D  A  L  N  A  I  H  N  A  V  V  L  E  T  V
3901 CGAACAGGTGCCGGGTGTCCTCGTGAATAATCACGGACCGTTCTGCTGGGGCACTGACGCCTTAAATGCCATTCATAACGCAGTTGTATTAGAAACGGTT
                                                                                                  rbs
        A  E  M  A  Y  H  S  I  M  L  N  K  D  V  T  P  I  N  T  V  L  H  E  K  H  F  Y  R  K  H  G  A  N  A
4001 GCCGAAATGGCCTATCACTCCATTATGCTGAACAAGGATGTGACGCCAATCAATACAGTCCTGCATGAAAAGCATTTTTATCGAAAACACGGAGCAAATG
                                                                                                          >
     araL  M  A  S  H  D  T  P  V  S  P  A  G  I  L  I  D  L  D  G  T  V  F  R  G  N  E  L  I  E  G  A  R
4101 CGTATTATGGCCAGTCAGTCATGATACGCCTGTGTCACCGGCTGGCATTCGATGACTGACGGTACTGTATTCAGAGGAAATGAGTTGATCGAAGGAGCAA
        Y  Y  G  Q  S  *
     >>>>> >>> IR <<< <<<<<
```

```
      E  A  I  K  T  L  R  R  M  G  K  K  I  V  F  L  S  N  R  G  N  I  S  R  A  M  C  R  K  K  L  L  G
4201  GAGAAGCGATCAAAACGTTAGGAGAATGGGAAAGAAAATCGTCTTTTTAAGCAACGGGGAATATCCCGTCCATGTGCCGTCAGAAAAACTTCTTGG
      A  G  I  E  T  D  V  N  D  I  V  L  S  S  S  V  T  A  A  F  L  K  K  H  Y  R  F  S  K  V  W  V  L
4301  GCCGGGGATTGAAACGGACGTAAACGACATTGTTCTGTCATCAAGCGTCACAGCGGCTTTCTGAAAAAACATTATCGTTTTCAAAGGTATGGGTGCTT
      G  E  Q  G  L  V  D  E  L  R  L  A  G  V  Q  N  A  S  E  P  K  E  A  D  W  L  V  I  S  L  H  E  T  L
4401  GGGGAGCAAGGCTTGGTTGACGAGCTGAGGCTGGCCGGTGTGCAGAACGCGAGCGAACCGAAGGAAGCGGATTGGCTTGTGATCTCCCTTCATGAAACGC
      T  Y  D  D  L  N  Q  A  F  Q  A  A  A  A  G  G  A  R  I  I  A  T  N  K  D  R  S  F  P  N  E  D  G  N
4501  TCAGTACGACGATTTAAATCAAGCCTTTCAGGCTGCCGCCGCGGGCGCGGCGCTCGTATAATCGCTACAACAAAGACCGTCTTTTCCGAACGAAGACGGAAA
      A  I  D  V  A  G  M  I  G  A  I  E  T  S  A  Q  K  T  E  L  V  V  G  K  P  S  W  L  M  A  E  A
4601  TGCCATTGATGTGGCCGGAATGATCGGGGCCATTGAGACTTCTGCACAAGCGAAGACTGAACTGGTCGTCGGAAAACGTCATGGCTGATGGCGGAGGCT
      A  C  T  A  M  G  L  S  A  H  E  C  M  I  I  G  D  S  I  E  S  D  I  A  M  G  K  L  Y  G  M  K  S  A
4701  GCCTGCACGGCAATGGGCCTGTCCGCACATGAATGCATGATTATAGGAGACAGCATTGAATCTGACATTGCAATGGGAAGCTTATGGCATGAAAAGCG
      L  V  L  T  G  S  A  K  Q  G  E  Q  R  L  Y  T  P  D  Y  V  L  D  S  I  K  D  V  T  K  L  A  E  E
4801  CCTTAGTGCTAACTGGTTCTGCCAAACAGGGAGAACAGGTGAACGCGGTTTGTACACCGGATTATGTGCTGGATTCTATTAAGGATGTAACCAAATTGGCTGAAGAA
      rbs  araM- M  N  R  I  A  A  D  V  Q  R  A  F  E  N  A  G  E  K  T  L  P  I  K  V  E  E  I  V  L  G
      G  I  L  I  *
4901  GGGATTCTTGATATGAATCGTATCGCCGCTGACGTTCAGCGTGCTTTCGAAAACGCCGAGAAAGACGTTGCCTATAAAGTTGAAGAAATTGTTCTCG
```

```
     K  Q  A  A  D  S  L  L  D  Y  V  K  R  K  N  N  Q  H  I  V  L  V  C  D  A  N  T  H  R  I  A  G  I
5001 GTAAGCAAGCAGCTGATTGCTTGTTTGATTATGTAAAACAATCAACATATGTCCTTGTCGACGGAATACACCCATTCCAGAAT

D  L  E  N  R  L  N  Q  E  G  F  Q  A  E  C  L  I  I  P  E  N  E  A  G  D  V  T  A  D  E  R  S  L
5101 TGATTAGAAAACGACTGAATCAAGAAGGATTTCAGGCCGAGTGCTGATCATTCCAGAAAATGAGCCGGAGATGTGACAGCTGATGAACGATGCTC

I  H  V  L  I  H  T  K  Q  P  T  D  V  M  I  A  V  G  S  G  T  I  H  D  I  V  R  F  A  A  F  Q  R  D
5201 ATTCATGTCCTGATCCATACGAAACAACCGACTGATGTCATGATTGCGGCACGATCATGATATCGTCCGCTTTGCGGCTTTCAAAGAG

L  P  F  I  S  Y  P  T  A  P  S  V  D  G  F  T  S  A  G  A  P  I  I  L  Y  G  T  K  T  T  I  Q  T
5301 ATTTGCCGTTATTCTTATCCTACTGCTCCATCTGTAGACGGTTTTACATCAGCCGGTGCCGATTATTTATACGGCACAAAACAACCATTCAAAC

K  A  P  S  A  L  F  A  D  L  D  L  L  K  A  A  P  Q  S  M  V  A  A  G  F  G  D  M  L  G  K  I  T
5401 GAAGCCCCATCTGCCCTGTTCGCTGACCTGGATCTATTAAAAGCGGCACCCCAGTCAATGGTCGCTGCTGGATTTGGAGATATGCTGGTAAATCACG

S  L  A  D  W  E  I  S  R  H  L  A  G  E  P  Y  S  P  A  G  A  K  I  V  Q  E  A  L  A  A  C  I  E  H
5501 TCTTTAGCAGATTGGGAAATATCCGCATCATCTGCCGGGAGCCTTATCCGCCGGTGCTAAGATCGTTCAGGAGGCGCTAGCTGCCTGCATTGAAC

T  E  D  I  A  M  K  T  E  T  G  I  R  V  L  M  E  S  L  L  V  S  G  L  V  M  L  A  L  D  H  S  R
5601 ACACAGAAGACATTGCCATGAAAACGGAAACTGGCATACGGGTTTTGATGGAGTCTTTACTTGTATCGGGCTTGTCATGCTCGCTTTAGATCATTCCG

P  A  S  G  G  E  H  H  I  S  H  W  I  E  M  E  L  M  E  K  K  R  P  Q  I  L  H  G  A  K  V  G  C
5701 ACGGCATCAGGGGGCCAGCATCATATTCACATTGGATTGAAATGGAGTTAATGGAAAAAACGCCCTCAGATTCTTCATGGGGCAAAGGTGGGCTGT
```

FIG.2C-2

```
          A  A  V  L  L  T  D  T  Y  R  K  L  A  Q  D  D  G  L  N  E  F  S  P  S  R  R  E  A  I  Q  S  A  Y  Q
5801 GCCGCTGTTTTATTAACTGACACATAGAAAGCTCGCCAGATGACGGCCTGAACGATTTCACCAGCCGCCGGGAAGCCATCCAATCGGCTTATC

T  L  P  R  G  E  V  L  A  D  W  L  R  S  A  G  G  P  A  D  F  D  E  I  G  V  G  Q  D  S  V  K  N
5901 AAACACTCCCGAGAGGAGAAGTCTGCTGGATTGGCTGAGATCAGCCGGAGCCCCTGCTGATTTGACGAAATCGGTGGGCAGATTCGTCAAAAA

A  F  R  H  A  H  T  L  R  D  R  C  T  G  L  R  I  I  N  E  N  K  T  L  I  N  H  G  L  Y  E  *
6001 TGCCTTCAGACACGGCACGGCACACTTAAGAGACCGATGCACCGATTAAGAATCATCAATGAAAACAAAACTGATCAACCATGGTCTATATGAATAGCCC rbs         araN- M  K  K  M  T  V  C  F  L  V  L  M  M  L  L  T  L  V  I  A  G  C  S  A  E
6101 GCACCTCGAATGAAGGGTAACGCAGATAACGGCAGATGAAAAAAATGACTGTCTGTTTCTGGTCCTGATGATGCTGCTCACTAGTCATTGCCGGGTGTTCAGCAG
                                                                                                                       >>>>>>>   >>>>    >   IR
          K  S  S  G  K  S  G  E  T  E  L  T  F  W  T  F  N  G  L  H  E  Q  F  Y  V  E  M  V  K  E  W  N  K
6201 AAAAATCATCGGCAAATCGGGTGAAACTGAGCTGACCTTTTGGACATTGAACGGCTTCATGAGCAGTTCTATGTGGAAATGGTGAAGGAATGGAACAA K  Y  P  D  R  K  I  K  L  N  T  V  V  Y  P  Y  G  Q  M  H  D  N  L  S  I  S  L  I  A  G  E  G  V
6301 AAAATATCCTGACCGCAAAATTAAGCTGAATACTGTTGTCTATCCATATGGACAAATGCACGATAACTTATCTATCTCCCTAATAGCGGGAGAAGGCGTT
```

```
      E  L  K  E  K  N  K  Y  T  D  Y  F  Q  N  G  T  G  I  F  S  V  L  L  D  I  K  D  E  I  N  P  I  Y
7201  GGAATTGAAAGAGAAAACAAATACACGGATTACTTCCAAAACGGAACAGGCATTTTCTCGTCCGTCCTGCTGGATATCAAGGATGAAATCAATCCAATTTAT

L  H  E  D  F  A  K  A  S  D  L  V  N  R  S  V  L  F  D  A  L  K  S  Q  Q  K  T  P  K  Q  A  L  D  R
7301  TTACATGAGGATTTTGCCAAGCTTCAGAGACCTGTGCGCGGTATTGTCAACAGAGAGGTATTGTCAACAGAGAGGTCGACGCGGTATTGTCAACAGAGAGGTCGACA rbs   araP- M  K  P  V  K  T  G  T  V  H  P  V
7401  GAGCGGCAGGTGACTGAACTGAAACAATAGAATCAAAAAGTGAAGTTCTCATGAAACTGTGAAAACGGGAAACGGTTCATCCGTT
      A  A  G  E  L  K  Q  K  *

P  S  A  A  K  Q  S  G  W  R  D  L  F  Y  S  K  K  A  A  P  Y  L  F  T  A  P  F  V  L  S  F  L  V  F
7501  CCTTCAGCTGCGAAACAATCAGGCTGGGCGAGATCTGTTTACAGCGCCATTCGTTTACCTTTCTCTGTAT

F  L  Y  P  I  I  S  V  F  I  M  S  F  Q  R  I  L  P  G  E  V  S  F  V  G  L  S  N  Y  T  A  L  N
7601  TTTTTCTATACCCATCATCAGTGTCTTCATCATGAGCTTCCAAAGAATTTGCCGGAGAGGTGTCCTTTGTCGGATTGTCAATTATACAGGCTAAA

N  P  T  F  Y  T  A  L  W  N  T  L  E  Y  T  F  W  T  L  I  V  L  I  P  V  L  L  A  I  F  L
7701  CAACCCGAGTTCTATACCGCCCTTTGGAATACCCTGGAATACACCTTTTGGACGCTGATCGTGCTGATTCCTGTTCGTCTTGCCATATTCCTG

N  S  K  L  V  K  F  R  N  I  F  K  S  A  L  F  I  P  A  L  T  S  T  I  V  A  G  I  I  F  R  L  I  F
7801  AATTCAAAGCTGGTCAAATTTAGAAATATTTAAATCAGCATTATTTATCCCGGCATTGACCTCAACCATTGTCGCGGGGATCATTTTTCGCCTGATCT

G  E  M  E  T  S  L  A  N  S  I  L  L  K  L  G  F  S  P  Q  N  W  M  N  N  E  H  T  G  M  F  L  M
7901  TCGGAGAAATGGAAACGTCTCTGGCCAATTCCATTCTACTTAAACTGGGCTTTTCACCTCAGAACTGGATGAACAATGAACATACCGGCATGTTTTGAT
```

FIG.2D-2

```
      V  L  L  A  S  W  K  W  M  M  G  I  N  I  L  Y  F  L  A  G  L  Q  N  V  P  K  E  L  Y  E  A  A  D  I
8001  GTGCTGCTTGTCTTCATGGAAATGATGGAAATCAACATCTTACTTTTTAGCAGGTTGCAGAATGTCCAAAATGTCCGAAGAGTCTACGAAGCCGCTGATATA

D  G  A  N  T  M  K  K  F  L  H  I  T  L  P  F  L  K  P  V  T  V  V  V  L  T  I  S  I  I  G  G  F  R
8101  GACGGCGGAATACAATGAAAAAATTCTGCACATCACGCTGCCGTTCTCAAGCCTGTATGTCTGACGTATACGATCAGCATCATCGGCGGCTTCA

M  F  E  E  S  Y  V  L  W  Q  N  N  S  P  G  N  I  G  L  T  L  V  G  Y  L  Y  Q  Q  G  L  A  Y  N
8201  GGATGTTTGAGGAAAGCTAGTCCTGCCTTTGACAACAATTCCCGGGTAATATTGTCTGCAGCTTGTCGGATATTGTATCAGCAGGACTTGCCTACAA

>>>>>  IR  <<<<<<<<<<
      E  M  G  Y  G  A  A  I  G  I  V  L  L  I  V  I  L  V  V  S  L  I  S  L  K  L  S  G  S  F  K  G  E
8301  TGAAATGGGATACGGAGCGGCCATTGGCATTGTCCTTGTTGATTGTAATCCTTGTCAGCCTGATTCATTAAAGCTCATTAAAGCTGTCAGGGTCTTGTTTAAGGGGAG araQ-  M  L  R  H  S  P  Q  F  S  V  Y  R  I  A  L  T  L  F  F  M  M  L  S  L  L  Y  L  F  P  I  F  C
      G  *
8401  GGATAAAGTTGCGGCACAGTCCTCAGTTTAGCGTTTATAGAATTGCGCTGACCCTGTTTTTATGATGCTATTGTATCTTTTCCGATTTCT L  L  L  G  S  L  K  P  S  S  E  L  L  R  V  G  L  N  L  D  I  D  P  K  V  M  S  F  D  N  Y  T  F
8501  GTTTGCTTTAGATCATTAAAGCCGTCATCTGAGTTTGGGTGGGCTGAATCTGATAATTGATCCAAAAGTGATGAGTTTTGATAACTACACATT
```

FIG. 2D-3

```
         L F N G G S I Y F K W F F N S L V L G L F T T V L T L F F S S M I
8601 TCTGTTAATGGGGCAGCATTTATTCAAATGGTTTTTTAACAGTCTGTTGACTCGACTGTGCTCACTGTGTTTCTTGATGATC
         G Y G L A V Y D F K G R N I I F V L L I I M M V P L E V M M L P L
8701 GGGTACGGGCTTGCGGTTTAAGGCAGAAATATCATCTTTGTCTTGCTGATTATAATGATGGTTCCCGTGAAGTGATGATGCTTCCTC
         F K L T V G L H L I D S Y T G V I L P F I V S P V A V F F F R Q Y
8801 TGTTTAAACTTACTGTCGGACTGCATCTGATCGATAGCTATACGGGTGTCATATTGCCGTTTATCGTTTCTCCTGTTTCAGGCAATA
         A L G L P R D L L D S A R M D G C T E F G I F F R I M A P L M K P
8901 TGCTCTTGGCCTTCCAAGAGATCTCTGACTCGAAGATGAGGCAATTCGTACGGAATTCGGCATCTTTTTCAGGATTATGGCACCGCTGATGAAACCG
         A F G A M I I L Q S L N S W N N F L W P L I V L R S K E M F T L P I
9001 GCTTTCGGTGCCATGATAATCTCCAGTCTTAAACAGCTGGAACAACTTCTTGTGGCCCTGATTGTGCTTCGGTCGAAGAAATGTTTACGCTTCCAA
         G L S S L L S P Y G N N Y D M L I S G S V F A I L P V I I F L F
9101 TAGGGCTGTCGTCCAGTCTGCCAGCCCTTATGGCTCAGAACTACGACATGCTTATATCGGTGATTATCATTTTCTTGTT
         F Q K Y F I S G L T V G G V K G *     rbs    abfA- M K K A R M I V D K
9201 TTTCCAAAAGTACTTTATCTCGGCCTGACGGTAGGGGAGTCAAAGTTAATGAGGAGAAACGTGATGAAAAAAGCCGCATGATTGTAGACAAA
         E Y K I G E V D K R I Y G S F I E H M G R A V Y E G I Y E P D H P E
9301 GAATATAAAATCGGTGAAGTAGATAAACGGATTTATGGCTCGTTTATCGAACATATGGGTCGTGCGGTATATGAAGGCATATACGAGCCTGATCACCCTG
```

FIG.2E-1

```
            A D E D G F R K D V Q S L I K E L Q V P I I R Y P G G N F L S G Y
 9401 AAGCGGATGAAGATGGATTAGAAAGATGTCCAGTCGCCTGATCAAAGAATTACAGGTTCCCATCATCCGTATCCCGGGCGAATTTTTATCCGGATA
            N W E D G V G P V E N R P R R L D L A W Q T T E T N E V G T N E F
 9501 CAACTGGGAGGACGGTGTCGGACCAGTCGAAAACCGCCCGACGCTTGACTTGGCATGGCAAACCACAGAAACCAATGAGGTTGGAACAAATGAATTT
            L S W A K K V N T E V N M A V N L G T R G I D A A R N L V E Y C N H
 9601 TTATCTTGGGCAAAAAAGGTCAACACTGAGGTCAATATGGCCGTCAACCTTGGCACAAGAGGCATAGATGCCGCCCGTAATCTGGTTGAATATTGCAACC
            P K G S Y W S D L R R S H G Y E Q P Y G I K T W C L G N E M D G P
 9701 ATCCGAAAGGCTCTTACTGGAGTGATTTAAGAAGATCATGGCAATCAAAACATGGTCTTAGAGAACGAAATGGATGGACC
            W Q I G H K T A D E Y G R L A A E T A K V M K W V D P S I E L V A
 9801 ATGGCAGATCGGCCACAAAACAGCTGATGAATACGGAAGACGGCTTGCCGCCGAGACAGCAGCAAAGGTCATGAAGTGGGTTGACCATCAATTGAACTGTTGCC
            C G S S N S G M P T F F I D W E A K V L E H T Y E H V D Y I S L H T Y
 9901 TGCGGCAGCTCAAACAGCGGTATGCCACCTTTATTGATTGGGAAGCAAAGGTGCTTGAGCATACGTATGAGCATGTCGACTATATCTCTTCACACTT
            Y G N R D N N L P N Y L A R S M D L D H F I K S V A A T C D Y V K
10001 ACTACGGAAACCGGGATAACAATCTGCCAAACTACTTGGCACGTTCTATGGATCTGGACCACTTTATCAAATCAGTGGCTGCCACCTGTGACTATGTAAA
            A K T R S K K T I N L S L D E W N V W Y H S N E A D K K V E P W I
10101 AGCAAAAACACCCGAAGCAAGAAAACTCAATCTCTCTCTGGATGAATGGAACGTCTGGTACCACTCAAATGAGGCTGATAAAAAAGTCGAGCCGTGGATC
```

```
         T  A  R  P  I  L  E  D  I  Y  N  F  E  D  A  L  L  V  G  S  L  L  I  T  M  L  Q  H  A  D  R  V  K  I
10201 ACTGGGGTCCGATTTTAGAGGATATTTACAATTTTGAAGATGCCTTATTAGTCGGCTCTCTGCTCATTACGATGCTGCAGCATGTCGCAGACCGAGTGAAAA

A  C  L  A  Q  L  V  N  V  I  A  P  I  M  T  E  K  G  G  E  A  W  R  Q  P  I  F  Y  P  Y  M  H  A
10301 TTGCGGTGTCTTGCACAGCTTGTAAATGTCATCGCGCCGATCATGACGGAAAAGGGCGAAGCATGGAGACAGCCGATTTCTATCCATACATGCATGC

S  V  Y  G  R  G  E  S  L  K  P  L  I  S  S  P  K  Y  D  C  S  D  F  T  D  V  P  Y  V  D  A  A  V
10401 TTCTGTGTTACGGAAGGGGCCAGTCACTGAAACCGCTTATTCTCTCCTAAGTACGATTGTTCTGATTCACTGATGTGCATATGTGATGCTGCTGTT

V  Y  S  E  E  E  T  L  T  I  F  A  V  N  K  A  E  D  Q  M  E  T  E  I  S  L  R  G  F  E  S  Y  Q
10501 GTGTACTCTGAAGAGGAAGAGACACTCACTATTTTTGCGGTAAACAAGGCTGAAGATCAGATGGAAACAGAGATCAGCTTCCGCGACGATTCCTCGAGCGTTTGAATCCTACC

I  A  E  H  I  V  L  E  H  Q  D  I  K  A  T  N  Q  H  N  R  K  N  V  V  P  H  S  N  G  S  S  S  V
10601 AAATCCAGAGCACATCGTACTTGAGCATCAGGATATCAAAGCAACAAACCAGCATAACAGAAAAAATGCCCATTCCAACGATCATCGTCTGT

S  E  N  G  L  T  A  H  F  T  P  L  S  W  N  V  I  R  L  K  K  Q  S  *
10701 CAGGGAAAACGGCTTAACTGCCTCATTTCACGCCCGCTTCCTTGAATGCATCAAGAATAGCAAACCGGAGATTTCTCCC
                                                                                    >>>>>>>>   T₁  <<<<<<

10801 GGCTTGCTCTTCAACTGCCACCAGCCGCCATTCCAGCCGGCCTTTTTGTATAGGAAAAAATGACCGCTTTCCACCATGAAATTATGATATTTATGAA
                           <<<<<<<   T₂  >>>>>>>>
```

FIG. 2E-3

```
Signature Sequence    LXXLGKXFEXDXXGIKVXV   (68-81)
                      I   IAD YT E  NV I L
                      V   VIQ  N A  DY   P
                      A    WV              P
                                P AraN Bs               YVEMVKEWNKKYYPDRKIKLNTVVYPY   (75)
```

FIG.4A

```
              10        20        30        40
Abf - B.su.   MKKARMIVDKEYKIGEVDKRIYGSFIEHMGRAVYEGIYEPDHPEADEDG
              ::: :: :::::::::::::::::::::::::::::::: :::: ::
Abf - B.st.   ATKKATMIIEKDFKIAEIDKRIYGSFIEHLGRAVYGGIYEPGHPQADENG
              10        20        30        40        50
```

FIG.4B

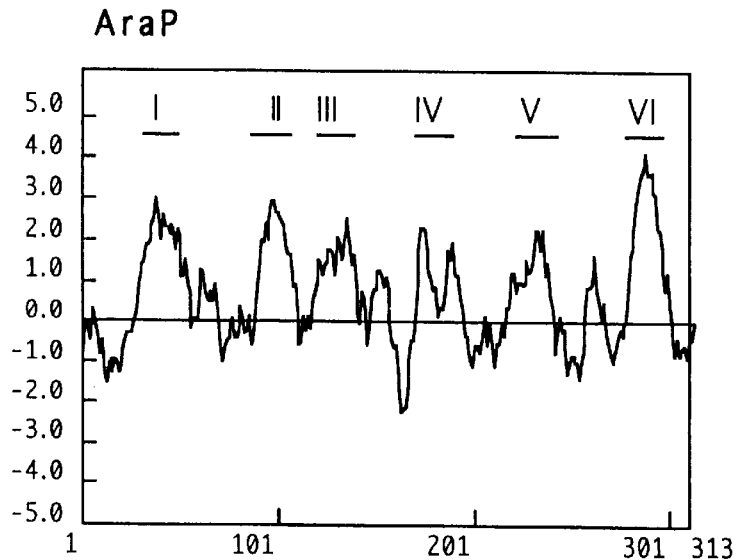
FIG.5A
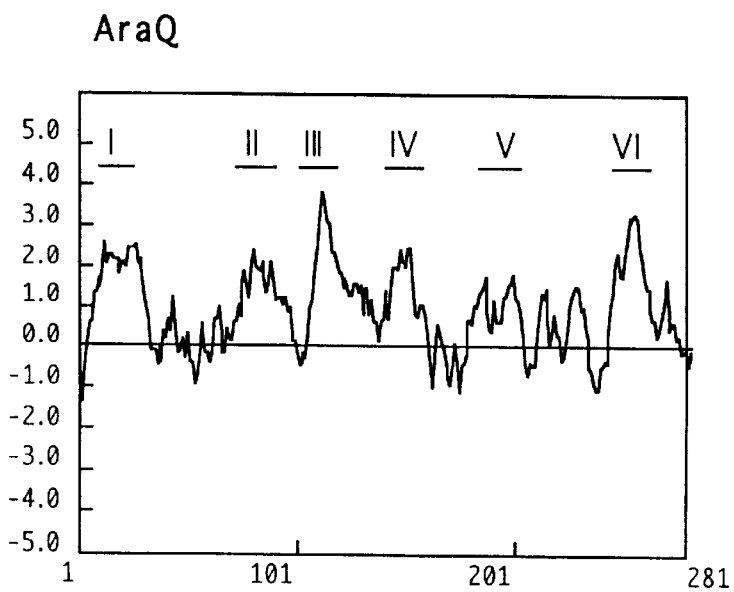
FIG.5B
```
AraP       198 GLQNVPKELYEAADIDGANTMKKFLHITLPFLKPVTVYVL (109)
                 .:..:..:  :::..:::......:  .:..::.:::  . ..:
Consensus      ALQSIPDSLIEAAKIDGAGPFQRFWNIVLPLLKPVLAVLL
                 ..: .:..:..::..:  . :  :....::..::......
AraQ       165 YALGLPRDLLDSARMDGCTEFGIFFRIMAPLMKPAFGAMI (100)
```
FIG.5C

```
araA
B.S.    MLQIKDYEFWFVIGSQHLYGEETLELVDQHAKSICEGLSGISS-RYKITHKPVVISPETTRELLREAEYSETLCAGIITWMHIFSPAKMIEGLSSYQKPL    99
E.C.    MTIFDNYEVWFVIGSQHLYGPETLRQVTQHAEHVVNALNTEAKLPCKLVLKPLGTTPDETTAICRDANVDDPCAGLVVWLHIFSPAKMWINGLIMLNKPL   100
S.T.                       A                                                                       S       100

B.S.    MHLHIQYNRDIPWGTIDMDFMNSNQSAHGDREYGYINSRMGLSRKVTAGYWDDEEVKKEMSQMMDTAAALNESRHIKVARFGNMRHVAVTDGKVGAHI    199
E.C.    LQFHTQFNAALPWDSIDMDFMNLNQTAHGREFGFIGARMRQQHAVVIGWMQDKQAHERIGSMRQAVSKQDITRHLKVCRFGDNMREVAVIDEKVAAQI    200
S.T.                                                                     E T   A        Q                   200

B.S.    QFGMQVDGYGIGDLVEMDRITIDEVDTLYAEYDRLYVISEETKRDEAKVASIKEQAKIEIGLTAFLEQGGYTAFTISFEVIHGMKQLPQLAVQRIMEQG    299
E.C.    KFGFSVNIWAVGELVQWNSISDGDVNALVDEYESCYTMTPATQIHGFKRQVLEAARIEIGMKRFLEQGGFFAFTITFEDHGLKQLPGLAVQRIMQQG    300
S.T.                                  G  I I  S L    D  R  G                                              300

B.S.    YGFAGEDMKTAALVRMKIMAKGKR--TSFMEDYTYHFEPGNEMILGSHMLEVCPIVALDQ-PKIEVHSLSIGGKEDPARLVFNGISGSAIQASTVDIG   396
E.C.    YGFAGEDMKTAALIRIMKVMSTIGLQGGISFMEDYTYHFEKGNDLVLGSHMLEVCPSTAVEEKPILDVQHLGIGGKDDPARLIFNIQIGPAIVASLIDLG   400
S.T.                                                      E                                                 400

B.S.    GRFRIVMLNEVNGQEIEKDMPNLPVARVLMKPEPSLKTAAEPAWILAGGAHHTICLSYELTAEQMLDWAEMAGIESVLISRDITTHKLKHELKWNEALYRLQK   496
E.C.    DRYRILVNCIDTVKTPHSLPKLPVANALWKAQPDLPTASEPAWILAGGAHHTIVFSHAILNLNMRQFABMHDIEITVILNDIRLPAFKDALRWNEVYYGFRR   500
S.T.              R                       D           I      A    H                                 K        500
```

```
araD
B.S.    MLETLKKEVLAANLKLQEHQLVFFTWGNVSGIDREKERIVIKLAESNISDLTADDLVVINLD-GEVVEGSLKPSSDTPTHVYLKAFPNIGGIVHTHSQW    99
        :::::::::::::::::::::::::::::::::::::::::::::::::::::::::::::::::::::::::::::::::::::::::::::::::::
E.C.    MLEDLKRQVLEANLALPKHNLVTLWGNVSAVDRERGVFVIKPSGVDYSIMIADDMVVSIEIGEVVEGAKKPSSDTPTHRLLYQAFPSIGGIVHTHSRH    100
                                        .                                            T
S.T.                    L               V                   L S    H
                                                                                                      .
B.S.    ATSMAQSGDRIPPLGTTHADYFLSALPCIREMYDEEIIHDYELNIGKVIAETFQHNYE---QVPGVLVNNHGPFCWGTDALNAITNAVLETVAEMAYHS    197
        :::::::::::::::::::::::::::::::::::::::::::::::::::::::::::::::::::::::::::::::::::::::::::::::::
E.C.    ATIWAQAQQSIPATGTTHADYFYGTIPCIRKMTDAEINGEYEWEIGNVIVETFEKQGIDAAQMPGVLVHSGPFAWGKNAEDAVHNAIVLEEVAYMGIFC    200
                         .                                                                             .
S.T.                   P                                      E
                                                                                                      .
B.S.    IMINKDVTPLNTVLHEEKHFYRKHGANAYYGQS   229
        :::::::::::::::::::::::::::::::
E.C.    RQLAPQLPLMQQTLLNKHYLRKHGAKAYYGQ     231
        ::
S.T.  H RRSCPTCSNPCWLNTLYANTAQKPITLGSNASKNASHG  240
```

FIG.9C

HIGHLY REGULABLE PROMOTER FOR HETEROLOGOUS GENE EXPRESSION

RELATED APPLICATIONS

The present Application is based on U.S. Provisional Application 60/031,077 filed Sep. 10, 1996 the priority of which is hereby claimed.

BACKGROUND OF THE INVENTION

1. Field of the Invention

The present invention relates to novel nucleic acid sequences which encode an operon involved in L-arabinose utilization. The operon includes a promoter which is both inducible and repressible and can be used to promote expression of genes in prokaryotics.

2. Description of the Related Art

*Bacillus subtilis*, an endospore-forming Gram positive bacteria, is able to grow on L-arabinose as the sole carbon source. L-arabinose residues are found widely distributed among many heteropolysaccharides of different plant tissues, such as arabinans, arabinogalactans, xylans, and arabinoxylans. Bacillus species in its natural reservoir, the soil, participate in the early stages of plant material decomposition, and *B. subtilis* secretes three enzymes, and endo-arabanase and two arabinosidases, capable of releasing arabinosyl oligomers and L-arabinose from plant cell walls [Kaji and Seheki, *Biochim. Biophys. Acta.*, 410:354–360 (1975); Weinstein and Albersheim, *Plant Physiol.*, 63:425–432 (1979)]. The pathway of L-arabinose utilization in *B. subtilis* was described by Lepesant and Dedonder [*C R Acad. Sci.*, Ser.D:2683–2686 (1967a)]. After entering the cell, L-arabinose is sequentially converted to L-ribulose, L-ribulose-5-phosphate, and D-xylulose-5-phosphate by the action of L-arabinose isomerase, L-ribulokinase and L-ribulose 5-phosphate 4-epimerase, respectively. D-xylulose-5-phosphate is further catabolized through the pentose-phosphate pathway. Mutants unable to use L-arabinose as sole carbon source, deficient in one of the three enzymes involved in L-arabinose catabolism, were characterized as well as constitutive mutants for all the three enzymes [Lepesant and Dedonder, 1967a, supra; Lepesant and Dedonder, *C R Acad. Sci.*, Ser.D:2832–2835 (1967b)]. The synthesis of these enzymes was shown to be inducible by L-arabinose and the isomerase activity subjected to catabolite repression by glucose and glycerol [Lepesant and Dedonder, 1967a, supra].

A collection of Ara⁻ *B. subtilis* mutants was isolated, biochemically characterized and the three metabolic genes, araA, araB and araD coding for L-arabinose isomerase, L-ribulokinase and L-ribulose 5-phosphate 4-epimerase, respectively, were identified and mapped between aroG and leuA, at about 256° on the *B. subtilis* genetic map [Paveia and Archer, *Brotéria Genética*, Lisboa, XIII(LXXX): 149–159 (1992a); Paveia and Archer, *Brotéria Genética*, Lisboa, XIII(LXXX):161–167 (1992b)]. Two additional classes of mutations affecting L-arabinose utilization were identified; one included mutations conferring and Ara⁻ phenotype to strains bearing the araA, araB and araD wild types alleles [Paveia and Archer, 1992a, supra; Paveia and Archer, 1992b, supra] and another comprised mutants showing constitutive expression of the three genes [Sá-Nogueira et al., *J. Bacteriol*, 170:2855–2857 (1988)]. These mutations were mapped between the cysB and hisA markers, at about 294° on the *B.subtilis* genetic map, and define another ara locus named araC. Expression of L-arabinose isomerase is severely repressed during growth in media containing L-arabinose plus glucose. Since L-arabinose isomerase expression is still regulated by catabolite repression in strains which contain constitutive mutations, araC$^C$, L-arabinose transport does not play a major role in catabolite repression of expression of the metabolic enzymes [Sá-Nogueira et al., 1988, supra]. The genes araA, araB and araD, have been cloned and by complementation experiments its products were shown to be functionally homologous to their *Escherichia coli* counterparts. Transformation experiments involving defined restriction fragments from the cloned genes showed that they are adjacent and probably constitute an operon with the order A-B-D [Sá-Nogueira and Lencastre, *J. Bacteriol.*, 171:4088–4091 (1989)], unlike the B-A-D order found in the *E. coli* operon [Englesberg et al., *Proc. Natl. Acad. Sci. USA*, 80:6790–6794 (1969)].

Expression of cloned genes introduced into bacteria has been, and is still, a mechanism for producing large amounts of a protein of interest for diagnostic and therapeutic purposes. In order to efficiently produce proteins in a prokaryotic host, a strong, regulated promoter is an essential element of the expression system.

Prokaryotic promoters used in the past include the bacteriophage lambda $p_L$ promoter, which is regulated by a temperature-sensitive repressor which represses transcription from that promoter at low temperatures. The $p_L$ promoter is used in an *E. coli* strain which contains a defective lambda prophage which encodes the repressor. This system is particularly suited for the expression of proteins which are toxic to *E. coli*. However, although the system is repressible, it does not provide a mechanism for inducibility.

Another prokaryotic promoter is the trp-lac promoter or tac promoter, which has been used to produce high levels of proteins in *E. coli*. This promoter is induced in the presence of isopropylthio-β-D-galactoside (IPTG). However, in order to subject the promoter to repression it must be used in an *E. coli* strain which produces lac repressor protein.

The bacteriophage T7 promoter can be used to express proteins in bacteria which are not normally efficiently transcribed by *E. coli* RNA polymerase. However, this system requires the use of an exogenous T7 RNA polymerase, and may require the use of specialized host cells, or supplemental infection with a bacteriophage in order to maintain low expression levels of proteins which are toxic to *E. coli*.

Therefore, in view of the aforementioned deficiencies attendant with prior art methods of controlling gene expression in prokaryotic hosts, it is apparent that there exists a need in the art for a promoter system for the expression of exogenous DNA in prokaryotes, which is highly regulable, i.e., is both inducible and repressible.

SUMMARY OF THE INVENTION

Briefly, the present invention features a promoter which is derived from an operon which contains three genes involved in L-arabinose utilization, araA, araB and araD which code L-arabinose isomerase, L-ribulokinase and L-ribulose 5-phosphate 4-epimerase (araA, araB and araD respectively). The operon additionally contains ribosome binding sites preceding each of the structural genes for L-arabinose utilization, and six regions which may be involved in transcription regulation, including four inverted repeats and two direct repeats.

In accordance with the present invention, an isolated nucleic acid molecule is provided which promotes the expression of genes in prokaryotes, and is both inducible and repressible on the addition of exogenous inducer or repressor respectively. The araC repressor is endogenous.

In a further embodiment, the genes encoding enzymes involved in L-arabinose utilization in *B. subtilis* are provided.

In its broadest aspect, the present invention extends to nucleic acid sequences encoding a promoter having the following characteristics:

a) promoting expression of genes in prokaryotes;
b) being inducible with L-arabinose; and
c) being repressible with glucose.

In a specific example, the promoter is contained by the sequence of SEQ ID NO:1, the operon has the sequence of SEQ ID NO:11, and the L-arabinose utilization enzymes have a nucleotide sequence of SEQ ID NO:35, 36 or 37.

In a still further aspect, the present invention extends to vectors for the expression of proteins in prokaryotes, and to the L-arabinose utilization enzymes which are expressed by the operon.

In a particular embodiment, the present invention relates to all members of the herein disclosed family of L-arabinose utilizing enzymes, particularly those having SEQ ID NOS:12, 13 and 14.

The present invention also relates to a recombinant DNA molecule or cloned gene, or a degenerate variant thereof, which encodes an operon which is preferably a nucleic acid molecule, in particular a recombinant DNA molecule or cloned gene, encoding the operon which has a nucleotide sequence or is complementary to a DNA sequence shown in FIG. 2 (SEQ ID NO:11).

The *B. subtilis* DNA sequences of the operon or promoter of the present invention or portions thereof, may be prepared as probes to screen for complementary sequences and genomic clones in the same or alternate species. The present invention extends to probes so prepared that may be provided for screening cDNA and genomic libraries for the operon or promoter. For example, the probes may be prepared with a variety of known vectors, such as the phage λ vector. The present invention also includes the preparation of plasmids including such vectors.

In a further embodiment of the invention, the full DNA sequence of the recombinant DNA molecule or the isolated promoter and regulatory regions are operatively linked as an expression control sequence to a gene encoding a protein to be expressed which may be introduced into an appropriate host. The invention accordingly extends to unicellular hosts transformed with the vector comprising a DNA sequence encoding the present operon or promoter, and more particularly, the complete DNA sequence determined from the sequences set forth above and in SEQ ID NOS:1 or 11.

According to other preferred features of certain preferred embodiments of the present invention, a recombinant expression system is provided to produce biologically active proteins which are eukaryotic or prokaryotic in origin.

The concept of the inducible/repressible operon or promoter contemplates that specific factors exist for correspondingly specific sequences within the operon, which lead to induction or repression in the presence of compounds such as L-arabinose, glucose and the like, as described earlier. Accordingly, the exact structure of each operon or promoter, and the corresponding factors, will understandably vary so as to achieve binding and activity specificity. It is this specificity and the direct involvement of the inducers and repressors in the chain of events leading to gene activation, that offers the promise of highly regulated procaryotic expression.

The present invention naturally contemplates several means for preparation of the operon or promoter, including as illustrated herein known recombinant and PCR techniques, and the invention is accordingly intended to cover such synthetic preparations within its scope. The isolation of the cDNA amino acid sequences disclosed herein facilitates the reproduction of the operon by such recombinant techniques, and accordingly, the invention extends to expression vectors containing the disclosed DNA sequences for expression in host systems by recombinant DNA techniques, and to the resulting transformed hosts.

The invention includes an assay system for screening of potential compounds effective to modulate transcriptional activity of target prokaryotic cells by interrupting or potentiating the activity of the operon or promoter. In one instance, the test compound could be administered to a cellular sample with the inducer or repressor that induces or represses the operon or promoter, or an extract containing the compound, to determine its effect upon the activity of the inducer or repressor to the operon or promoter DNA by comparison with a control.

The assay system could more importantly be adapted to identify factors that are capable of binding to the regulatory regions of the operon or promoter e.g. transcription factors or proteins, thereby inhibiting or potentiating transcriptional activity. Such drugs might be used to modulate the levels of expression from the promoters.

The present invention likewise extends to the development of antibodies against the enzymes involved in the utilization of L-arabinose (i.e; the Ara proteins), including naturally raised and recombinantly prepared antibodies. For example, the antibodies could be used to screen expression libraries to obtain the gene or genes that encode the Ara protein(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating transcriptional activity.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Accordingly, it is a principal object of the present invention to provide an isolated nucleic acid molecule, containing a sequence which promotes the expression of a protein in a prokaryotic host, wherein the sequence encoding the protein is operably positioned in proper reading frame 3' to the promoting sequence, and the expression is inducible in the presence of an appropriate exogenously supplied inducer or repressible in the presence of an appropriate exogenously supplied repressor.

In a particular embodiment, the nucleic acid has the sequence of SEQ ID NO:1; a sequence complementary to SEQ ID NO:1; or a homologous sequence which is substantially similar to SEQ ID NO:1.

A further object of the present invention is to provide a vector for the expression of a protein in a prokaryotic host which includes that nucleic acid sequence.

Another object of the invention is to provide a prokaryotic host transformed with the vector.

A still further object of the invention is to provide an isolated nucleic acid including the promoter sequence operably positioned in proper reading frame with at least one of an araA gene, an araB gene and an araD gene.

In a particular embodiment, the nucleic acid further includes a ribosome binding site 5' to each ara gene and/or at least one region which functions as an operator. In specific embodiments, the region includes an indirect or direct repeat sequence or a transcription terminator.

In one embodiment, the isolated nucleic acid has the sequence of:
  a) SEQ ID NO:11;
  b) a sequence which is substantially homologous to SEQ ID NO:11; or
  c) a fragment of any of (a) or (b) which retains the biological activity of SEQ ID NO:11.

Yet another object of the invention is to provide an isolated DNA molecule encoding a B. subtilis L-arabinose isomerase, or a fragment thereof, selected from the group of:
  a) the DNA sequence of SEQ ID NO:35;
  b) a DNA sequence complementary to SEQ ID NO:35;
  c) DNA sequences that hybridize to any of the foregoing DNA sequences under standard hybridization conditions; and
  d) DNA sequences that code on expression for an amino acid sequence encoded by any of the foregoing DNA sequences.

In a particular embodiment, the L-arabinose isomerase has an apparent molecular weight of approximately 56 kD, and contains approximately 496 amino acids.

In specific embodiments, the L-arabinose isomerase has the following sequence:
  a) SEQ ID NO:12;
  b) a sequence which is substantially homologous to SEQ ID NO:12; or
  c) a fragment of any of (a) or (b) which retains the biological activity of SEQ ID NO:12.

Still another object of the invention is to provide an isolated DNA molecule including a DNA sequence or degenerate variant thereof, which encodes an L-ribulokinase, or a fragment thereof, selected from the group consisting of:
  a) the DNA sequence of SEQ ID NO:36;
  b) a DNA sequence complementary to SEQ ID NO:36;
  c) DNA sequences that hybridize to any of the foregoing DNA sequences under standard hybridization conditions; and
  d) DNA sequences that code on expression for an amino acid sequence encoded by any of the foregoing DNA sequences.

Another object of the invention is to provide the L-ribulokinase encoded by the DNA molecule.

In a particular embodiment the L-ribulokinase has an apparent molecular weight of approximately 61 kD and/or contains approximately 560 amino acids.

In specific embodiments, the L-ribulokinase has the following sequence:
  a) SEQ ID NO:13;
  b) a sequence which is substantially homologous to SEQ ID NO:13; or
  c) a fragment of any of (a) or (b) which retains the biological activity of SEQ ID NO:13.

A further object of the invention is to provide an isolated DNA molecule comprising a DNA sequence or degenerate variant thereof, which encodes an L-ribulose 5-phosphate-4-epimerase, or a fragment thereof, selected from the group consisting of:
  a) the DNA sequence of SEQ ID NO:37;
  b) a DNA sequence complementary to SEQ ID NO:37;
  c) DNA sequences that hybridize to any of the foregoing DNA sequences under standard hybridization conditions; and
  d) DNA sequences that code on expression for an amino acid sequence encoded by any of the foregoing DNA sequences.

Another object of the invention is to provide the L-ribulose 5-phosphate-4-epimerase encoded by the DNA molecule.

In specific embodiments the L-ribulose 5-phosphate-4-epimerase has an apparent molecular weight of approximately 26 kD and/or contains approximately 229 amino acids.

In specific embodiments the L-ribulose 5-phosphate-4-epimerase has the following sequence:
  a) SEQ ID NO:14;
  b) a sequence which is substantially homologous to SEQ ID NO:14; or
  c) a fragment of any of (a) or (b) which retains the biological activity of SEQ ID NO:14.

Another object of the invention is to provide the isolated DNA molecules attached to detectable labels.

In specific embodiments, the detectable label is an enzyme, is fluorescent or radioactive.

Yet another object of the invention is to provide an antibody to the L-arabinose isomerase, the L-ribulokinase or L-ribulose 5-phosphate-4-epimerase.

In specific embodiments, the antibody may be polyclonal or monoclonal, and may be labelled with a detectable marker such as an enzyme, or a fluorescent or radioactive marker.

A further object of the invention is to provide a method for detecting proteins which regulate the present promoter sequence, including the steps of:
  a) incubating a sample in which a regulator protein may be present with the DNA sequence of SEQ ID NOS:2, 3, 4, 5, 6, 7 or 38;
  b) isolating any protein bound to the DNA sequences of step (a); and
  c) correlating the binding of the protein to the ability of the protein to regulate the promoter.

Other objects and advantages will become apparent to those skilled in the art from a review of the ensuing description which proceeds with reference to the following illustrative drawings.

BRIEF DESCRIPTION OF THE DRAWINGS

FIGS. 2A–E. Nucleotide sequence (SEQ ID NO:11) and translation of the *B. subtilis* ara region. The nucleotide sequence of the non transcribed strand is shown in the 5' to 3' direction. The predicted primary structure of the polypeptides encoded by the ara region are give in single letter code. The transcription start site (+1), defined by primer extension analysis, the −35 and −10 regions of the promoter and the putative ribosome binding sites (rbs) are underlined. Stop codons are represented by asterisks. Convergent arrows represent different regions of dyad symmetry (IR) and the two inverted represents though to act as transcriptional terminators for the ara operon are indicated by the letters $T_1$ and $T_2$. The catabolic repression associated sequences (position 191 to 204 and position 260 to 273) are underlined, The complementary sequence of the two primers A and B, used in primer extension analysis are represented below the sequence. The araA'-lacZ and araB'-lacZ fusion sites, confirmed by sequencing, are shown by an arrow.

FIGS. 4A–B. A. Alignment of a segment of the predicted sequence of AraN protein (SEQ ID NO:48) with the signature sequence (SEQ ID NO:47) of cluster 1 binding proteins, from binding-dependent transport systems, according to Tam and Saier, Microbiol Rev 57:320–346 (1993). Numbers in parenthesis indicate the positions of the last amino acid residues. The highly conserved lysine residue (K) is in boldface and the amino acid residues that match the signature sequence are underlined. B. Alignment of the amino terminal sequence (deduced from the nucleotide sequence) of AbfA from *B. subtilis* (B. su.) (SEQ ID NO:49) with the N-terminal sequence of α-L-arabinofuranosidase sequence from *B. stearothermophilus* (B. st.) (SEQ ID NO:50) Double dots represent identical amino acids and single dots represent conservative changes.

FIGS. 5A–B. A. Hydropathic index for the deduced amino acid sequences of AraP and AraQ protein according to the algorithm of Kyte and Doolittle, J Mol Biol 157:105–132 (1982). The hydropathy profiles are plotted from the N-terminus to the C-terminus by averaging hydropathy values over a window of ten residues. Hydrophobic segments which could correspond to membrane-spanning regions are labeled I–VI. B. Alignment of a hydrophilic segment, at approximately 100 residues from the C-terminus of the predicted sequence of AraP (SEQ ID NO:51) and AraQ (SEQ ID NO:53) proteins, with the consensus sequence (SEQ ID NO:52) for the group of integral cytoplasmic membrane proteins from binding protein-dependent transport systems (Saurin et al., Mol. Microbiol 12:993–1004 (1994) which includes permeases involved in the transport of disaccharide and glycerol phosphate. The general consensus for integral membrane proteins from binding protein-dependent permeases, EAA - - - G - - - I-LP (SEQ ID NO:44), where (-) represents any amino acid (Dassa et al., EMBO J. 4:2287–2293 (1985), is underlined. The distance of the invariant glycine residue from the C-terminus is represented in parenthesis. Double dots represented identical amino acids and single dots represent conservative changes.

FIG. 9. Comparison of *B. subtilis* araA, araB and araD gene products (SEQ ID NOS:12,13 and 14) with the *E. coli* and *S. typhimurium* AraA (SEQ ID NOS:16,17), B (SEQ ID NOS:18,19), and D (SEQ ID NOS:20,21) proteins. For *S. typhimurium* only, the amino acids that are different relative to *E. coli* are indicated. The alignments were made by the FASTA algorithm [Pearson and Lipman, Proc. Natl. Acad Sci. USA, 85:2444–2448 (1988)]. Dashes represent gaps introduced to maximize sequence similarities. Double dots indicate amino acid identity and single dots indicate a conservative amino acid change.

DETAILED DESCRIPTION OF INVENTION

The present invention provides an isolated nucleic acid molecule which promotes the expression of genes in prokaryotes, and is both inducible and repressible upon the addition of exogenous inducer or repressor, respectively.

In particular, the present invention provides the promoter for the *Bacillus subtilis* L-arabinose (ara) operon that is induced by L-arabinose and repressed by glucose. The ara operon is located at about 256° on the *Bacillus subtilis* genetic map, and comprises nine genes with a total length of 11 kb.

Therefore, if appearing herein, the following terms shall have the definitions set out below.

The "ara" operon is a single transcriptional unit that comprises nine genes, araA, araB, araD, araL, araM, araN, araP, araQ, and abfA whose expression is directed by a strong σ-A like promoter identified within a 150 bp DNA fragment upstream from the translation site of the araA gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site as well as protein binding domains (consensus sequences) responsible for the binding of RNA polymerase. Prokaryotic promoters contain Shine-Dalgarno sequences in addition to the −10 and −35 consensus sequences.

The "promoter of the present invention" is identified within a 150 bp DNA fragment upstream from the translation site of the araA gene. Situated 7 and 30 bp upstream from the ara operon transcription start site are sequences identical to the consensus −35 and −10 regions (TTGACA-17bp-TATAAT, SEQ ID NO:38) respectively, of promoters recognized by *Bacillus subtilis* σ-A containing RNA polymerase. The promoter of the present invention also contains three inverted repeats, putative operator-like sequences, in the −35 and −10 regions and a potential hairpin-loop structure with a ΔG value of −19.2 kcal/mol centered 27 bp upstream from the −35 region. The promoter is induced by L-arabinose and repressed by glucose.

Figure 11:
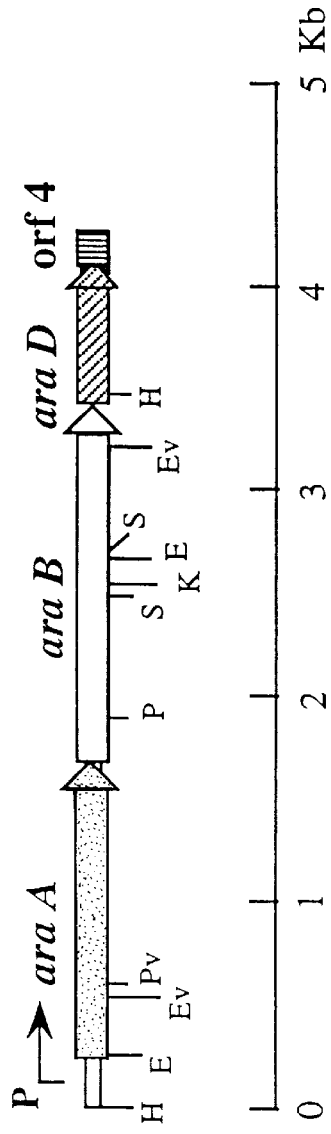
FIG. 11. (A) Physical map of the ara operon. Only relevant restriction sites are shown: Eco RI (E); Eco RV (Ev); Hind III (H); Kpn I (K); Pst I (P); Pvu I (Pv); Sma I (S). The location and direction of transcription of the four open reading frames (araA, araB, araD and ORF4 are indicated by arrows. The promoter (P) of the ara operon is indicated by the arrow preceding araA. (B) The nucleotide sequence of the promoter region. The −35 and −10 regions of the promoter are shown in boxes. The transcription start site (+1) and the two sequences similar to the consensus sequence for catabolite repression (CR-TGWNANCGNTNWCA) (SEQ ID NO:8), are underlined. Convergent arrows indicate four different regions of dyad symmetry (IR1, IR2, IR3 and IR4) (SEQ ID NOS:2–5, respectively) and direct arrows indicate regions of direct repeats (DR). The ribosome binding site (RBS) preceding the araA coding regions is shown in bold letters.
Figure 11:
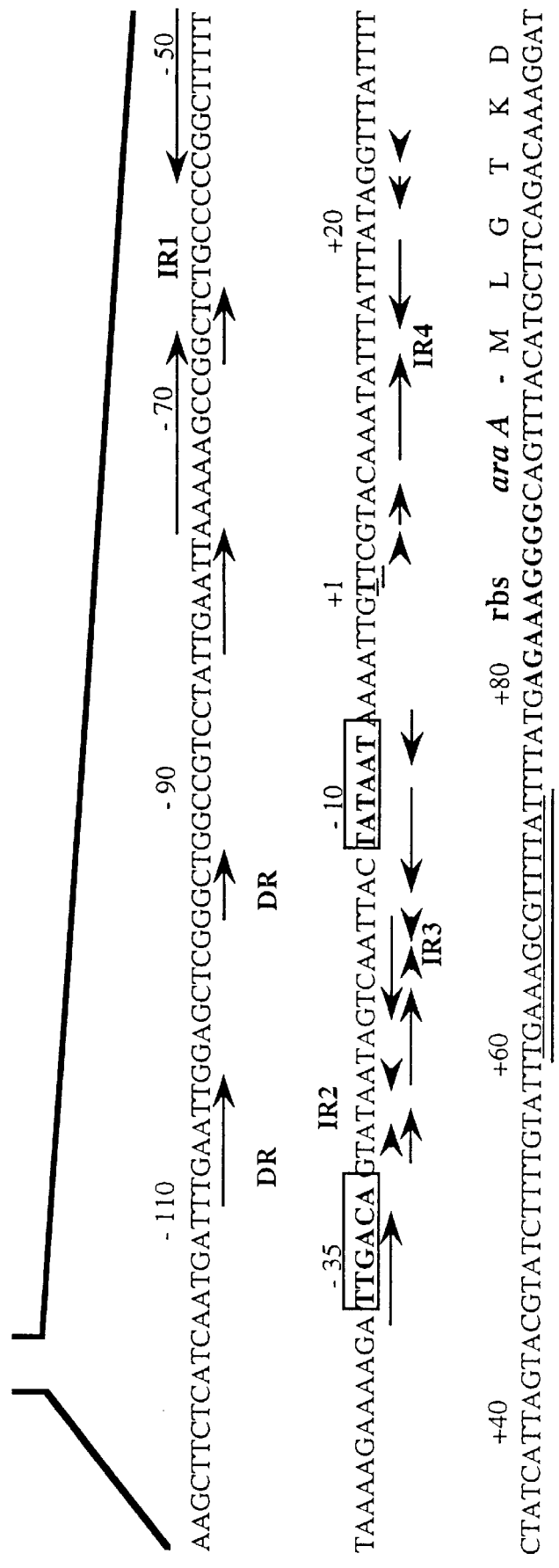

Thus there are at least six regions likely to be involved in transcription regulation identified near the promoter of the present invention (FIG. 11) (SEQ ID NO:1). The first two were found upstream from the −35 region: an inverted repeat of ten nucleotides (IR1) located upstream from the −35 region (position −49 to −77, FIG. 11 (SEQ ID NO:2) and two direct repeats (comprise between position −66 to −113, FIG. 11). Downstream from IR1, three other inverted repeats were found: the first, IR2, located in the −35 region (SEQ ID NO:3); the second, IR3, located in the −10 region; and the third (SEQ ID NO:4); IR4, in the +4–+20 region (SEQ ID NO:5) (FIG. 11). All these sequences may be putative operator-like regions, and IR1 might also be a putative transcription terminator of a gene located upstream from the cloned fragment. Downstream from the transcription start site, the DNA sequence, +20-ATAGGTTTATTTTCTATC ATTAGT ACGT-+47 (SEQ ID NO:6) (FIG. 11) show some similarity to the sequence recognized by the product of the regulatory gene, araC, at the *E.coli* araBAD promoter ATAGCATTTTTATCCATAAGATTAGCGG (SEQ ID NO:7) (Brunell, A. and Schleif, R., 1989).

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to a probe of the present invention, is defined as a molecule comprised of two or more ribonucleotides, preferably more than three. Its exact size will depend upon many factors which, in turn, depend upon the ultimate function and use of the oligonucleotide.

As used herein, the terms "restriction endonucleases" and "restriction enzymes" refer to bacterial enzymes, each of which cut double-stranded DNA at or near a specific nucleotide sequence.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. A "clone" is a population of cells derived from a single cell or common ancestor by mitosis. A "cell line" is a clone of a primary cell that is capable of stable growth in vitro for many generations.

Two DNA sequences are "substantially similar" when at least about 75% (preferably at least about 80%, and most preferably at least about 90 or 95%) of the nucleotides match over the defined length of the DNA sequences. Likewise, two protein sequences are "substantially similar" when at least about 75% (preferably at least about 80% and most preferably at least about 90 or 95%) of the amino acids match or are conservative substitutions, as described below. Substantially similar genes and proteins, as defined above, are preferably homologous. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The terms "Ara proteins", "proteins involved in utilization of L-arabinose", "L-arabinose utilization enzymes", and any variants not specifically listed, may be used herein interchangeably, and as used throughout the present application and claims refer to proteinaceous material including single or multiple proteins, and extends to those proteins having the amino acid sequence data described herein and presented in FIG. 9 (SEQ ID NOS:12, 13 and 14), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "Ara proteins", "proteins involved in utilization of L-arabinose", "L-arabinose utilization enzymes" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

The term "standard hybridization conditions" refers to salt and temperature conditions substantially equivalent to 5×SSC and 65° C. for both hybridization and wash.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In its primary aspect, the present invention concerns the identification of an operon encoding enzymes involved in L-arabinose utilization.

In a particular embodiment, the present invention relates to an operon isolated from *B. subtilis*.

Figure 2D-1:
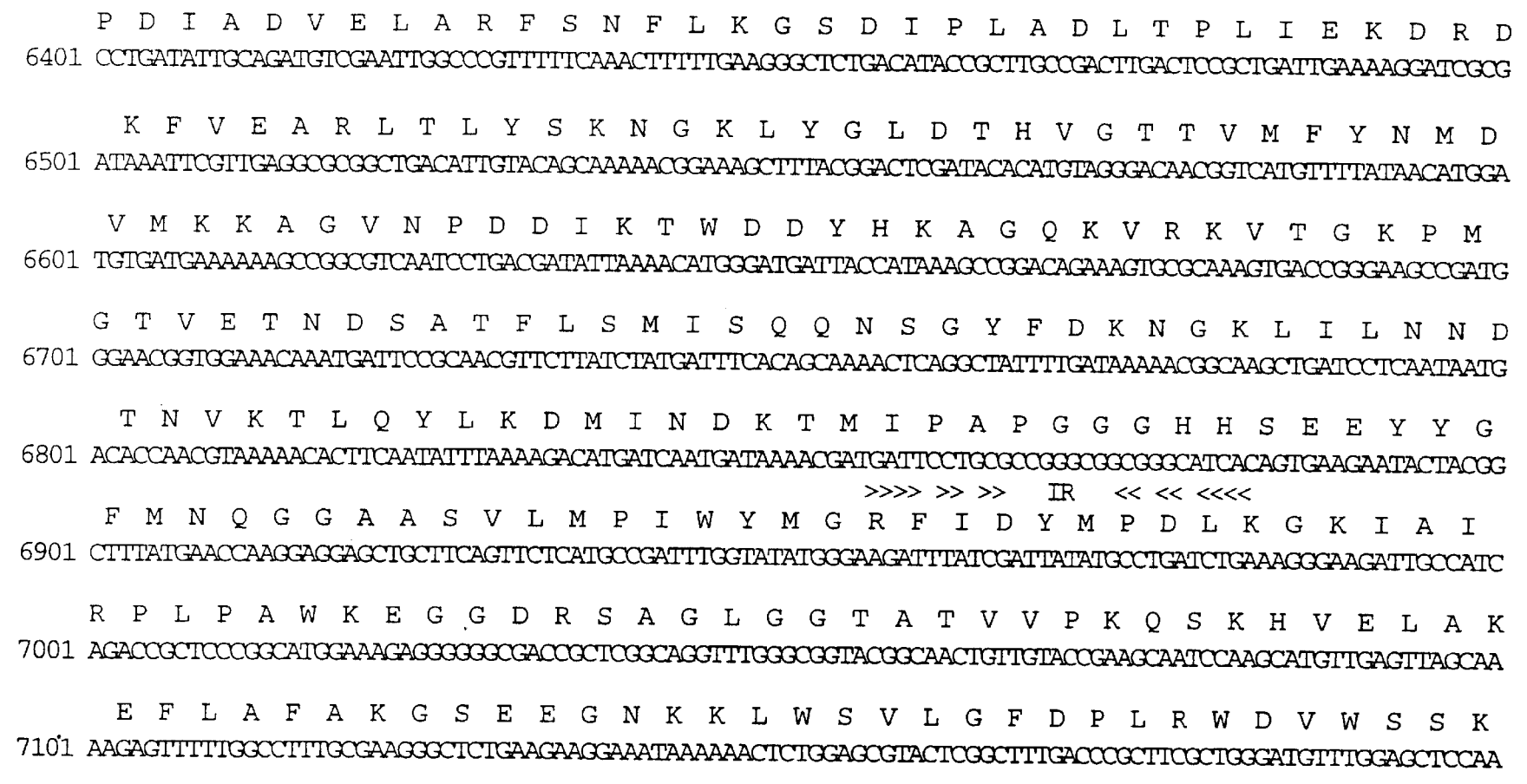

As stated above, the present invention also relates to a recombinant DNA molecule or cloned gene, or a degenerate variant thereof, which encodes an L-arabinose isomerase, or a fragment thereof, that possesses a molecular weight of about 56 kD and an amino acid sequence set forth in FIG. 2 (SEQ ID NO:12); preferably a nucleic acid molecule, in particular a recombinant DNA molecule or cloned gene, encoding the 56 kD L-arabinose isomerase has a nucleotide sequence or is complementary to a DNA sequence shown in FIG. 2 (SEQ ID NO:35).

The present invention also relates to a recombinant DNA molecule or cloned gene, or a degenerate variant thereof, which encodes an L-ribulokinase, or a fragment thereof, that possesses a molecular weight of about 61 kD and an amino acid sequence set forth in FIG. 2 (SEQ ID NO:13); preferably a nucleic acid molecule, in particular a recombinant DNA molecule or cloned gene, encoding the 61 kD L-ribulokinase has a nucleotide sequence or is complementary to a DNA sequence shown in FIG. 2 (SEQ ID NO:36).

Likewise the present invention also relates to a recombinant DNA molecule or cloned gene, or a degenerate variant thereof, which encodes an L-ribulose-5-phosphate-4-epimerase, or a fragment thereof, that possesses a molecular weight of about 26 kD and an amino acid sequence set forth in FIG. 2 (SEQ ID NO:14); preferably a nucleic acid molecule, in particular a recombinant DNA molecule or cloned gene, encoding the 26 kD L-ribulose-5-phosphate-4-epimerase has a nucleotide sequence or is complementary to a DNA sequence shown in FIG. 2 (SEQ ID NO:37).

The possibilities for both diagnostic uses and uses in protein expression systems derive from the fact that factors appear to participate in direct and causal interaction with the regulatory regions of the operon which induce or repress transcription and accordingly gene activation. As suggested earlier and elaborated further on herein, the present invention contemplates pharmaceutical intervention in the cascade of reactions in which the regulatory regions are implicated, to modulate the activity initiated by the factors bound to there regulatory regions.

Thus, in instances where it is desired to repress the transcriptional activity directed by the promoter, an appropriate repressor of the operon could be introduced, which either acts with those factors causally connected with gene activation or which itself binds a repressor region of the operon. Correspondingly, instances where insufficient gene activation is taking place could be remedied by the introduction of the inducer of the operon or its chemical or pharmaceutical cognates, analogs, and the like. Alternatively, a factor which interacts with the repressor may also be used to inhibit repression, resulting in increased gene activity.

Another feature of this invention is the expression of the DNA sequences disclosed herein as well as use of the promoter of the L-arabinose operon for expressing exogenous DNA. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence and a termination codon and 3' regulatory sequence.

A wide variety of host/expression vector combinations may be designed employing the DNA sequences of this invention. Useful expression vectors, for example, may consist of segments of chromosomal, non-chromosomal and synthetic DNA sequences. Suitable vectors include derivatives of and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors derived from combinations of plasmids and phage DNAS, such as plasmids that have been modified to employ phage DNA or other expression control sequences; and the like.

A wide variety of unicellular host cells are useful in the expression of DNA sequences by this invention. These hosts may include well known prokaryotic hosts, such as strains of *E. coli*, Pseudomonas, Bacillus, and Streptomyces.

It will be understood that not all exogenous DNA sequences may be regulated by the vectors, expression control sequences and hosts of the invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale culture.

It is further intended that L-arabinose enzyme analogs may be prepared from nucleotide sequences of the protein complex/subunit derived within the scope of the present invention. Analogs, such as fragments, may be produced, for example, by pepsin digestion of enzyme containing material. Other analogs, such as muteins, can be produced by standard site-directed mutagenesis of enzyme coding sequences. Analogs exhibiting "L-arabinose utilizing activity" such as small molecules, whether functioning as promoters or inhibitors, may be identified by known in vivo and/or in vitro assays.

As mentioned above, a DNA sequence encoding the operon, the promoter or the enzymes of the operon can be prepared synthetically rather than cloned. The DNA sequence can be designed with the appropriate codons for the particular enzyme's amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express enzyme analogs or "muteins". Alternatively, DNA encoding muteins can be made by site-directed mutagenesis of native enzyme genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

In accordance with the above, an assay system for screening potential factors effective to modulate the activity of the operon may be prepared. The operon may be introduced into a test system, and the prospective factor may also be introduced into the resulting cell culture, and the culture thereafter examined to observe any changes in the transcriptional activity from the operon due either to the addition of the prospective factor alone, or due to the effect of added quantities of the known enzymes, repressors or inducers.

Preliminary Considerations

The three genes involved in L-arabinose utilization, araA, araB and araD were previously identified by mutations conferring an Ara⁻ phenotype and were mapped between aroG and leuA on the *Bacillus subtilis* chromosome [Paveia et al., 1992, supra]. These enzymes were shown to be inducible and the isomerase activity subject to catabolite repression [Lepezant and Dedonder, 1967, supra].

Two different classes of mutations affecting L-arabinose utilization which map at another locus, araC, located between the cysB and hisA markers, have also been identified [Sá-Nogueira et al., 1988, supra]. The first class includes mutations, conferring an Ara⁻ phenotype to strains bearing the araA, araB and araD wild type alleles. Mutants of the second class show constitutive expression of the araA, and araB and araD genes. These mutations define a locus, araC, which might play a role in the regulation of L-arabinose utilization. Constitutive mutants still retain catabolite repression of L-arabinose isomerase expression, suggesting that a mechanism other than inducer exclusion, plays a role in the carbon regulation of isomerase expression [Sá-Nogueira et al., 1988, supra].

By the present invention, these genes have been cloned from *Bacillus subtilis* and the gene order established as araABD, unlike the one found in *E. coli* which is araBAD [Sá-Nogueira and Lencastre, 1989, supra].

To understand further the genetics and regulation of L-arabinose utilization in *B. subtilis*, studied the structure and transcription of the araA, araB and araD genes were studied. The results obtained show that the three genes involved in the early steps of L-arabinose utilization are organized in an operon, araABD, and σA-like promoter was identified within a 150 bp DNA fragment upstream from the translation start site of the araA gene.

This operon appears to be regulated mainly at the transcriptional level because the synthesis of the ara mRNA is induced by L-arabinose and is repressed by glucose.

The following examples are presented in order to more fully illustrate the preferred embodiments of the invention. They should in no way be construed, however, as limiting the broad scope of the invention.

EXAMPLES

Example 1

Nucleotide Sequence, Genetic Organization and Expression of the *Bacillus subtilis* L-Arabonose Operon Introduction The cloning of an additional 7.1 kb chromosomal fragment, located downstream from the araD gene, and the nucleotide sequence of over 11 kb is reported. This region contains a cluster of nine genes: the metabolic genes araA, araB, araD, and six new genes here named araL, araM araN, araP,araQ, and abfA. All genes are comprised of a single transcriptional unit, called the ara operon, whose expression is directed by a single σ-A type promoter identified within a 150 bp DNA fragment upstream from the translation start site of the araA gene. The araN, araP and araQ products are likely components of a binding-protein-dependent transport system and the abfA gene most probably codes for an α-L-arabinofuranosidase. The promoter region of the ara operon is defined and examined and its expression and regulation using transcriptional fusions of this operon to the *E. coli* lacZ gene are disclosed. These results indicate that the ara operon is regulated at the transcriptional level because expression from the ara promoter is induced by L-arabinose and repressed by glucose.

Results

Figure 1:
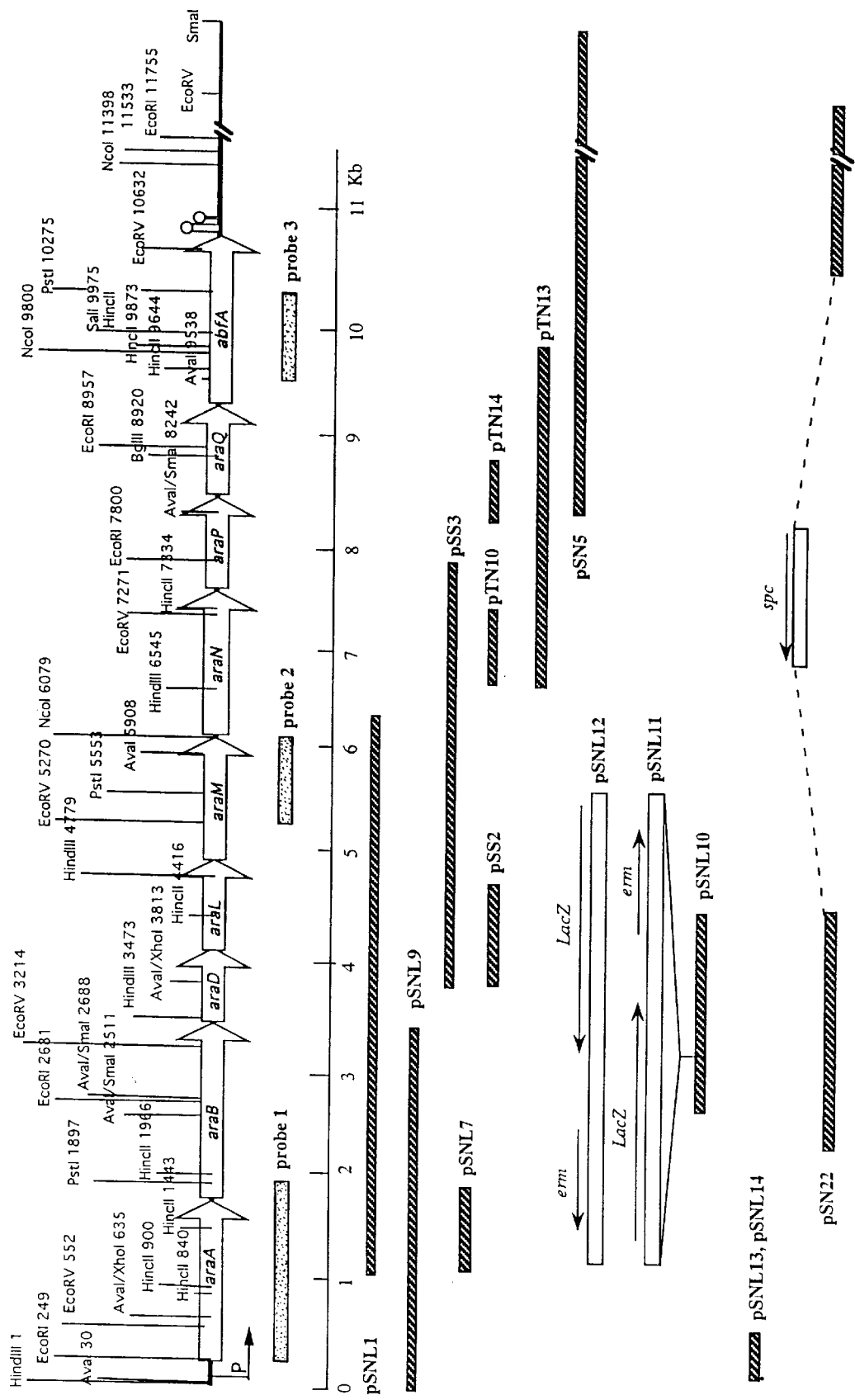
FIG. 1. Physical and genetic map of the ara region of the chromosome. The location and direction of transcription of the nine open reading frames (araA, araB, araD, araL, araM, araN, araP, araQ and abfA), predicted from the analysis of the nucleotide sequence, are indicated by arrows. The promoter (P) of the ara operon, defined by primer extension, is located upstream the araA gene and the two region of dyad symmetry that could represent the terminators of the ara transcriptional unit are located downstream the abfA gene. The position for each restriction site, according to the nucleotide sequence is given in the partial restriction map. The region to the right of the EcoRI site (position 11755) is not drawn to scale. The open boxes, below the physical map, represent the three fragments used as probes for Northern analysis of the ara transcripts and the striped boxes (▨) represent the extension of the inserts in the indicated plasmids. The sites of different insertion-deletion mutations resulting from replacement of wild-type sequences, by double-crossover events, with in vitro-engineered fragments of the ara region, present in plasmids pSNL11, pSNL12 and pSN22, are also shown. Plasmids pSNL7, pSS2, pTN10, pTN14, pSNL13 and pSNL14 were integrated into the host chromosome by means of a single crossover (Campbell-type) recombinational event that occurred in the region of homology.

Insertional inactivation of the araB gene and cloning of an intact copy of araA gene The location of the araa locus at one end of the cloned fragment in pSNL1 (FIG. 1), together with the absence of araA complementation with pSNL1, suggested that only part of the araA gene was present in this plasmid (Sá-Nogueira & Lencastre, *Bacillus subtilis* J Bacteriol 170:2855–2857 (1988). To clone the entire araA gene, a DNA fragment containing part of the araA and araB genes were inserted into the integrational vector pJM783 (see Experimental procedures). The resulting plasmid, pSNL7 was used to transform *B. subtilis* 168T+ to Cm$^r$. The plasmid integrates into the *B. subtilis* chromosome at the ara region of homology by a Campbell-type recombination mechanism, which causes disruption of the araB gene (FIG. 1); the structure of the resulting strain IQB100 was confirmed by Southern Hybridization (data not shown). This strain was unable to grow on minimal medium, containing L-arabinose as sole carbon source. Furthermore, it showed resistance to ribitol in the presence of L-arabinose on minimal medium plates supplemented with casein hydrolysate 1% (w/v). In *B. subtilis* (Paveia & Archer, *Bacillus subtilis*. Broteria Genetics, Lisboa XIII (LXXX): 149–159 (1992a) like in *E. col* (Katz, J. Bacteriol 102: 593–595 (1970) these results indicate a defective araB gene. Chromosomal DNA from IQB100 digested with HindIII was used to rescue the entire araA gene and its upstream region (see Experimental procedures). The structure of the recircularized plasmid, pSNL9, was analyzed and it contains a 950 pb fragment of DNA upstream to the previously cloned DNA in plasmid pSNL7 (FIG. 1).

Cloning of the chromosomal region extending downstream from the araD gene

To clone the region located downstream from the araD gene an integrational plasmid pSS2, carrying sequences of araD and araL (FIG. 1), was transformed into the wild type strain 168T+. After integration via single cross-over recombination, confirmed by Southern hybridization analysis (data not shown), the resulting strain IQB202 presented an Ara+ phenotype; however, the growth on minimal medium plates with L-arabinose as the sole carbon source was slower than the one observed with the wild type strain 168t+ (see discussion below). Total chromosomal DNA from IQB 202, was digested with EcoRI, selfligated and transformed into E. coli (see Experimental Procedures). The resulting plasmid pSS3 includes a 3.0 kb insert located downstream to the fragment cloned in pSS2. In order to obtain a fragment that would contain the downstream region from araN, we performed a second chromosome walking step, using integrational plasmid pTN10 (FIG. 1). This procedure created plasmid pTN13 that carried an additional 3.2 kb of DNA adjacent to the previously cloned fragment in plasmid pTN10 (FIG. 1). Strain IQB204 which resulted from the integration of plasmid pTN10 (FIG. 1) into the chromosome of the wild type strain 168T+, via a Campbell-type recombination (confirmed by Southern hybridization analysis; data now shown) showed a Ara+ phenotype similar to that seen with IQB202. A third chromosome walking step rightwards from pTN13, using integrational plasmid pTN14 (FIG. 1) isolated a 4.7 kb SmaI fragment (plasmid pSN5). Plasmid pTN14 when integrated into the chromosome, strain IQB205 (the correct integration was checked by Southern blot analysis; data not shown), caused a Ara+ phenotype. The structure of the inserts of pSS3, pTN13 and pSN5 was compared to that of the corresponding areas of chromosomal DNA by Southern blot analysis (data not shown) and the results revealed that no detectable rearrangement occurred during the cloning process.

DNA Sequence and deduced products of the ara genes

Figure 3A:
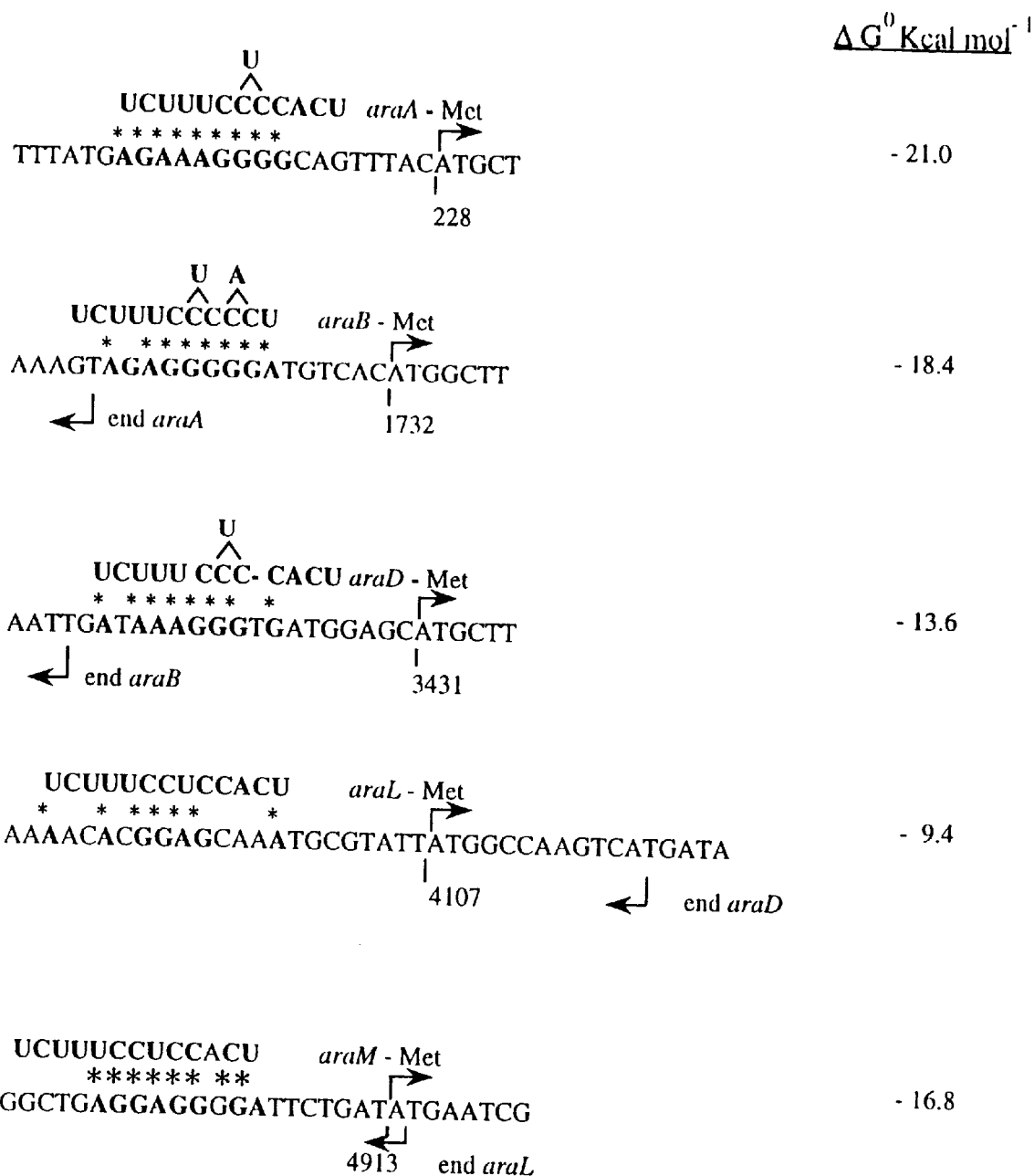
FIG. 3. Intercistronic regions and putative transcription termination sites of the ara operon (SEQ ID NOS:22, 23, 27, 28, 29, 30, 31, 33, 38, 39, 40, 41, 42, and 43). The DNA sequence of the non-transcribed strand is shown. The initiation codon is indicated above each triplet by "met", while the stop codons are indicated below each triplet by "end". The possible pairing with the 3' end of 16S rRNA is indicated above each sequence (ribosome binding site). The free energy ($AG^0$) of interaction for each putative ribosome binding site and for the predicted stem-loop structures of the putative terminators of the ara operon, T1 and T2, were calculated according to the rules of Tinoco et al., Nature New. Biol. 246:40–41 (1973).
Figure 3B:
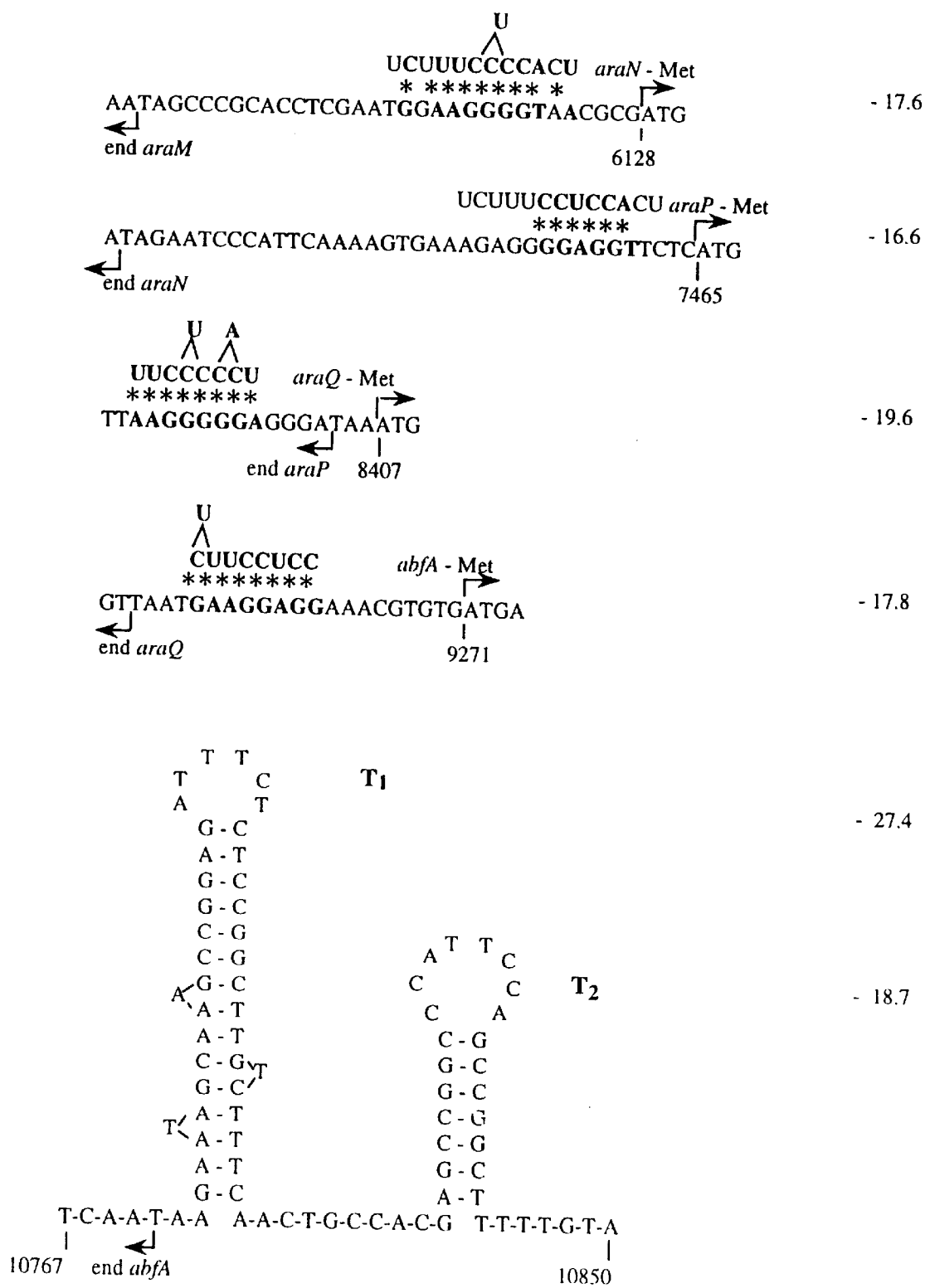

Appropriate restriction fragments selected on the basis of the physical maps of pSNL1, pSNL9, pSS3, pTN13 and pSN5, were subcloned into M13mp18 and M13mp19 and used as templates to determined the nucleotide sequence of the 11 kb DNA region shown in FIG. 1; both strands were sequenced, across all the restriction sites used for cloning (see Experimental procedures). Sequence analysis revealed the presence of nine open reading frames (ORFs) in the region; the first three, by its position in the sequenced fragments of pSNL1 and pSNL9 and according to our previous results (Sá-Nogueira & Lencastre, Bacillus subtilis J Bacteriol 170:2855–2857 (1989), were identified with the araA, araB and araD genes (FIG. 1). The araA, araB and araD genes could encode a 496, 560, and 229 amino acid products of 56.2 kDa, 60.9 kDa, and 25.7 kDa, respectively (FIG. 2). The six ORFs found downstream from the araD gene, herein named araL, M, N, P, Q and abfa (FIG. 1), of 269, 394, 433, 313, 281 and 499 codons, are capable of encoding putative products of 29 kDa, 43.1 kDa, 48.7 kDa, 35 kDa, 31.8 kDa and 57 kDa, respectively (FIG. 2). All ORFs are preceded by strong ribosome binding sites with the exception of araL which is a weak ribosome binding sit (FIG. 3). The intercistronic regions are very short and overlapping was observed between the araD and araL coding sequences, and between araL and araM, suggesting translational coupling. Two potential hairpin-loop structures, situated next to the UAA stop codon of the abfA gene ($T_1$ and $T_2$ FIG. 3), probably correspond to transcription terminators. The absence of transcriptional signals among the nine coding regions suggested that they form a large operon transcribed from a promoter (described below) positioned 104 nucleotides upstream from the araA start codon (FIG. 2).

Comparison of the primary structures of the products predicted to be encoded by the ara genes with sequences in the GenBank revealed significant similarities with other bacterial proteins of known function and the results are summarized on Table 1. The putative product of araM, a hydrophilic protein, did not show any significant similarity.

The araA, araB and araD gene products exhibited a high level of identity to the L-arabinose isomerase, L-ribulokinase and L-ribulose 5 phosphate-4-epimerase, respectively, of E. coli and S. thyphimurium. The product of the araL gene, a hydrophilic protein, displayed similarity to the NagD gene product of unknown function, which belongs to the nag regulon E. coli involved in the metabolism of N-acetyl glucosamine (Plumbrigde, Mol Microbiol 3:505–515 (1989)). The N terminal region of the predicted sequence also shared 28.1% and 29.2% identity (over 121 and 106 amino acid residues, respectively, data not shown) with two 4-nitrophenylphosphatases, Pho2 and Pho13, Schizosaccharomyces pombe (Yang et al. 1991) and Saccharomyces cereviseae (Kaneko et al., 1989), respectively. The predicted primary structure of araN showed similarity to known sugar-binding proteins that belong to the family of binding-protein-dependent transport systems (Table 1). Although the identity was not very high there was a significant sequence conservation within the N-terminal of these proteins which display a signature sequence, according to Tam and Saier (1993). On the basis of this signature sequence (FIG. 4A) AraN can be included in the cluster 1 binding proteins (according to Tam and Saier 1993), together with the above mentioned proteins involved in the transport of malto-oligosacharides and multiple sugars. The hydropathic profile of AraN indicate that it is mainly a hydrophilic protein; however its N-terminal region (FIG. 2) displayed characteristics of signal peptides of secretory precursor proteins: positively charged N terminus, a hydrophobic core and a sequence IAGCSA (starting at amino acid 19, FIG. 2) which corresponds to the consensus sequence for the precursors of lipoprotein (reviewed in Hayashi and Wu, 1990). The predicted products of araP and araQ exhibited hydropathy profiles (according to Kyte and Doolittle, 1982) characteristics of integral membrane proteins: six major regions of high hydrophobicity (hydrophatic index>1,0), each composed of at least 20 amino acids which could be capable to spanning the membrane (FIG. 5A). AraP and AraQ shared an identity of 19.6% and showed significant similarity with integral cytoplasmic membrane proteins involved in prokaryotic binding-protein dependent transport systems (Table 1). As most of these integral membrane proteins, AraP and AraQ have conserved hydrophilic segment (FIG. 5B) at approximately 100 residues from the C-terminus with the consensus "EAAxxxGxxxxxxIxLP" (SEQ ID NO: 44) (Dassa and Hofnung, 1985). Furthermore, on the basis of this signature sequence they can be included in the disaccharide sub-cluster proposed by Saurin et al., 1994 together with the above mentioned proteins involved in the transport of malto-oligosaccharides, multiple sugars and α-glycerol phosphate. The deduced product AbfA, a hydrophilic protein, displays a N-terminal region (FIG. 4B) which resembles a signal peptide of exoproteins: positively charged N terminus and a hydrophobic core (reviewed on Gierasch, 1989 and Nagarajan, 1993). The primary structure of the putative product of abfA is closely related to the α-L-arabinofuranosidase of Streptomyces lividans (Table 1) and the N-terminal region (FIG. 4) is 74% identical and 96% similar to the sequences N-terminus of purified α-L-arabinofuranosidase from B. stearothermophilus (Gilead and Shoham, 1995). These observations strongly suggest that the abfA gene encodes for an α-L-arabinofuranosidase.

RNA Transcript analysis of the L-arabinose gene region

Figure 6A:
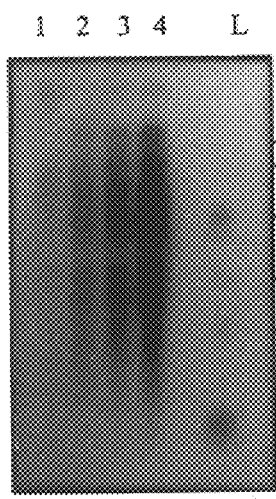
FIGS. 6A–C. Northern analysis of the ara operon-specific transcripts. A. B. and C: Lanel, 10 μg of total RNA extracted from the uninduced wild type strain *B. subtilis* 168T+; Lanes 2, 3, and 4; 2.5 μg, 5 μg and 10 μg, respectively of total RNA extracted from the induced wild type stran *B. subtilis* 168T+ L-arabinose (see methods); Lane L, 4 μg of the RNA ladder (9.5–0.24 kb; Givco/BRL). The samples were run in: A. 1% (w/v) and B., C. 1.2% (w/v) agarose formaldehyde denaturing gel. The $^{32}$P-labeled probes used were synthesized from: A. 1.6 kb EcoRI-PstI fragment (position 249 to 1897, Probe 1 FIG. 1); B. a 0.8 kb NcoI-EcoRV fragment (position 5270 to 6079, Prob 2, FIG. 1) C. a 0.7 kb PstI-AvaI fragment (position 9538 to 10275, Probe 3, FIG. 1). L: 4 μg of the RNA ladder (9.5–0.24 kb; Gibco/BRL) was probed with $^{32}$P labeled 2 DNA and also visualized by staining with ethidium bromide. The transcript of about 11 kb comprising all genes and detected with the three probes is indicated by an arrow.
Figure 6B:
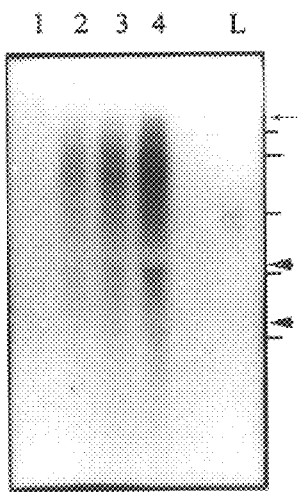
Figure 6C:
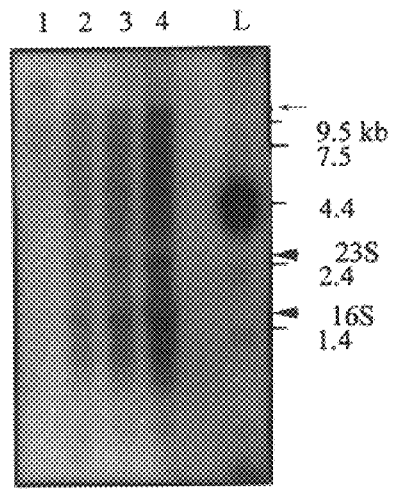

Total RNA from cells grown in the presence and absence of L-arabinose, was isolated, blotted and hybridized to three different DNA probes (Probes 1,2, and 3 of FIG. 1) each specific to one gene of the ara region (araA, araM and abfA, respectively). The Northern blot analysis (FIG. 6) revealed that the ara genes are organized in a large polycistronic operon, and that transcripts could be detected only if the cells were grown in the presence of L-arabinose. In addition to a transcript of 11 kb comprising all genes and detected with the three probes, clearly several other signals of different intensities were obtained depending on the probe used (FIG. 6). Using the araA-specific probe, we detected five different transcripts of 8.2 kb, 6.4 kb, 5.8 kb, 4 kb and 1.9 kb. Two additional transcripts of 8.2 kb and 6.4 kb were visualized with the araM-specific probe and three hybridization signals were obtained with the abfA-specific probe: 8.3 kb, 4.8 kb and 1.1 kb. These different minor transcripts might be generated by premature transcription termination of processing of the multicistronic message. Stable secondary structures were identified at the correspondent sites within the araB, araL, araN, and araQ sequences (FIG. 2).

The promoter region and transcriptional start site of the ara operon

Figure 7:
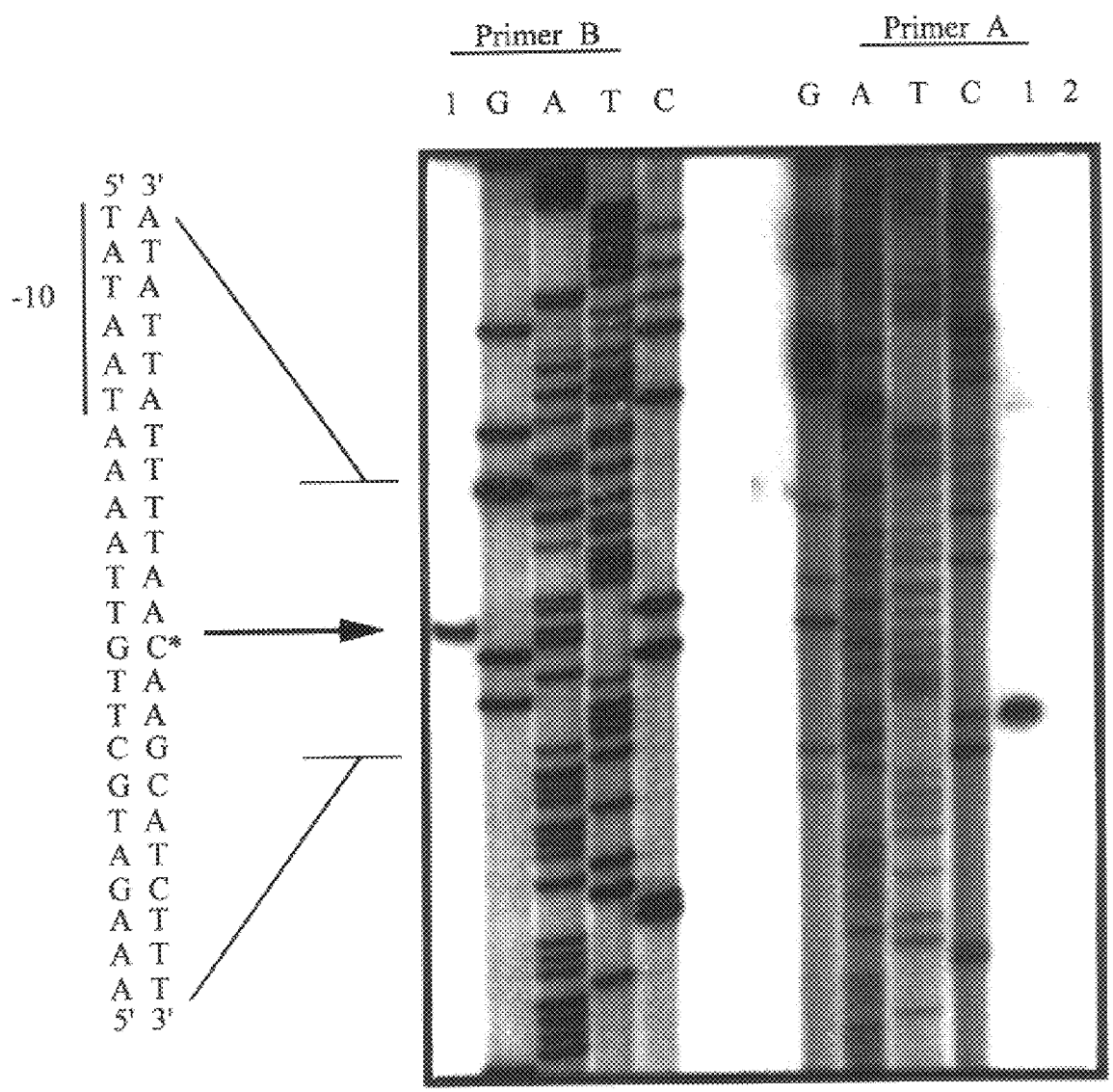
FIG. 7. Primer extension analysis of the ara operon promoter. Two radio labeled oligonucleotide primers A and B complementary to two different regions downstream from the araABD promoter: primer A (5'-GAAGCATGTAAACTGCCCC-3', SEQ ID NO:25), complementary to a region of araA mRNA located between nucleotides 216 to 234 (FIG. 2) and primer B (5'-CCAGCGTCTCTTCCCCG-3', SEQ ID NO:26), complementary to a region of the araA mRNA located between nucleotides 283 to 300 (FIG. 2), were hybridized with *B. subtilis* BR151 RNA isolated from exponentially growing cells in the presence (1) or absence (2) of L-arabinose. After extension, the products were analyzed by gel electrophoresis, together with a set of dideoxynucleotide-chain termination sequencing (SEQ ID NO:54) reactions using the same primers and a single stranded M13 DNA template which includes entire araA gene and an additional 228 bp of its 5'-flanking sequence.

To determine the transcriptional start site of the ara operon, total RNA was extracted during the exponential growth of wild type cultures in the presence and in the absence of L-arabinose. Reverse-transcripts were obtained using an end labeled 17-mer (primer b, FIG. 2), designed to hybridize to part of the mRNA coding for the araA gene, and characterized by electrophoresis (see Experimental procedures). A Single extension products was detected with RNA isolated from cells grown in the presence of L-arabinose, the size of which suggests that transcription of the ara operon starts at a G residue situate 97 nucleotides upstream from the araA start codon (FIG. 7). No extension product was seen when RNA was isolated from cell grown in the absence of L-arabinose. The same transcription start point was obtained using a second primer (primer A, FIG. 2) designed to hybridize to part of the mRNA 50 bases upstream from the first primer (FIG. 7). the synthesis of the ara operon message is induced by L-arabinose and driven by a strong promoter as evaluated by the intensity of the reverse-transcript signal obtained. Situated 7 and 30 bp upstream from the ara operon transcription start site are sequences identical to the consensus −35 and −10 regions (TTGACA −17 bp-TATAAT, SEQ ID NO:38), respectively, of promoters recognized by *B. subtilis* o-A containing RNA polymerase (Moran et al. 1982). Sequence analysis of the promoter region revealed the existence of three inverted repeats, putative operator-like sequence, in the −35 and −10 regions (FIG. 2). A potential hairpin-loop structure with a AG value of −19.2 kcal mol−1 (Tinoco et al. 1973), centered 27 bp upstream from the −35 region (FIG. 2), probably corresponds to ta transcription terminator of a gene located upstream from the cloned DNA fragment.

Expression of the ara operon is induced by L-arabinose and repressed by glucose

Figure 8A:
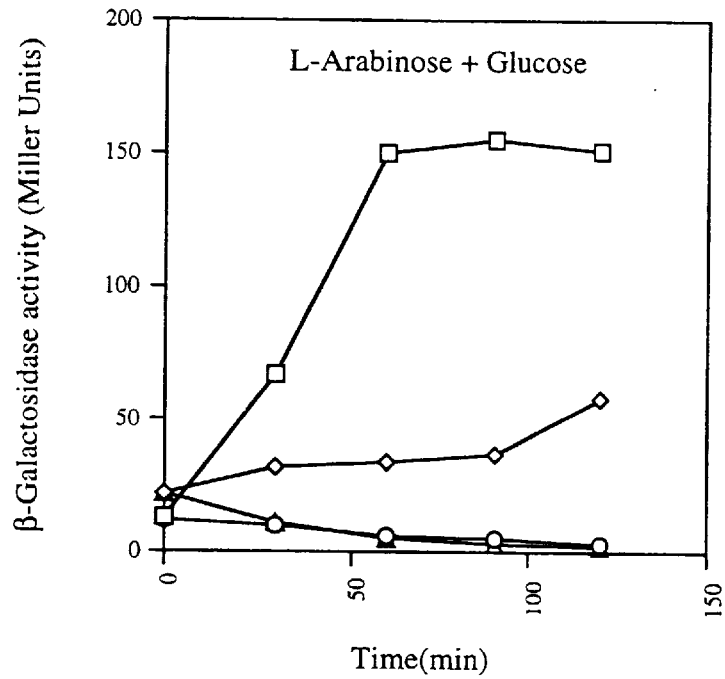
FIG. 8. Expression of the ara operon measured by determination of the levels of β-galactosidase (given as Miller units) present in exponentially growing cells, Strains of *B. subtilis* harboring transcriptional lacZ fusions were grown on C minimal medium supplemented with casein hydrolysate 1% (w/v) and either arabinose 0.4% (w/v) or arabinose 0.4% (w/v) and glucose 0.4% (w/v) (see Methods). Time is expressed in minutes after induction. ◇ IQB101 (araB'-lacZ erm Ara–Em'lacZ+); ☐ IQB103 (araa'-lacZcat Ara+ Cm'lacZ+); Δ IQB 102 (araB-erm lacZ Ara–Em'lacZ–), negative control; ○ IQB104 (araA'-catlacZ Ara+ Cm'lacZ–), negative control. For each strain the results represent the average, in Miller units, from two independent experiments.
Figure 8B:
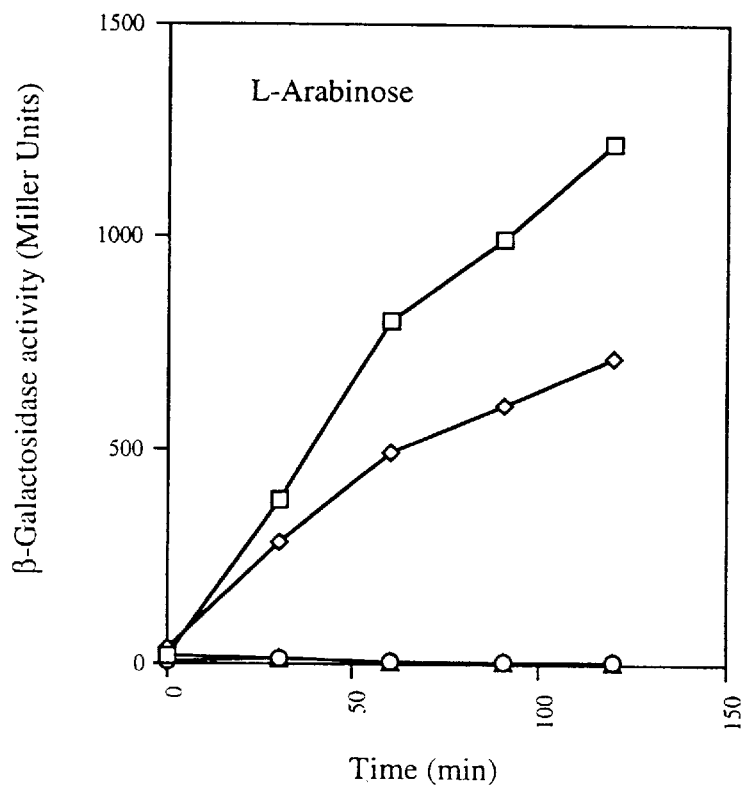

To study the regulation of expression of the operon we constructed transcriptional lacZ fusions at this locus. The replicative plasmids of pSNA11 and pSNL12 were obtained by inserting a lacZ-erm cassette marker into the araB gene in both orientations) see Experimental procedures). After linearization, the two plasmids were used separately to transform the wild type 168T+ strain, with selection Em$^r$. this resulted in the integration of the lacZ and erm genes into the chromosome at the araB locus (the exact position is depicted FIG. 1) through a double cross-over. The structure of the resulting strains, IQB101 (araB'-lacZerm) and IQB102 (araB'-erm lacZ), was confirmed by Southern hybridization (data now shown). both strains were unable to grow on L-arabinose as sole carbon source which confirmed the insertional inactivation of the araB gene. The integrating plasmids pSNL13 and pSNL14 were constructed by subcloning a 470 bp DNA fragment, which contains the 5' end of the ara transcriptional unit (FIG. 1), into pJM783 (see Experimental procedures) in both orientations. Plasmid pSNL13 contains lacZ gene in the same orientation as the araA region sequences and pSNL14 in opposite orientation. The two plasmids were used to separately to transform wild type 168T+ strain to Cm$^r$ and integrated into the chromosome by a Campbell-type recombinational event. The structure of the resulting strains, IQB103 (araA'-lacZcat) and IQB104 (ARAa'-catlacZ), was confirmed by Southern hybridization (data now shown) and because the integration was not disruptive both strains displayed an Ara+phenotype. The LacZ phenotype of the four strains was tested on minimal C medium plates supplemented with casein hydrolysate 1% (w/v) and X-Gal. Upon addition of L-arabinose to the medium, strains IQB101 and IQB 103 presented a dark blue phenotype whereas those IQB102 and IQB104 remained white, confirming that the expression of the operon is driven from a promoter located upstream from araA, and induced by L-arabinose. Furthermore, addition of other pentoses such as D-xylose and D-ribose failed to induce a LacZ+phenotype in strain IQB103. The regulation of the ara operon expression was examined in cultures during mid exponential phase growth in minimal C medium supplemented with casein hydrolysate 1% (w/v) as described in Experimental procedures. The levels and patterns of lacZ expression in IQB101 (araB,-lacZermAra−lacZ+) IQB103 (araA'-lacZcat; Ara+lacZ+); IQB102 (araB'-ermlacZ;Ara−lacZ−) negative control, and IQB104 (araA'cat-lacZ; Ara+lacZ) negative control, determined in the presence of L-arabinose and L-arabinose plus glucose are shown in FIG. 8. When the four strains were grown in the absence of inducer the level of accumulated β-galactosidase activity, at time t=20 min, were 4.4U, 4.8U, 2.8U and 1.8U (Miller units), respectively (data not shown). In the presence of L-arabinose the pattern of expression observed in strains IQN101 (araB'lacZ Ara) and IQB103 (araA'-lacZ Ara+) was very similar (FIG. 8) but the levels of accumulated β-galactosidase activity in the araB null mutant were less than 60% relatively to the wild type strain (discuss below). Addition of glucose reduced the level of expression to less than 12% in both Ara+ and Ara− backgrounds (FIG. 8). These data demonstrate that L-arabinose in an inducer which stimulates that expression of the ara operon at the transcriptional level and transcription is subjected to catabolite repression by glucose. Furthermore, the prediction that the expression of the ara operon is driven from a strong promoter, made on the basis of the intensity of the reverse transcript signal observed in primer extension analysis, was confirmed when β-galactosidase activity was measured in strain IQB103 (araA'-lacZcat Ara+).

The araL, M, N, P, Q and abfA genes are not required for L-arabinose utilization Integrational plasmids pSS2, pTN10, and pTN13, carrying fragments internal to araL, araN, and araQ genes respectively, were transformed in the wild type strain 168T+ (see above). Their integration interrupts the transcription unit at the downstream end of each fragment (FIG. 1). Transformants obtained with pSS2 and pTN10, strains IQB202 and IQB204 respectively, exhibited an Ara+ phenotype however, their growth on minimal medium plates with L-arabinose as the sole carbon source was slightly slower than the one observed with the wild type strain 168T+. This phenotype was not observed with strain IQB205 in which pTN13 disrupted the operon at the end of the araQ gene. In order to confirm that the araL, M, N, P, Q and abfA with a spectinomycin resistance cassette and then using it to replace the corresponding chromosomal sequences (see Experimental procedures). Plasmid pSN22 (FIG. 1) was linearized with SacI and used to transform the wild type strain 168T+ to resistance to spectinomycin (Sp$^r$). The resulting strain IQB206, was kanamycin sensitive which indicated that the Sp$^r$ phenotype was the result of a double-cross over event that occurred on both sides of the cassette inserted between the araL and abfA sequences (FIG. 1). This mutant strain was able to grow on minimal medium pates with L-arabinose but displayed a phenotype even more drastic than the one exhibited with strains IQB202 and IQB204. To quantify this observation we determined the specific growth rate of the deletion-insertion mutant and the wild type strain on liquid minimal C medium with L-arabinose as the sole carbon source, as described in Experimental procedures. The double time of stain IQB206 was 1.8 fold higher than the wild type strain 168T+, 193.4 min−7.2 and 107.7 min+3.6 (average of three independent experiments+standard error), respectively. These results confirmed that the genes located downstream from araD in the operon are not essential for L-arabinose utilization, however their absence in the deletion mutant affects the specific growth rate in minimal medium with L-arabinose as the sole carbon source when compared to the wild type (discuss below).

Discussion

The present work describes a new catabolic operon involved in the utilization of L-arabinose in *B. subtilis*, which we designated ara. The arabinose metabolic genes araA, araB and araD coding for L-arabinose isomerase, L-ribulokinase and L-ribulose 5-phosphate 4-epimerase, respectively, were previously cloned and by complementation experiments the products of the araB and araD genes shown to be functionally homologous to their *Escherichia coli* counterparts (Sá-Nogueira & Lencastre, J Bacteriol 171:4088–4091, 1989). These genes, whose inactivation leads to an Ara-phenotype, were found to be the first three open reading frames of a nine cistron transcriptional unit whose total length is 11 kb. To our knowledge this operon is the largest catabolic operon described in *B. subtilis*. As expected from the occurrence of genetic complementation, the deduced products araA, araB, and araD, from *B. subtilis* display a very high level of identity to the corresponding enzymes from *E. coli* and *S. thyphimurium*, which indicates that this metabolic pathway was fundamentally conserved during evolution. In *B. subtilis* the metabolic gene order, araABD, coincide with the order of the enzymatic steps carried out by the proteins that they encode for. This order is different from the one found in the operons of Enterobacteriaceae members *E. coli* and *S. thyphimurium*, araBAD, so it seems that the three genes did not act as a unitary block in the evolution of the abacterial ara genes.

The six ORFs found downstream from the araD gene, here named araL, M, N, P, Q and abfA, are not required for L-arabinose utilization. This was shown in a mutant strain IQB206 bearing a deletion, in the region downstream from the araD, comprising all genes. The function of araL and araM is unknown. The putative product of araM did not show any significant similarity with other bacterial proteins of known function and the weak similarities displayed by araL did not suggest any particular function. Interestingly the amino terminal sequences of araL share an identity of 18.7% over 193 residues with the C terminal sequences of araM (data now shown). The primary sequences of the products of the araN, araP, and araQ genes strongly suggest that they have a similar function to that of a super family of membrane-bound nutrient transport systems (Higgins et al., J. Bioenerg. Biomemb. 22:571–592 (1990)). Sequence similarities to known import proteins and the organization of the genes in the operon revealed the presence of three components from these transport systems. First, the amino terminus of araN has a predicted signal peptide and sequences typical of Gram-Positive lipoprotein (IAGCSA (SEQ ID NO:45), starting at amino acid 19, FIG. 2). We therefore suggest that araN might be anchored to the cytoplasmic membrane via an amino-lipid group (Gilson et al., Mycoplasma EMBO J. 7:3971–3974 (1988) and Perego et al., Biochemistry, Physiology and Molecular Genetics 645–624 (1991)). Second araP and araQ gene products, as other characterized integral cytoplasmic membrane proteins have hydropathy profiles which are virtually super impassable and some of their residues are apparently conserved (FIG. 5). Finally, araN, araP, and araQ belong to the same operon and the ligand-specific binding protein, araN, is encoded by the promoter-proemial gene, a situation common to these systems. In *B. subtilis* the phosphotransferase system is not involved in the transport of L-arabinose into the cell (Gay et al. Mol. Gen. Genet. 121:355–368 (1973), therefore it is tempting to propose that araN, araP and araQ are components of a high affinity transport system for L-arabinose. However, no evident ATP-binding protein connected with energy coupling of the transport system was found in the operon.

The transport of L-arabinose across *E. coli* cytoplasmic membrane requires the expression of either the high-affinity transport operon, araFGH a binding protein-dependent system (Brown and Hogg et al., J. Bacteriol 111:606–613 (1972); Horazdowvsky and Hogg et al., J. Bacteriol 171:3053–3059 (1989); Kolodrubetz and Schleif, et al., J. Bacteriol 148:472–479 (1981)) or the low-affinity transport operon, araE a proton synporter (Novotny and Englesberg, et al., Biochim. Biophys. Acta. 117:217–230 (1996). The existence of two parallel uptake systems thwarts usual genetic attempts at isolation of mutants defective in either of the transport systems. The Ara+ phenotype displayed by the *B. subtilis* deletion mutant strain IQB206 (▲araL-abfA::spc) together with the 1.8 fold increase in the doubling time observed on liquid minimal medium with L-arabinose as the sole carbon source, relatively to the wild type strain, is typical of a transport mutant when the microorganism has alternative transport systems for the same substrate. Interestingly, the primary structure of AraP and AraQ showed each similarity with AraH, the integral cytoplasmic membrane protein from *E. coli*, and the same result was observed between AraN and ARaF, the *E. coli* arabinose binding protein (data now shown). Furthermore, on the basis of their signature sequences AraN, AraP and AraQ can be included in the disaccharide sub-cluster (FIG. 4 and FIG. 5) together with proteins involved in the high-affinity transport of malto-oligosaccharides and multiple sugars. In connection, *B. subtilis* secretes three enzymes involve in degradation of L-arabinose polymers, an endo-arabanase and two arabinosidases, and the purified endo-arabanase was shown to be capable of releasing arabinosyl oligomers from plant cell walls (Kaji and Saheki et al., Biochim. Biophys. Acta. 410:354–360 (1975); Weinstein and Albersheim, et al., Physiol. 63:425–432 (1979)); these observations are suggestive of a wider substrate range for the *B. subtilis* AraN binding protein. The last gene of the ara operon, abfA, based on the strong similarity observed between the primary structure of its putative product and other bacterial arabinosidases, most probably codes for the α-L-arabinofuranosidase purified and described by Weinstein and Albersheim et al., Physiol. 63:425–432 (1979).

Expression of the ara operon is induced by L-arabinose and driven by a strong promoter located upstream the araA gene. This has been demonstrated in this study by Northern blot experiments and primer extension analysis. Examination of the ara operon promoter reveals −35 and −10 sequences, relative to its transcriptional start site (show in FIG. 2), separated by an optimal spacing of 17 bp identical to the consensus sequences derived from the analysis of many δA dependent promoters (Moran et al., Mol. Gen. Genet. 186:339–346 (1982)). These sequences were shown to be important for the interaction of δA with their cognate promoters (reviewed in Moran 1993 653–667). The presence of a strong promoter raises the possibility that transcription of ara is negatively regulated like in other well characterized B. subtilis catabolic operons, such as xyl (Gärtner et al., Mol. Gen. Genet. 232:415–422 (1992) gnt (Fujita and Fujita, Proc Natl Acad Sci USA 84:4524–4528 (1987); Miwa and Fujita, J. Biol. Chem. 263:13252–13257 (1988); in fact the product of the araC gene recently cloned, is negative regulator of the ara operon (Sá-Nogueira and Mota, unpublished). To characterize the regulation of ara expression in greater detail we constructed transcriptional fusions of the ara promoters to the E. coli lacZ gene in Ara+ and Ara− strains. The induction by L-arabinose in strain IQB103 (araA-lacZ Ara−) and IQB103 (araA'-lacZ Ara+) was very similar. Interestingly however, the levels of accumulated β-galactosidase activity in IQB101 (araB'-lacZ Ara−) were less than 60% of the fully induced level in wild type starting. Since in this strain the ara transcription unit is interrupted at the level of the araB gene (FIG. 1), and a role in the transport of L-arabinose was proposed for the downstream genes araN, araP, and araQ this effect cold be due to less accumulated intracellular L-arabinose which prevents fully expression of the ara promoter. Another possible explanation is that the products of the araL and araM genes could stimulate transcription from the ara promoter. Addition of glucose reduced the level of expression to less than 12% in both Ara+ and Ara− backgrounds indicating that repression of the ara operon by glucose acts at the transcriptional level.

Although the regulatory system mediating catabolite repression in B. subtilis is unknown there is some evidence that it is accomplished by a negative regulatory mechanism (reviewed in Chambliss, 1993, 213–219; Hueck and Hillen, Mol. Microbiol. 15:395–401 (1995); Saeir et al., Microbiology 142:217–230 (1996). This evidence is based on the location and sequences of cis-acting sites (CREs) responsible for catabolite repression of several B. subtili genes and operons (Weickert & Chambliss, Proc. Natl. Acad. Sci. USA 87:6238–6242 (1990); Chambliss, (1993), 213–219; Hueck and Hillen, Mol. Microbiol. 15:395–401 (1995). Moreover, catabolite repression of most genes regulated via these cis-acting sites is also affected by the trans acting factors CcpA and Hpr (reviewed in Hueck and Hillen, Mol. Microbiol. 15:395–401 (1995) and Saeir et al., Microbiology 142:217–230 (1996). Sequence analysis suggests that CcpA is a DNA-binding protein but it is not known whether CcpA is directly involved in the mechanism of catabolite repression (Chambliss, 1993, 213–219; Fujita & Miwa, J. Bacteriol 176:511–513 (1994). Hpr, an intermediate in the PTS sugar transport system, of several Gram-positive bacteria can be phosphorylated at a serine residue at position 46 by an ATP-dependent kinase which is activated in the presence of fructose-1,6-diphosphate (FDP) (Deutsch and Saier, Proc. Natl. Acad. Sci. USA 62:1100–1107 (1983); Reizer et al., J. Cell. Biochem. 51:19–24 (1993). Experiments with B. subtilis strains carrying a mutation which unable phosphorylation of Hpr at position 46, showed that catabolite repression of various operons was relieved (Deutscher et al., J. Bacteriol 176:3336–3344 (1994). It has been proposed that Hpr-ser-P might interact with CcpA and that this interaction might allow CcpA to bind to the CRE (Deutscher et al., J. Bacteriol 176:3336–3344 (1994). Strong evidence to this proposal was obtained by Deutscher et al., Mol. Microbiol 15:1049–1053 (1995), by showing that Hpr-ser-P of B. subtilis can bind to CcpA of B. megaterium, in vitro DNA-binding experiments conducted by Kim et al., J. Bacteriol 1775129–5134 (1995), showed that B. subtilis CcpA protein binds specifically and with high affinity to the CRE in the amyO control region in the absence of Hpr-ser-P. Ramseier et al., Microbiol Lett. 129:207–214 (1995), observed binding of B. megaterium CcpA to the CRE of the xyl operon of B. subtilis at low protein concentrations and showed that Hpr-ser-P diminished the extent of binding. Different results were obtained by Fujita et al., Mol. Microbiol 17:953–960 (1995), with the gnt operon. The authors observed that specific binding of B. subtilis CcpA to the CRE of this operon required the presence of Hpr-ser-P. CREs of catabolic genes and operons are located either in the promoter regions, where the binding of a resultatory protein probably interferes with transcription initiation, or in the downstream regions (reviewed in Hueck and HIllen, Mol. Microbiol. 15:395–401 (1995). The latter genes and operons also contain sequences with each similarities to CRE overlapping the respective promoters. Miwa and Fujita, J. Biochem 113:665–671 (1993) have proposed that catabolite repression of the gnt operon might utilize a transcriptional blockage mechanism. In the case of the hut operon two active CREs were found, one at the promoter and the other within the hutP gene, and a looping mechanism involving cooperatively bound CREs has been proposed to interfere with transcription initiation (Wray et al., 1994). Furthermore, the transition-state regulator AbrB is capable of specifically binding to hut CRE in vitro and an abrB null mutation leads to more efficient\catabolite repression of some genes in B. subtilis, including L-arabinose isomerase. Thus, AbrB has been suggested to complete for binding to CRE with CcpA (Fisher et al., J. Bacteriol 176:1903–1912 (1994). The promoter region of the ara operon contain a sequence very similar to the CRE consensus sequence (TGWNANCGNTNWCA, SEQ ID NO:8; W=A,T) located between the between the transcription start site and the translation start site of the araA (position 191 to 204, FIG. 2). A second sequence, which shows weak similarity with the CRE consensus sequence was found within the araA gene (position 260 to 273, FIG. 2). Since inducer exclusion does not play a major role in carbon regulation of expression of the ara metabolic genes (Sá-Nogueira & Lencastre, Bacillus subtilis J Bacteriol 170:2855–2857 (1988), as it was observed in the hut operon (Chasin and Magasanik, J. Biol. Chem. 243:5165–5178 (1968), it will thus be interesting to investigate the role of CcpA, Hpr, and AbrB, in the catabolic repression of the ara operon and whether these sequences are cis-acting sites responsible for catabolic repression of the ara genes.

Experimental procedures

Bacterial strains and growth conditions

The B. subtilis strains used in this study are listed on Table 2. E. coli DH5α (GIBCO BRL, Life Technologies European Division) was used as a host for all plasmids and E. coli DH5α (BRL) for the propagation and amplification of recombinant M13 bacteriophages. E. coli strains were grown on LB (Luria-Bertani medium; Miller, (1972). Ampicillin (75 μg ml−1), or IPTG (isopropyl β-thiogalactopyranoside, 1 mM) were added as appropriate. B. subtilis strains were grown on LB (Luria-Bertain medium; Miller (1972), SP medium (Martin et al., Mol. Gen. Genet. 208:177–184 (1987), or C minimal medium (Pascal et al., Biochem 53:1059–1066 (1971). Chloramphenicol (5 μg ml−1)m erythromycin (1 μg ml−1), kanamycin (25 μg ml−1) or spectinomycin (50 −g ml−1) were added as appropriate. Solid medium was made with LB, SP or C medium contain 1.5% (w/v) Bacto Agar (Difco). To test for growth of B.

*subtilis* integrant strains on L-arabinose as sole carbon source, strains were plated on minimal C medium plates supplemented with casein hydrolysate 1% (w/v). L-arabinose 0.1% (w/v) and ribitol 1% (w/v). To determine the specific growth rates, the *B. subtilis* strains were grown in liquid C medium with L-arabinose 0.4% (w/v) as sole carbon source. The cell cultures were incubated in a water shaker (Aralab, Equipamentos de Laboratorio Lda, Oeiras, Portugal) with aeration by shaking 130 rpm and the cell growth was monitored in a UltrospecIII spectrophotometer (Pharmacia LKB Biochrom Ltd. Cambridge, England) as A600. For the β-galactosidase assays and the RNA preparation the *B. subtilis* strains were grown in liquid C medium supplemented with casein hydrolysate 1% (w/v) and L-arabinose and glucose were added to the cultures when necessary at a final concentration of 0.4% (w/v).

Plasmid constructions

Plasmid pSNL7 was constructed by subcloning a 959 bp Smai-Pst DNA fragment (nucleotide 938 to 1897, FIG. 1) from pSNL1 (Sá-Nogueira & Lencastre, *Bacillus subtilis* J Bacteriol 170:2855–2857 (1988) between the Smali and PstI sites of the integrational vector pJM783 (Perego, Mol. Microbiol. 6:173–185 (1983). This step inactivates the ampicillin resistance gene (Amp$^r$) of the vector and selection in *E. coli* was made for chloramphenicol resistant (Cm$^r$). Plasmid pSNL9 was obtained by cutting chromosomal DNA from *B. subtilis* IQB100, in which pSNL7 had integrated into the araB region by a single crossover (Campbell-type) recombination event (FIG. 1), with HindIII, followed by circularization of this DNA at low concentration. This ligation mixture was transformed into *E. coli*, and Cm$^r$ transformants were selected as described above. To construct plasmid pSS2, we digested pSNL1 (Sá-Nogueira & Lencastre, *Bacillus subtilis* J Bacteriol 170:2855–2857 (1989) with HIndIII and XholI and cloned a purified fragment of 965 pb (nucleotide 3815 to 4780, FIG. 1) between the HIndIII and SalI sites of the integrating vector pJH101 (Ferrari et al., J. Bacteriol 154:1531–1515 (1983). Plasmid pSS3 was constructed by digestion of chromosomal DNA from *B. subtilis* IQB202, in which pSS2 had integrated into the araL region by a single crossover (Campbell-type) recombination event (FIG. 1), with EcoRI, followed by circularization of this DNA at low concentration. This litigation mixture was transformed into *E. coli*, and Ap$^r$ transformants were selected as described above. Subcloning of the 789 pb HindIII-HincII DNA fragment (nucleotide 6545 to 7334, FIG. 1) from pSS3 between the HindIII and EcoRV sites of the integrational vector pJH101 (Ferrari et al. J. Bacteriol 154:1531–1515 (1983) yielded plasmid pTN10. Plasmid pTN13 was obtained by the same procedure described for pSS3 after digestion of chromosomal DNA from *B. subtilis* IQB204, in which pTN10 had integrated into the araN region by a single crossover (Campbell-type) recombination event (FIG. 1) with NcoI. Plasmid pTN14 was constructed by subcloning the 678 pb SmaI-BglII DNA fragment (nucleotide 8242 to 8920, FIG. 1) from pTN13 between the BamHI and SstI (fill-in) sites of pJM783 (Perego, biochemistry, physiology and molecular genetics 645–624 (1991). To construct pSN5 the same methodology used to obtain pSS4 and pTN13 was applied, after cutting chromosomal DNA from *B. subtilis* IQB205, in which pTN14 had integrated into the araQ region by a single crossover (Campbell-type) recombination event (FIG. 1) with SmaI. Subcloning the 1.7 kb EcoRI-HincII fragment (nucleotide 2681 to 4416, FIG. 1) from pSNL1 (S á-Nogueira & Lencastre, *Bacillus subtilis* J Bacteriol 170:2855–2857 (1989) between the EcoRI and SmaI sites of pMK4 (Sullivan et al., Gene. 29:21–26 (1984), yielded plasmid pSNL10. PlasmidspSNL11 and pSNL12 were obtained as follows. A 4.5 kb BamHI-HindIII fragment extracted from pMC11 (Debarbouillé et al., J. Bacteriol 172:3966–3963 (1990), containing the lacZ and erm genes from pTV32 (Perkins & Youngman, Acad. Sci. USA 83:140–144 (1991), was purified, made blunt with the "Klenow fragment" of DNA polymerase I and then subcloned in both orientations at the unique EcoRV restriction site (nucleotide 3214, FIG. 1) of pSNL10. pSNL11 contains the lacZ gene in the same orientation as the EcoRI0EcoRV araB fragment (nucleotide 2681 to 3214, FIG. 1), which was confirmed by DNA sequencing, and pSN112 in opposite orientation. Subcloning a 470 bp DraI-EcoRVDNA fragment (nucleotide 82 to 552, FIG. 1) from pSNL9 at the unique SmaI site of the integrational vector pJM783 (Perego, biochemistry, physiology and molecular genetics 645–624 (1991), in both orientations, yielded plasmids pSNL13 and pSNL14. pSNL13 contains the lacZ gene in the same orientation as the araA region sequences, which was confirmed by DNA sequencing, and pSNL14 in opposite orientation. Plasmid pSN20 was construct by the 1.2 kb EcoRV-HincII fragment (nucleotide 3214 to 4416, FIG. 1) from pSS4 into the SmaI site of pAH248 (see above). Subcloning of the 1.7 kb EcoRV fragment from pSN5 (nucleotide 10632 to about 12332, FIG. 1) into the HincII site of plasmid pAH250 (see below) yielded plasmid pSN21. Plasmid pAH248 (a gift from A. O. Henries and C. P. Moran Jr.) is a pGem7-zf(+) (Promega Corporation, Madison, USA) derivative that contains a kanamycin resistance gene cloned between its XhoI and EcoRI sites. Plasmid pAH250 (Henriques, A. O., B. W., Beall and C. P. Moran Jr., unpublished) is a pBlueprint SK(+) (Stratagene, LaJolla Calif., USA) derivative that contains a specitnomycin resistant gene cloned between its EcoRV site. To construct pSN22, we digested pSN20 with PstI and NsiI and cloned a purified fragment of about 2790 bp, which contains the kanamycin resistance gene, between the SmaI site of pSN21.

DNA manipulations and sequencing

DNA manipulation was carried out according to Sambrook et al. (1989). Enzymes were purchased from commercial suppliers and used according to the manufacturers' instructions. DNA sequencing was performed by the method of Sanger et al., Proc. Natl. Acad. Sci. USA 74:140–144 (1977) with the Sequenase Kit (T$_7$ DNA polymerase; United States Biochemical Corporation, USB). Sequencing templates were prepared by a combination of subcloning appropriate fragments from pSNL1 and PSNL9 into the polycloning site of M13mp19 or M13mp18 (Yanisch-Perron et al., Gene 33:103–119 (1985) and sequential deletion of the recombinant M13 derivatives, by the method of Dale et al., Plasmid 13:31–40 (1985), using the Cyclone Biosystem Kit (IBI, International Biotechnologies, Inc.). The DNA sequence was determined on both strands and across all the restriction sites used for subcloning. The primer 5'-CCTCTTCGCTATTACGC-3' (SEQ ID NO:46), complementary to the coding sequences of the LacZ gene was used to sequence the transcriptional LacZ fusions.

Bacterialtransformation

*B. subtilis* DNA transformations were performed according to the method of Anagnostopoulos & Spizizen (1961). *E. coli* transformations were carried out according to standard methods (Sambrook et al., 1989).

β-Galactosidase assays

Strains of *B. subtilis* harboring transcriptional lacZ fusions were grown on 75 ml of C medium supplemented with casein hydrolysate 1% w/v. During each logarithmic phase, optical density at 600 nm (OD$_{600}$) of 0.11–0.15, 25 ml of the culture were transferred to two different flasks, 25 ml to each flask, and L-arabinose at a final concentration of 0.4% (w/v) was added to one of the cultures and to the other L-arabinose and glucose at a final concentration of 0.4% (w/v) was added to one of the cultures and to the other L-arabinose and glucose at a final concentration of 0.4% (w/v) were added. At this time, To, a 100 μl aliquot of cell culture were collected, harvested and stored at −70° C. overnight. Exponential growth of the three cultures was followed by measuring absorbance and at 30 min intervals 100 μl of cell culture samples were removed, treated as described above, until the cultures reached an $OD_{600}$= 0.7–0.8, which corresponds to growth for at least 2.5 generations in the presence of the inducer. The cells were suspended in 1 ml of Z buffer (Miller, 1972), and 2 drops of chloroform and 1 drop of 0.1% sodium dodecyl sulfate were added and mixed vigorously for 10 s on a tabletop vortex apparatus. The β-Galactosidase activity was determined as described by Miller (1972) using the substrate o-nitrophenyl-β-D-galactopyranoside (ONPG).

RNA preparation, northern blot and primer extension analysis

B. subtilis 151 cells or B. subtilis 168T+ were grown in C medium supplemented with 1% (w/v) casein hydrolysate in the presence and in the absence of L-arabinose at a final concentration of 0.4% (w/v). Cells were harvested during late logarithmic phase of growth. $OD_{600}$ approximately 0.9, and RNA prepared essentially as described by Igo et al., J. Mol. Biol. 191:615–624 (1986). For Northern blot analysis, 2.5–10 μg of total RNA was run in agarose/formaldehyde 1.0–1.2% (w/v) and transferred to positively-charge nylon membranes Hybond-N+ (Amersham International, UK) according to standard methods (Sambrook et al. 1989). A size determination was done by using an RNA ladder (9.5–0.24 kb; Gibco/BRL). The probes were labeled using the Multiprime random oligonucleotide DNA labeling system obtained from Amersham and [α-$^{32}$P]dATP (3,000 Ci/mmol). Primer extension analysis was performed essentially as described in Sambrook et al., (1989) using 25 μg of total RNA. The two synthetic oligonucleotides used in primer extension experiments were: primer A (5'-GAAGCATGTAAACTGCCCC-3', SEQ ID NO:25) a 19-mer, complementary to a region of araA mRNA located between nucleotides 216 to 234 (FIG. 2) and primer B (5'-CCAGCGTCTCTTCCCCG-3', SEQ ID NO:26) a 17-mer, complementary to a region of the araABD mRNA located between nucleotides 283 to 300 (FIG. 2). The two oligonucleotides were used in separate experiments to rule out the possibility of primer-specific artifacts. A total of 10 ng of primer was used in the labeling reaction and mixed with 25 μg of RNA, denatured by heating to 85° C. for 10 min and annealed by incubation at 42° C. for 3 h. The oligonucleotide primer was extended by using 15 units of avian myeloblastosis virus reverse transcriptase for 2 h at 37° C., as described by Sambrook et al., (1989). Analysis of the extended products was carried out on 7.5% polyacrylamide urea gels.

Computer analysis

Amino acid sequences were deduced from the nucleotide sequence using DNASIS V2.0, Hitachi Software Engineering Co., Ltd., 1991. The GenBanK and EMBL databases were assessed using the Genetics Computer Group (GCG) package of sequence analysis software (Genetics Computer Group, Inc., Madison, Wis.).

Nucleotide sequence accession number

The DNA sequence reported here have been submitted to the GenBanK database and assigned numbers X89408 (araA, araB and araD genes) and X89810 (araL, araN, araP, araQ and abfA genes).

TABLE 1

Percentage of amino acid identity between the predicted sequences of the Ara proteins and their similar proteins

| B. subtilis Ara proteins | Homologue (species)[a] | Function | Percentage Identity | Amino acid overlap |
|---|---|---|---|---|
| AraA | AraA (E. coli) | L-Arabinose isomerase | 52.9 | 495 |
| | AraA (S. typhimurium) | L-Arabinose isomerase | 52.9 | 495 |
| AraB | AraB (E. coli) | L-Ribulokinase | 25.7 | 552 |
| | AraB (S. typhimurium) | L-Ribulokinase | 30.6 | 350 |
| AraD | AraD (E. coli) | L-ribulose-P 4-epimerase | 57.1 | 231 |
| | AraD (S. typhimurium) | L-ribulose-P 4-epimerase | 58.0 | 205 |
| AraL | NagD (E. coli) | Unknown | 25.5 | 251 |
| AraN | LacE (A. radiobacter) | Lactose-binding protein | 26.2 | 302 |
| | MalX (S. pneumoniae) | Maltose-binding protein | 24.1 | 345 |
| | AmyE (T. thermosulfurigens) | Starch-binding protein | 21.7 | 369 |
| AraP | LacF (A. radiobacter) | Membrane protein | 29.6 | 284 |
| | UgpA (E. coli) | Membrane protein | 26.2 | 286 |
| | AmyD (T. thermosulfurigens) | Membrane protein | 25.4 | 284 |
| | MalC (S. pneumoniae) | Membrane protein | 25.2 | 298 |
| AraQ | LacG (A. radiobacter) | Membrane protein | 32.7 | 254 |
| | UgpE (E. coli) | Membrane protein | 22.9 | 279 |
| | AmyC (T. thermosulfurigens) | Membrane protein | 28.2 | 262 |
| | MalD (S. pneumoniae) | Membrane protein | 25.6 | 262 |
| AbfA | AbfA (S. lividans) | α-L-arabinofuranosidase | 52.6 | 500 |

[a]AraA, AraB and AraD from E. coli [Lee et al., (1986)]; ArA, AraB and AraD from S. typhimurium [Lin et al., (1985a); Lin et al., (1985b); Lin et al., (1985c)]; LacE, LacF and LacG from Agrobacterium radiobacter [Williams et al., (1992)]; AmyE, AmyC and AmyD from Thermoanaerobacterium thermosulfurigens [Bahl et al., (1991); Sahm et al., 1996];UgpA and UgpE from E. coli [Overduin et al., (1988)]; MalX, MalC and MalD from Streptococcus pneumoniae [Puyet and Espinosa (1993)]; AbfA from Streptomyces lividans [Manin et al., (1994)]; NagD from E. coli [Plumbridge, (1988)].

TABLE 2

B. subtilis strains

| Number | Genotype | Phenotype | Source |
|---|---|---|---|
| 168T$^+$ | prototroph | Ara$^+$ | F. E. Young |
| BR151 | metB10 lys3 trpC2 | Ara$^+$ | F. E. Young |
| IQB100 | araB'::pSNL7(araB-cat lacZ) | Cm$^r$Ara$^-$ | pSNL7 → 168T$^+$ |
| IQB101 | araB'::lacZerm | LacZ$^+$MSL$^r$Ara$^-$ | pSNL11$^{(a)}$ → 168T$^+$ |
| IQB102 | araB'::erm lacZ | LacZ$^-$MSL$^r$Ara$^-$ | pSNL12$^{(a)}$ → 168T$^+$ |
| IQB103 | araA'::pSNL13 (araA-lacZ cat) | LacZ$^+$Cm$^r$Ara$^-$ | pSNL13 → 168T$^+$ |
| IQB104 | araA'::pSNL14 (araA-cat lacZ) | LacZ·Cm$^r$Ara$^+$ | pSNL14 → 168T$^+$ |
| IQB202 | araL'::pSS2 (araL-amp cat) | Cm$^r$Ara$^+$ | pSS2 → 168T$^+$ |
| IQB204 | araN'::pTN10 (araN-cat amp) | Cm$^r$Ara$^+$ | pTN10 → 168T$^+$ |
| IQB205 | araQ'::pTN14 (araQ-lacZ 'cat) | LacZ-Cm$^r$Ara$^+$ | pTN14 → 168T$^+$ |
| IQB206 | ΔaraL-abfA::spc | Sp$^r$Ara$^+$ | pSN22$^{(a)}$ → 168T$^+$ |

All strains are derivatives of B. subtilis 168T$^+$. The arrows indicate transformation and points from donor DNA to recipient strain. The DNA structure of the ara operon region in all strains is represented in FIG. 1. (a) indicate that the transformation was carried out with linearized plasmid DNA.

Example 2

Study of the Bacillus subtilis L-Arabonose Operon

Introduction

The primary sequence of the products of the genes L-arabinose isomerase, L-ribulokinase and L-ribulose 5-phosphate 4-epimerase respectively, showed strong similarity to the corresponding enzymes of Escherichia coli and Salmonella typhimurium. Transcription of this operon initiates from a σA-like promoter upstream from the araA gene and is inducible by L-arabinose and repressed by glucose.

Materials and Methods

Unless otherwise stated, the materials and methods used were those described in the Experimental procedure section of Example 1.

TABLE 3

Plasmids Used

| Plasmids | Genotypes | Reference |
|---|---|---|
| pMK$_4$ | Amp$^R$Cm$^R$ | Sullivan et al., 1984 |
| pMC11 | Amp$^R$lacZerm | Debarbouillé et al., 1990 |
| pJM783 | Amp$^R$Cm$^R$ | Perego and Hoch, 1988 |
| pSNL1 | Amp$^R$Cm$^R$araA'araB araD (insert fragment of 4.8Kb in pMK$_4$) | Sá-Nogueira and Lencastre, 1989 |

Materials—Restriction endonucleases were obtained from Amersham, New England Biolabs Inc. and Bethesda Research Laboratories. T4 DNA ligase, the "Klenow fragment" of DNA polymerase I, and S1 Nuclease were from Amersham; Polynucleotide Kinase was from New England Biolabs Inc.; AMV Reverse Transcriptase was from Bethesda Research Laboratories. All the enzymes were used as specified by the manufacturers. $^{32}$P and $^{35}$S-labeled nucleotides were from Amersham. The SEQUENASE kit (T$_7$ DNA polymerase; U.S. Biochemical Corp.) was used for DNA sequencing reactions. The method of Dale [Dale et al., Plasmid, 13:31–40 (1985)], using the Cyclone Biosystem Kit (International Biotechnologies Inc.), was applied to obtain overlapping deletions for DNA sequencing. Purified custom synthesized oligonucleotides were from SYMBIO-COM.

Transformation and Selection—B. subtilis and E. coli strains were transformed essentially as previously described [Yasbin et al, J. Bacteriol, 113:540–548 (1973); Ausubel et al., In Current Protocols in Molecular Biology, Ed. Green Publishing Associates and Wiley Interscience, (1987–1988)]. Selection of E. coli transformants was performed on Luria plates containing ampicillin 50 μg/ml or chloratnphenicol 2.5 μg/ml. B. subtilis chloramphenicol resistant transformants (Cm') were selected on SP or Luria agar plates containing Cm 5 μg/ml. When the marker to be selected in B. subtilis was MLS$^r$ (Macrolides, Lincosamides and Streptogramin B resistance), after DNA transformation, yeast extract (10 mg/ml) and casein hydrosolate (10 mg/ml) were added and incubation with shaking at 37° C. was continued in the presence of erythromycin (0.1 μg/ml) in order to induce the erm gene. Transformants were selected on SP or Luria plates containing lincomycin (25 μg/ml) and erythromycin (1 μg). The Lac+ phenotype of B. subtilis was scored on C agar plates supplemented with 1% (w/v) casein hydrolysate and 0.4% (w/v) L-arabinose or 0.4% (w/v) glucose, containing X-gal 200 μg/ml (5-bromo-4-chloro-3-indolyl-β-D-galactopyranoside).

DNA Manipulation—Plasmid DNA was extracted by the alkaline lysis method [Biarboim and Doly, Nucleic Acids Res., 7:1513–1523 (1979)] followed by ultracentrifugation in CsCl ethidium bromide gradient or Polyethyleneglycol precipitation as described [Sambrook et al., In Molecular cloning: a Laboratory Manual, 2nd edn., Cold Spring Harbor, N.Y.: Laboratory, Cold Spring Harbor Laboratory (1989)]. B. subtilis chromosomal DNA extraction was performed as previously described [Ferrari et al., J. Bacteriol., 152:782–785 (1982)].

Plasmids pSNL8 and pSNL9 were constructed as described by P. Youngman [Weinstein and Albersheim, Plant Physiol., 63:425–432 (1979)]. Chromosomal DNA of strain IQB100, resulting from the integration of pSNL7 into the chromosomal DNA of B. subtilis 168T$^+$, was restricted by either Eco RI or Hind III and self ligated at low concentrations.

DNA Sequencing—The DNA sequence was determined by the dideoxy termination method [Perkins and Youngman, Proc Natl Acad Sci USA, 83:140–144 (1986)] with α[$^{35}$S] dATP (specific activity:>1000 Ci/nmol; Amersham). Several fragments from pSNL1, pSNL8 and pSNL9 were subcloned into the polycloning site of RFM13mp19 or RFM13mp18 and the DNA sequenced on both strands by the strategy of Dale et al. [Dale et al., 1985, supra]. Sequencing reactions were performed with modified T7 DNA polymerase (Sequenase) by using M13 templates and the M13 universal primer. The sequencing reaction products were resolved on 6%–8% polyacrylamide-8M urea gels and run at 1500–1700 V. Gels were exposed to Hyperfilm™-β max (Amersham).

Reverse Transcriptase Mapping of the 5'-End of ara mRNA—The method used was essentially as described by Sambrook et al. (Sambrook, J. et al., 1990) using 25 µg RNA. The two synthetic oligonucleotides used in primer extension experiments were: primer A (5'-GAAGCATGTAAACTGCCCC-3') (SEQ ID NO:25) 19-mer, complementary to a region of araA mRNA located between nucleotides 216 to (FIG. 3) and primer B (5'-CCAGCGTCTCTTCCCCG-3') (SEQ ID NO:26) 17-mer, complementary to a region of the araA mRNA located between nucleotides 283 to 300 (FIG. 3). Both primers were $^{32}$P-labelled with polynucleotide kinase forward reaction as described (Sambrook, J. et al., 1990). The two oligonucleotides were used in separate experiments to role out the possibility of primer-specific artifacts. A total of 10 ng were used in the labelling reaction and mixed with 25 µg of RNA, denaturated by heating to 85° C. for 10 minutes and annealed by incubation at 42° C. for 3 hours. The oligonucleotide primer was extended by using 15 units of avian myeloblastosis virus reverse transcriptase for 2 hours at 37° C., as described (Sambrook, J. et al., 1990). Analysis of the extended products was carried out on 7.5% polyacrylamide urea gels.

Computer Analysis of DNA Sequences—Nucleotide sequences were analyzed by SEQNCE Program, Delaney Software Ltd., Vancouver, Canada. The alignments of araA, araB and araD predicted amino acid sequence were performed by the FASTA algorithm [Pearson and Lipman, *Proc. Natl. Acad. Sci. USA*, 85:2444–2448 (1988)].

Results

Nucleotide Sequence of the ara Genes

Figure 9B:
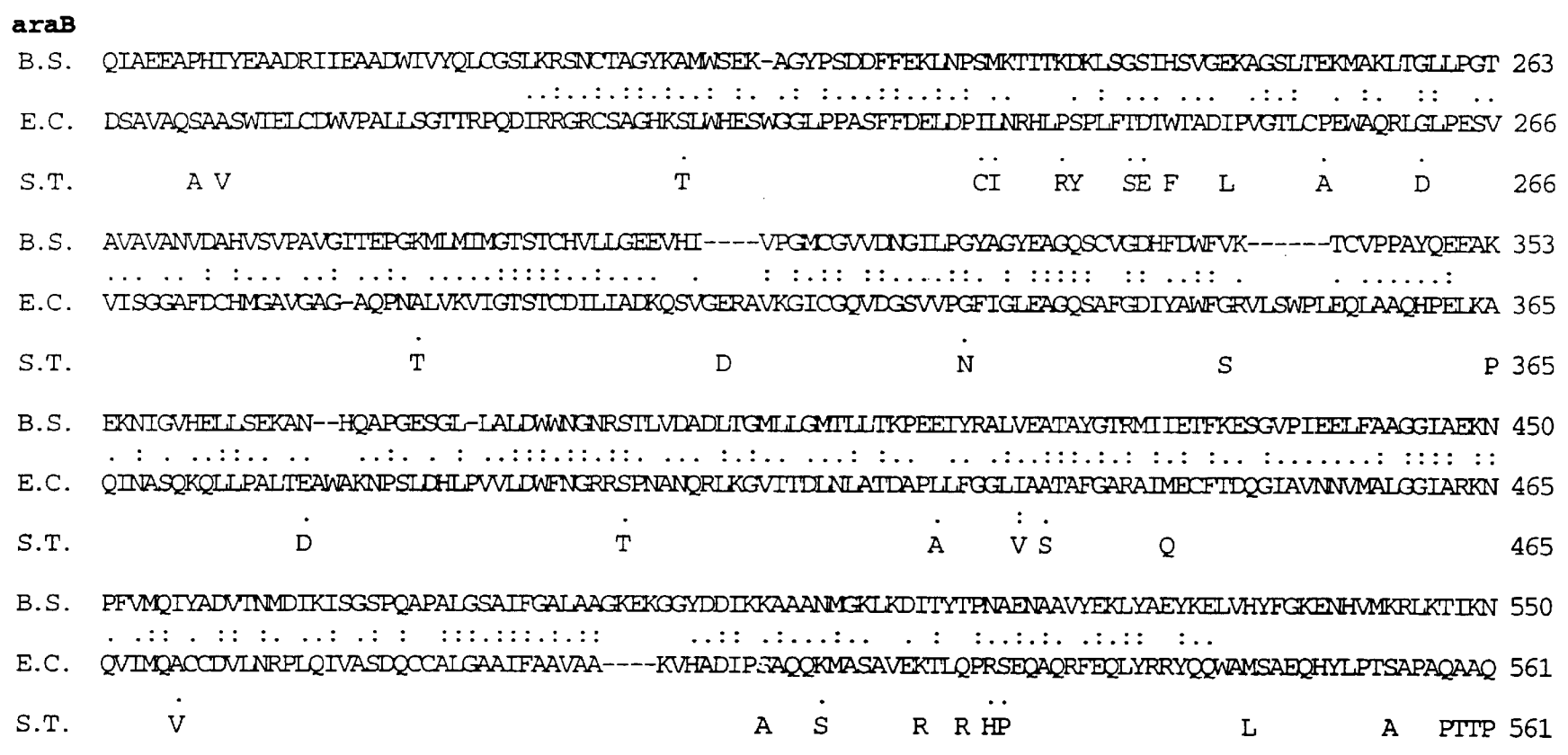

The *B. subtilis* araA gene could encode a 496 amino acid residue polypeptide with a predicted molecular mass, $M_r$ of 56,192 Da, which showed 52.5% identity, with a 495 amino acids overlap to AraA from *E. coli* (SEQ ID NO:16) and *S. typhimurium* (SEQ ID NO:17) (FIG. 9A). The araB gene could encode a 560 amino acid polypeptide with a predicted $M_r$ value of 60,973 Da and contiguous residues from 196 to 534 were 31.4% and 30.6% identical (350 a.a overlap) to *E. coli* AraB (SEQ ID NO:18) and *S. typhimurium* AraB (SEQ ID NO:19), respectively (FIG. 9B), *B. subtilis* araD gene could encode a 229 amino acid polypeptide with an $M_r$ of 25,669 Da which showed 58% identify in 231 overlap to *E. coli* AraD (SEQ ID NO:20) and 59% identity in 205 amino acid overlap to *S. typhimurium* AraD (SEQ ID NO:21) (FIG. 9C). The most significant divergency between amino acid sequences was observed at the N Terminal sequence of araB (170 amino acids). The *B. subtilis* AraA, AraB and AraD proteins were shown to be moderately hydrophilic according to Kyte and Doolittle [Kyte and Doolittle, *J Mol. Biol.*, 157:105–132 (1982)].

5'-End Mapping of ara mRNA. A promoter-like region was found upstream from the araA gene. The –35 and –10 region are identical to the consensus sequence (TTGACA and TATAAT) of the promoters recognized by *B. subtilis* σ-A form of RNA polymerase and show a spacing of 17 bp between –35 and –10 sequences as observed on many other *B. subtilis* promoters [Moran et al., In: *Bacillus subtilis and other Gram-positive bacteria: biochemistry, physiology, and molecular genetics.*, American Society for Microbiology, Washington, D.C., pp. 653–667 (1993)].

To determine the transcriptional start site and if inducibility is at the transcriptional level, RNA extracted from exponentially grown cells, in the presence and in the absence of L-arabinose, was analyzed by primer extension.

Reverse-transcripts were obtained using a 19-mer (primer A) and a 17-mer (primer B) complementary to part of the mRNA, 83 and 153 bases, respectively, from the presumed start site of transcription, as described in Materials and Methods. Fragments corresponding to the transcription start site at a T residue in the non-transcribed strand were obtained with both primers only with mRNA from the induced culture.

Figure 10:
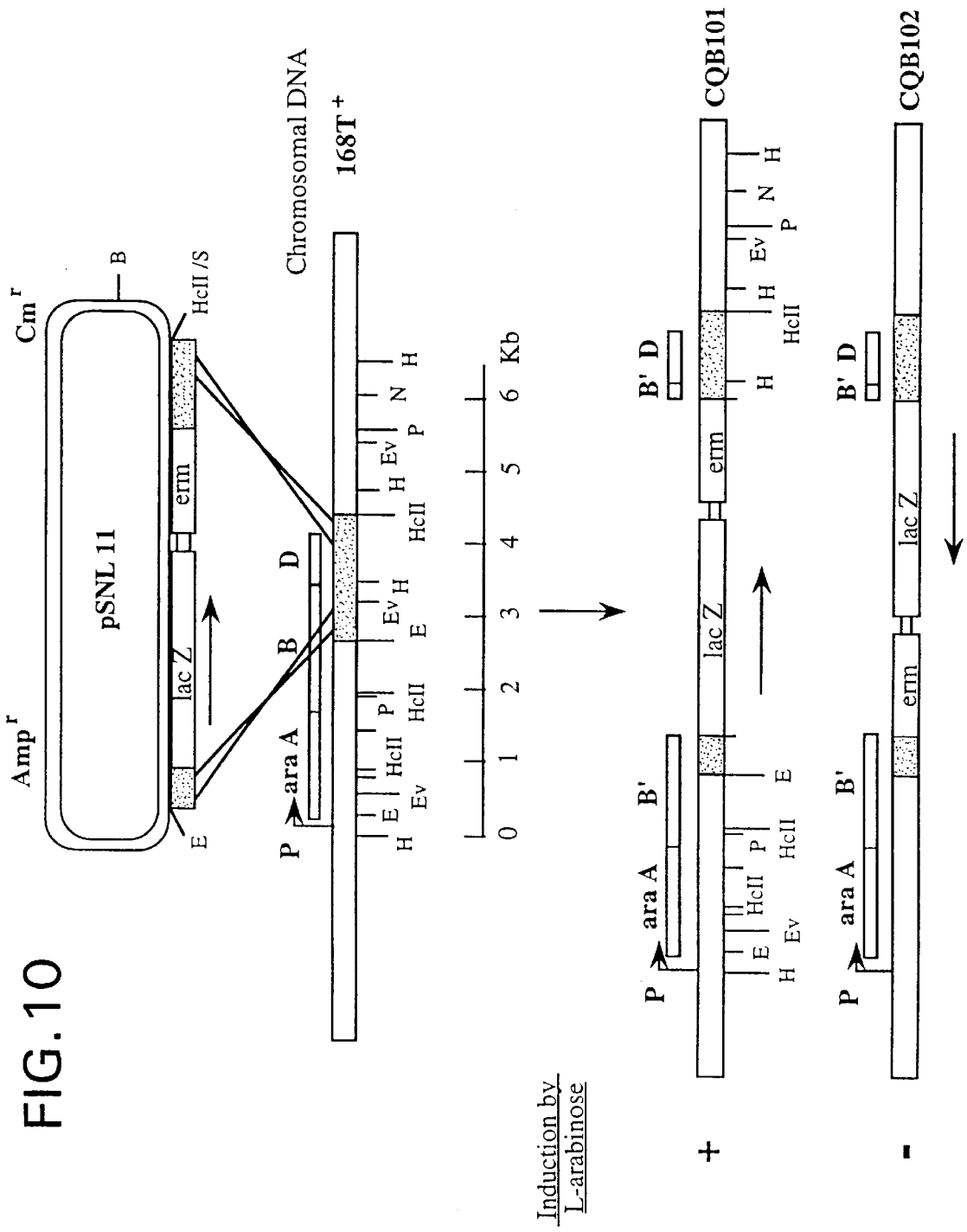
FIG. 10. Construction of araB-lacZ transcriptional fusions, and integration of the fusions into the chromosomes of *B. subtilis* by a double crossover. Plasmid pSNL11 was constructed by insertion of the lacZ and erm genes into the araB gene at the unique Eco RV site of the 1.7 Kb HincII-EcoRI fragment (shaded area). Strain IQB102 was obtained by the same procedure using plasmid pSNL12 which has lacZ and erm genes cloned in the opposite orientation as described in the methods. The double crossover event on both cases disrupted the araB gene which resulted in insertional inactivation of the gene. The location of the ara genes is shown by the upper empty bars. The promoter (P) of the ara operon is indicated by the arrow preceding araA gene. HcII/S represents the Hinc II site cloned into Sma I site; Bg/II, (B); Eco RI, (E); Eco RV, (Ev); Hind II, (H); Nco I, (N); Pst I, (P).

Expression of araB-lacZ Transcriptional Fusions—The araA, araB and araD genes are adjacent. The direction of transcription is from araA to araD and no obvious transcription termination sequence is present between the three genes, suggesting that they are organized in an operon. To facilitate the study of the regulation of expression of the araA, araB and araD genes, a transcriptional araA, araB-lacZ fusion was constructed. Plasmids pSNL11 and PSNL12 were obtained by inserting a DNA fragment containing the lacZ$^+$ and erm genes from pTV32 [Perkins and Youngman, 1986, supra] into the araB gene in opposite orientations (see Materials and Methods). The two plasmids were linearized by Bgl II, used to transform *B. subtilis* 168T$^+$ and selection was made for Em$^r$Cm$^s$ transformants. The use of linear DNA ensured a double crossover event leading to the integration of the araB-lacZ and the erm marker into the chromosome, which was confirmed by Southern hybridization (results not shown). The resulting strains IQB101 and IQB102 showed an Ara$^-$ phenotype, and their structure is presented in FIG. 10.

In strain IQB101 and araB-lacZ transcriptional fusion was obtained by fusion lacZ to the araB gene in the appropriate orientation of transcription. In strain IQB102, the lacZ gene was fused in the opposite orientation. The β-galactosidase activity of the resulting strains was tested on MMCH-X-gal plates. Upon addition of L-arabinose to the medium, colonies of IQB101 presented a dark blue phenotype whereas those of IQB102 remained white, confirming that the direction of transcription is from araB to araD. Strain IQB101 was grown on plates MMCH-X-gal 0.04% L-arabinose, MMCH-X-gal 0.04% glucose, MMCH-X-gal 0.2% Glucose+0.2% L-arabinose and β-galactosidase activity was tested. Only the colonies grown on MMCH-X-gal L-arabinose plates showed a dark blue phenotype. Thus, L-arabinose is the physiological inducer which stimulates the expression of the araB-lacZ fusion at the transcriptional level and araB transcription is subjected to catabolite repression.

Discussion

Using recombinant strains of *B. subtilis* bearing araB-lacZ fusions, the expression of the ara genes was studied. It was shown that the transcription of ara gene is inducible by L-arabinose, using an araB-lacZ fusion. These results were also consistent with the ones obtained by primer extension analysis. Using the same lacZ fusion, it was demonstrated that the expression of ara genes is repressed by glucose.

The 5' end of araABD operon was precisely determined by reverse transcriptase mapping and the promoter region identified. The 5' terminus of araABD transcript was located at a T residue (FIG. 1). The –35 and –10 regions are identical to the consensus sequence for the (A promoters in *B. subtilis* [TTGACA(17 bp)-TATAAT(18)] (SEQ ID NO:38).

In previous work [(Sá-Nogueira et al., *J. Bacteriol.*, 170:2855–2857 (1988)], the existence of constitutive mutants for L-arabinose utilization was reported. Although these mutations are clustered in a different region of the chromosome, they influence the expression of the genes araA, araB and araD. Therefore, a regulatory role for the affected locus araC seemed plausible. Expression of araABD operon is inducible by L-arabinose. So, it can be assumed that the product(s) of a regulatory gene(s) interacts with the promoter region of the operon. Six regions possibly involved in transcription regulation were identified near the promoter (FIG. 11) (SEQ ID NO: 1). The first two were found upstream from the −35 region: an inverted repeat of ten nucleotides (IR1) located upstream from the −35 region (position −49 to −77, FIG. 11 (SEQ ID NO:2) and two direct repeats (comprise between position −66 to −113, FIG. 11). Downstream from IR1, three other inverted repeats were found: the first, IR2, located in the −35 region (SEQ ID NO:3); the second, IR3, located in the −10 region; and the third (SEQ ID NO:4); IR4, in the +4−+20 region (SEQ ID NO:5) (FIG. 11). All these sequences may be putative operator-like regions, and IR1 might also be a putative transcription terminator of a gene located upstream from the cloned fragment. Downstream from the transcription start site, the DNA sequence, +20-ATAGGTTTATTTTCTATC ATTAGT ACGT-+47 (SEQ ID NO:6) (FIG. 11) show some similarity to the sequence recognized by the product of the regulatory gene, araC, at the *E. coli* araBAD promoter ATAGCATTTTTATCCATAAGATTAGCGG (SEQ ID NO:7) [Brunell and Schleif, *J. Mol. Biol.*, 209:607–622 (1989)].

Expression of the ara genes is repressed by glucose as demonstrated by using the ara-lacZ fusion integrated into the ara region. In a previous work [Sá-Nogueira et al., 1988, supra], it was observed that strains carrying constitutive mutations at the araC locus still retained catabolite repression of the L-arabinose isomerase expression. Thus, it appears that inducer exclusion does not play a major role in carbon regulation of isomerase expression. Although the regulatory system mediating catabolite repression in *B. subtilis* is unknown, there is some evidence that it is accomplished by a negative regulatory mechanism [Chambliss, In: *Bacillus subtilis and other Gram-positive bacteria: biochemistry, physiology, and molecular genetics*, American Society for Microbiology, Washington, D.C., pp. 213–219 (1993)]. This evidence is based on the location and sequences of cis-acting sites responsible for catabolite repression of several *B. subtilis* genes and operons [Chambliss, 1993, supra]; these sequences are similar to the *B. subtilis* catabolite repression consensus sequence (TGWNANCGNTNWCA) (SEQ ID NO:8) deduced from mutagenesis studies of the amyE catabolite repression operator site [Weickert and Chambliss, *Proc. Natl. Acad. Sci. USA*, 87:6238–6242 (1990)]. Moreover, a trans-acting gene product CcpA which is involved in catabolite repression of the amyE gene was identified [Henkin et al., *Mol. Microbiol.*, 5:575–584 (1991)]. Sequence analysis suggests that CcpA is a DNA-binding protein, but it is not known whether CcpA is directly involved in the mechanism of catabolite repression [Chambliss, 1993, supra; Fujita and Miwa, *J. Bacteriol.*, 176:511–513 (1994)]. The promoter region of the araABD operon contains a sequence, +60 TGAAAGCGTTTTAT +73 (SEQ ID NO:9) (FIG. 11) very similar to the catabolite repression consensus sequence. A second sequence, which shows a weak similarity with the catabolite repression consensus sequence, was found within the araA gene, +160 TGTGACAGGAAGCC +173 (SEQ ID NO:10) (FIG. 11). In this work, it is shown that the catabolite repression of the ara operon acts at the transcriptional level; thus, these sequences might be putative cis-acting sites responsible for catabolite repression of the ara genes.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

The following is a list of documents related to the above disclosure and particularly to the experimental procedures and discussions.

Ausubel, F. M.; Bren, R.; Kingston, R.; Moore, D. D.; Smith, J. A.; Seidman, J. G.; and Struttl, K. (1987–1988). In *Current Protocols in Molecular Biology*. Ed. Green Publishing Associates and Wiley-Interscience.

Biarboim, H. C. and Doly, J. (1979). A rapid alkaline extraction procedure for screening recombinant plasmid DNA. *Nucleic Acids Res.* 7: 1513–1523.

Brunelle, A. and Schleif, R. 1989. Determining residue base interactions between araC protein and araI DNA. *J. Mol. Biol.* Biol. 209: 607–622.

Ferrari, F. A.; Ferrari, E.; and Hoch, J. 1982. Chromosomal location of a *Bacillus subtilis* DNA fragment uniquely transcribed by Sigma-28 containing RNA polymerase. *J. Bacteriol.* 152:782–785.

Pearson, W. R. and Lipman, D. J. 1988. Improved tools for biological sequence comparison. *Proc. Natl. Acad. Sci. USA*. 85:2444–2448.

Perego, M. and Hoch, J. 1988. Molecular cloning of the transcription inhibitor abrB of *Bacillus subtilis*. p. 129–134. In *Genetics and Biotechnology of Bacilli*. Vol. 2, Academic Press.

Yasbin, R.; Wilson, G.; and Young, F. 1973. Transformation and transfection in lysogenic strains of *Bacillus subtilis* 168. *J. Bacteriol.* 113:540–548.

Youngman, P. 1985. Plasmid vectors for recovering and exploiting Tn917 transpositions in Bacillus and other gram-positives. In Plasmids: a practical approach. Kitardy (Ed.). IRL Press, Oxford.

Zalkin, H. and Ebbole, D. J. 1988. Organization and regulation of genes encoding Biosynthetic enzymes in *Bacillus subtilis*. *J. Biol. Chem.* 263:1595–1598.

What is claimed is:

1. An isolated nucleic acid, comprising a promoter sequence which promotes the expression of a protein in a prokaryotic host, wherein the coding sequence encoding the protein is operably positioned in proper reading frame 3' to the promoter sequence, and the expression of the protein is inducible in the presence of exogenously supplied L-arabinose and repressible in the presence of exogenously supplied glucose;
   wherein the promoter sequence is from the *Bacillus subtilis* L-arabinose operon.

2. The isolated nucleic acid of claim 1, wherein the promoter sequence is identified within a 150 bp DNA fragment upstream from the translation site of the araA gene.

3. The isolated nucleic acid of claim 2, wherein the promoter sequence comprises three inverted repeats, and a putative operator-like sequence in the −35 and −10 regions.

4. The isolated nucleic acid of claim 3, wherein the promoter sequence further comprises a potential hairpin-loop structure with a ΔG value of about −19.2 kcal/mol centered 27 bp upstream from the −35 region.

5. The isolated nucleic acid of claim 4, wherein the promoter sequence comprises the nucleotide sequence of SEQ ID NO: 1.

6. The isolated nucleic acid of claim 5, wherein the promoter sequence consists of SEQ ID NO:1.

7. A vector for the expression of a protein in a prokaryotic host comprising the nucleic acid of claim 1.

8. The vector of claim 7 operably positioned in proper reading frame with a gene for an exogenous protein.

9. A vector for the expression of a protein in a prokaryotic host comprising the nucleic acid of claim 5.

10. The vector of claim 9 operably positioned in proper reading frame with a gene for an exogenous protein.

11. A prokaryotic host transformed with the vector of claim 9.

12. A prokaryotic host transformed with the vector of claim 10.

13. The isolated nucleic acid of claim 1 operably positioned in proper reading frame with an ara gene.

14. The isolated nucleic acid of claim 13, further comprising a ribosome binding site 5' to the ara gene.

15. A method of regulating an exogenous protein in a prokaryotic host cell comprising inserting the vector of claim 8 into a prokaryotic host and inducing its expression by adding L-arabinose and repressing its expression with glucose.

16. A method of regulating an exogenous protein in a prokaryotic host cell comprising inserting the vector of claim 10 into a prokaryotic host and inducing its expression by adding L-arabinose and repressing its expression with glucose.

17. The isolated nucleic acid of claim 4, wherein the promoter sequence comprises SEQ ID NO:2, SEQ ID NO:3 and SEQ ID NO:4.

18. An isolated nucleic acid that is complementary to the promoter sequence of claim 6; wherein the nucleic acid is between 15–25 nucleotides.

19. An isolated nucleic acid, comprising a promoter sequence which promotes the expression of a protein in a prokaryotic host, wherein the coding sequence encoding the protein is operably positioned in proper reading frame 3' to the promoter sequence, and the expression of the protein is inducible in the presence of exogenously supplied L-arabinose; wherein said promoter sequence comprises a nucleotide sequence that is a 75% nucleotide for nucleotide match with SEQ ID NO:1 over the defined length of SEQ ID NO:1.

20. A vector for the expression of a protein in a prokaryotic host comprising the nucleic acid of claim 19.

21. A method of regulating an exogenous protein in a prokaryotic host cell comprising inserting the vector of claim 20 into a prokaryotic host and inducing its expression by adding L-arabinose.

22. The isolated nucleic acid of claim 19 wherein the expression of the protein is repressible in the presence of exogenously supplied glucose.

* * * * *

SEQUENCE LISTING (1) GENERAL INFORMATION:

(iii) NUMBER OF SEQUENCES: 64

(2) INFORMATION FOR SEQ ID NO:1:

```
        (i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus subtilis (ix) FEATURE:
            (A) NAME/KEY: -10 signal
            (B) LOCATION: 119..124

(ix) FEATURE:
            (A) NAME/KEY: -35 signal
            (B) LOCATION: 96..101

(ix) FEATURE:
            (A) NAME/KEY: CDS
            (B) LOCATION: 228..281

(ix) FEATURE:
            (A) NAME/KEY: RBS
            (B) LOCATION: 211..219

(xi) SEQUENCE DESCRIPTION: SEQ ID NO:1:

AAGCTTCTCA TCAATGATTT GAATTGGAGC TCGGGCTGGC CGTCCTATTG AATTAAAAAG        60

CCGGCTCTGC CCCCGGCTTT TTTTAAAAGA AAAGATTGAC AGTATAATAG TCAATTACTA       120

TAATAAAATT GTTCGTACAA ATATTTATTT ATAGGTTTAT TTTCTATCAT TAGTACGTAT       180

CTTTTGTATT TGAAAGCGTT TTATTTTATG AGAAAGGGGC AGTTTAC ATG CTT CAG         236
                                                     Met Leu Gln
                                                       1

ACA AAG GAT TAT GAA TTC TGG TTT GTG ACA GGA AGC CAG CAC CTA             281
Thr Lys Asp Tyr Glu Phe Trp Phe Val Thr Gly Ser Gln His Leu
      5                  10                  15

(2) INFORMATION FOR SEQ ID NO:2:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus subtilis (ix) FEATURE:
            (A) NAME/KEY: misc_feature
            (B) LOCATION: 1..28

(xi) SEQUENCE DESCRIPTION: SEQ ID NO:2:

AAAAAGCCGG CTCTGCCCCC GGCTTTTT                                           28

(2) INFORMATION FOR SEQ ID NO:3:

(i) SEQUENCE CHARACTERISTICS:
            (A) LENGTH: 30 base pairs
            (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..30

(xi) SEQUENCE DESCRIPTION: SEQ ID NO:3:

ATTGACAGTA TAATAGTCAA TTACTATAAT                                           30

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..23

(xi) SEQUENCE DESCRIPTION: SEQ ID NO:4:

TATAATAGTC AATTACTATA ATA                                                  23

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..22

(xi) SEQUENCE DESCRIPTION: SEQ ID NO:5:

CGTACAAATA TTTATTTATA GG                                                   22

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
```

```
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Bacillus subtilis (xi) SEQUENCE DESCRIPTION: SEQ ID NO:6:

ATAGGTTTAT TTTCTATCAT TAGTACGT                                              28

(2) INFORMATION FOR SEQ ID NO:7:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Bacillus subtilis (xi) SEQUENCE DESCRIPTION: SEQ ID NO:7:

ATAGCATTTT TATCCATAAG ATTAGCGG                                              28

(2) INFORMATION FOR SEQ ID NO:8:

(i) SEQUENCE CHARACTERISTICS:
         (A) LENGTH: 14 base pairs
         (B) TYPE: nucleic acid
         (C) STRANDEDNESS: single
         (D) TOPOLOGY: unknown (ii) MOLECULE TYPE:

(iii) HYPOTHETICAL: NO (iv) ANTI-SENSE: NO (v) FRAGMENT TYPE: internal (vi) ORIGINAL SOURCE:
         (A) ORGANISM: Bacillus subtilis (xi) SEQUENCE DESCRIPTION: SEQ ID NO:8:

TGWNANCGNT NWCA                                                             14

(2) INFORMATION FOR SEQ ID NO:9:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Bacillus subtilis
```

```
     (xi) SEQUENCE DESCRIPTION: SEQ ID NO:9:

TGAAAGCGTT TTAT                                                         14

(2) INFORMATION FOR SEQ ID NO:10:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Bacillus subtilis (xi) SEQUENCE DESCRIPTION: SEQ ID NO:10:

TGTGACAGGA AGCC                                                         14

(2) INFORMATION FOR SEQ ID NO:11:

(i) SEQUENCE CHARACTERISTICS:
          (A) LENGTH: 10917 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (vi) ORIGINAL SOURCE:
          (A) ORGANISM: Bacillus subtilis (ix) FEATURE:
          (A) NAME/KEY: CDS
          (B) LOCATION: 228..1718
          (D) OTHER INFORMATION: /product= "araA"

(ix) FEATURE:
          (A) NAME/KEY: CDS
          (B) LOCATION: 1732..3417
          (D) OTHER INFORMATION: /product= "araB"

(ix) FEATURE:
          (A) NAME/KEY: CDS
          (B) LOCATION: 3431..4120
          (D) OTHER INFORMATION: /product= "araD"

(ix) FEATURE:
          (A) NAME/KEY: misc_feature
          (B) LOCATION: 4107..4916
          (D) OTHER INFORMATION: /product= "araL"

(ix) FEATURE:
          (A) NAME/KEY: CDS
          (B) LOCATION: 4913..6097
          (D) OTHER INFORMATION: /product= "araM"

(ix) FEATURE:
          (A) NAME/KEY: CDS
          (B) LOCATION: 6128..7429
          (D) OTHER INFORMATION: /product= "araN"

(ix) FEATURE:
          (A) NAME/KEY: CDS
          (B) LOCATION: 7465..8406
          (D) OTHER INFORMATION: /product= "araP"

(ix) FEATURE:
          (A) NAME/KEY: CDS
```

(B) LOCATION: 8407..9255
         (D) OTHER INFORMATION: /product= "araQ"

(ix) FEATURE:
         (A) NAME/KEY: CDS
         (B) LOCATION: 9271..10773
         (D) OTHER INFORMATION: /product= "abfA"

(xi) SEQUENCE DESCRIPTION: SEQ ID NO:11:

AAGCTTCTCA TCAATGATTT GAATTGGAGC TCGGGCTGGC CGTCCTATTG AATTAAAAAG        60

CCGGCTCTGC CCCCGGCTTT TTTTAAAAGA AAAGATTGAC AGTATAATAG TCAATTACTA       120

TAATAAAATT GTTCGTACAA ATATTTATTT ATAGGTTTAT TTTCTATCAT TAGTACGTAT       180

CTTTTGTATT TGAAAGCGTT TTATTTTATG AGAAAGGGGC AGTTTAC ATG CTT CAG         236
                                                   Met Leu Gln
                                                     1

ACA AAG GAT TAT GAA TTC TGG TTT GTG ACA GGA AGC CAG CAC CTA TAC         284
Thr Lys Asp Tyr Glu Phe Trp Phe Val Thr Gly Ser Gln His Leu Tyr
     5                  10                  15

GGG GAA GAG ACG CTG GAA CTC GTA GAT CAG CAT GCT AAA AGC ATT TGT         332
Gly Glu Glu Thr Leu Glu Leu Val Asp Gln His Ala Lys Ser Ile Cys
 20                  25                  30                  35

GAG GGG CTC AGC GGG ATT TCT TCC AGA TAT AAA ATC ACT CAT AAG CCC         380
Glu Gly Leu Ser Gly Ile Ser Ser Arg Tyr Lys Ile Thr His Lys Pro
                 40                  45                  50

GTC GTC ACT TCA CCG GAA ACC ATT AGA GAG CTG TTA AGA GAA GCG GAG         428
Val Val Thr Ser Pro Glu Thr Ile Arg Glu Leu Leu Arg Glu Ala Glu
             55                  60                  65

TAC AGT GAG ACA TGT GCT GGC ATC ATT ACA TGG ATG CAC ACA TTT TCC         476
Tyr Ser Glu Thr Cys Ala Gly Ile Ile Thr Trp Met His Thr Phe Ser
         70                  75                  80

CCT GCA AAA ATG TGG ATA GAA GGC CTT TCC TCT TAT CAA AAA CCG CTT         524
Pro Ala Lys Met Trp Ile Glu Gly Leu Ser Ser Tyr Gln Lys Pro Leu
 85                  90                  95

ATG CAT TTG CAT ACC CAA TAT AAT CGC GAT ATC CCG TGG GGT ACG ATT         572
Met His Leu His Thr Gln Tyr Asn Arg Asp Ile Pro Trp Gly Thr Ile
100                 105                 110                 115

GAC ATG GAT TTT ATG AAC AGC AAC CAA TCC GCG CAT GGC GAT CGA GAG         620
Asp Met Asp Phe Met Asn Ser Asn Gln Ser Ala His Gly Asp Arg Glu
                 120                 125                 130

TAC GGT TAC ATC AAC TCG AGA ATG GGG CTT AGC CGA AAA GTC ATT GCC         668
Tyr Gly Tyr Ile Asn Ser Arg Met Gly Leu Ser Arg Lys Val Ile Ala
             135                 140                 145

GGC TAT TGG GAT GAT GAA GAA GTG AAA AAA GAA ATG TCC CAG TGG ATG         716
Gly Tyr Trp Asp Asp Glu Glu Val Lys Lys Glu Met Ser Gln Trp Met
         150                 155                 160

GAT ACG GCG GCT GCA TTA AAT GAA AGC AGA CAT ATT AAG GTT GCC AGA         764
Asp Thr Ala Ala Ala Leu Asn Glu Ser Arg His Ile Lys Val Ala Arg
165                 170                 175

TTT GGA GAT AAC ATG CGT CAT GTC GCG GTA ACG GAC GGA GAC AAG GTG         812
Phe Gly Asp Asn Met Arg His Val Ala Val Thr Asp Gly Asp Lys Val
180                 185                 190                 195

GGA GCG CAT ATT CAA TTT GGC TGG CAG GTT GAC GGA TAT GGC ATC GGG         860
Gly Ala His Ile Gln Phe Gly Trp Gln Val Asp Gly Tyr Gly Ile Gly
                 200                 205                 210

GAT CTC GTT GAA GTG ATG GAT CGC ATT ACG GAC GAC GAG GTT GAC ACG         908
Asp Leu Val Glu Val Met Asp Arg Ile Thr Asp Asp Glu Val Asp Thr
             215                 220                 225

CTT TAT GCC GAG TAT GAC AGA CTA TAT GTG ATC AGT GAG GAA ACA AAA         956
Leu Tyr Ala Glu Tyr Asp Arg Leu Tyr Val Ile Ser Glu Glu Thr Lys
         230                 235                 240

```
CGT GAC GAA GCA AAG GTA GCG TCC ATT AAA GAA CAG GCG AAA ATT GAA     1004
Arg Asp Glu Ala Lys Val Ala Ser Ile Lys Glu Gln Ala Lys Ile Glu
    245             250             255

CTT GGA TTA ACC GCT TTT CTT GAG CAA GGC GGA TAC ACA GCG TTT ACG     1052
Leu Gly Leu Thr Ala Phe Leu Glu Gln Gly Gly Tyr Thr Ala Phe Thr
260             265             270             275

ACA TCG TTT GAA GTG CTG CAC GGA ATG AAA CAG CTG CCG GGA CTT GCC     1100
Thr Ser Phe Glu Val Leu His Gly Met Lys Gln Leu Pro Gly Leu Ala
            280             285             290

GTT CAG CGC CTG ATG GAG AAA GGC TAT GGG TTT GCC GGT GAA GGA GAT     1148
Val Gln Arg Leu Met Glu Lys Gly Tyr Gly Phe Ala Gly Glu Gly Asp
        295             300             305

TGG AAG ACA GCG GCC CTT GTA CGG ATG ATG AAA ATC ATG GCT AAA GGA     1196
Trp Lys Thr Ala Ala Leu Val Arg Met Met Lys Ile Met Ala Lys Gly
    310             315             320

AAA AGA ACT TCC TTC ATG GAA GAT TAC ACG TAC CAT TTT GAA CCG GGA     1244
Lys Arg Thr Ser Phe Met Glu Asp Tyr Thr Tyr His Phe Glu Pro Gly
325             330             335

AAT GAA ATG ATT CTG GGC TCT CAC ATG CTT GAA GTG TGT CCG ACT GTC     1292
Asn Glu Met Ile Leu Gly Ser His Met Leu Glu Val Cys Pro Thr Val
340             345             350             355

GCT TTG GAT CAG CCG AAA ATC GAG GTT CAT TCG CTT TCG ATT GGC GGC     1340
Ala Leu Asp Gln Pro Lys Ile Glu Val His Ser Leu Ser Ile Gly Gly
            360             365             370

AAA GAG GAC CCT GCG CGT TTG GTA TTT AAC GGC ATC AGC GGT TCT GCC     1388
Lys Glu Asp Pro Ala Arg Leu Val Phe Asn Gly Ile Ser Gly Ser Ala
        375             380             385

ATT CAA GCT AGC ATT GTT GAT ATT GGC GGG CGT TTC CGC CTT GTG CTG     1436
Ile Gln Ala Ser Ile Val Asp Ile Gly Gly Arg Phe Arg Leu Val Leu
    390             395             400

AAT GAA GTC AAC GGC CAG GAA ATT GAA AAA GAC ATG CCG AAT TTA CCG     1484
Asn Glu Val Asn Gly Gln Glu Ile Glu Lys Asp Met Pro Asn Leu Pro
405             410             415

GTT GCC CGT GTT CTC TGG AAG CCG GAG CCG TCA TTG AAA ACA GCA GCG     1532
Val Ala Arg Val Leu Trp Lys Pro Glu Pro Ser Leu Lys Thr Ala Ala
420             425             430             435

GAG GCA TGG ATT TTA GCC GGC GGT GCA CAC CAT ACC TGC CTG TCT TAT     1580
Glu Ala Trp Ile Leu Ala Gly Gly Ala His His Thr Cys Leu Ser Tyr
            440             445             450

GAA CTG ACA GCG GAG CAA ATG CTT GAT TGG GCG GAA ATG GCG GGA ATC     1628
Glu Leu Thr Ala Glu Gln Met Leu Asp Trp Ala Glu Met Ala Gly Ile
        455             460             465

GAA AGT GTT CTC ATT TCC CGT GAT ACG ACA ATT CAT AAA CTG AAA CAC     1676
Glu Ser Val Leu Ile Ser Arg Asp Thr Thr Ile His Lys Leu Lys His
    470             475             480

GAG TTA AAA TGG AAC GAG GCG CTT TAC CGG CTT CAA AAG TAG              1718
Glu Leu Lys Trp Asn Glu Ala Leu Tyr Arg Leu Gln Lys *
485             490             495

AGGGGGATGT CAC ATG GCT TAC ACA ATA GGG GTT GAT TTT GGA ACT TTA     1767
           Met Ala Tyr Thr Ile Gly Val Asp Phe Gly Thr Leu
            1               5               10

TCA GGA AGA GCA GTG CTC GTT CAT GTC CAA ACA GGG GAG GAA CTT GCG     1815
Ser Gly Arg Ala Val Leu Val His Val Gln Thr Gly Glu Glu Leu Ala
        15              20              25

GCT GCT GTA AAA GAA TAC AGG CAT GCT GTC ATT GAT ACC GTC CTT CCA     1863
Ala Ala Val Lys Glu Tyr Arg His Ala Val Ile Asp Thr Val Leu Pro
    30              35              40

AAA ACG GGT CAA AAG CTG CCG CGT GAC TGG GCG CTG CAG CAC CCT GCT     1911
Lys Thr Gly Gln Lys Leu Pro Arg Asp Trp Ala Leu Gln His Pro Ala
```

-continued

```
            45                      50                      55                      60
GAT TAC CTC GAA GTC TTG GAA ACA ACC ATT CCG TCT TTA CTC GAA CAG        1959
Asp Tyr Leu Glu Val Leu Glu Thr Thr Ile Pro Ser Leu Leu Glu Gln
                        65                      70                      75

ACG GGC GTT GAC CCG AAA GAC ATT ATC GGG ATT GGA ATT GAT TTC ACG        2007
Thr Gly Val Asp Pro Lys Asp Ile Ile Gly Ile Gly Ile Asp Phe Thr
                    80                      85                      90

GCA TGT ACG ATC CTT CCT ATT GAC AGC AGC GGG CAG CCG TTA TGC ATG        2055
Ala Cys Thr Ile Leu Pro Ile Asp Ser Ser Gly Gln Pro Leu Cys Met
                95                     100                     105

CTG CCT GAA TAT GAA GAG GAG CCG CAC AGC TAT GTG AAG CTC TGG AAG        2103
Leu Pro Glu Tyr Glu Glu Glu Pro His Ser Tyr Val Lys Leu Trp Lys
            110                     115                     120

CAT CAT GCG GCC CAA AAA CAT GCT GAT CGG CTC AAT CAA ATC GCG GAA        2151
His His Ala Ala Gln Lys His Ala Asp Arg Leu Asn Gln Ile Ala Glu
125                     130                     135                     140

GAA GAA GGA GAG GCT TTT TTA CAG CGG TAC GGA GGA AAA ATT TCA TCA        2199
Glu Glu Gly Glu Ala Phe Leu Gln Arg Tyr Gly Gly Lys Ile Ser Ser
                        145                     150                     155

GAA TGG ATG ATT CCA AAG GTC ATG CAA ATT GCC GAG GAA GCG CCT CAC        2247
Glu Trp Met Ile Pro Lys Val Met Gln Ile Ala Glu Glu Ala Pro His
                    160                     165                     170

ATT TAT GAA GCG GCT GAC CGG ATC ATC GAG GCT GCG GAC TGG ATC GTG        2295
Ile Tyr Glu Ala Ala Asp Arg Ile Ile Glu Ala Ala Asp Trp Ile Val
                175                     180                     185

TAC CAG CTG TGC GGC TCG CTC AAG CGA AGC AAT TGT ACC GCA GGG TAT        2343
Tyr Gln Leu Cys Gly Ser Leu Lys Arg Ser Asn Cys Thr Ala Gly Tyr
            190                     195                     200

AAA GCG ATG TGG AGT GAA AAA GCG GGG TAT CCG TCA GAT GAT TTC TTT        2391
Lys Ala Met Trp Ser Glu Lys Ala Gly Tyr Pro Ser Asp Asp Phe Phe
205                     210                     215                     220

GAG AAA TTA AAT CCT TCA ATG AAA ACG ATT ACA AAG GAC AAA TTG TCA        2439
Glu Lys Leu Asn Pro Ser Met Lys Thr Ile Thr Lys Asp Lys Leu Ser
                        225                     230                     235

GGT TCT ATT CAT TCA GTA GGA GAA AAA GCC GGC AGT CTG ACT GAA AAA        2487
Gly Ser Ile His Ser Val Gly Glu Lys Ala Gly Ser Leu Thr Glu Lys
                    240                     245                     250

ATG GCA AAG CTG ACA GGG CTT CTC CCG GGA ACG GCT GTT GCG GTT GCC        2535
Met Ala Lys Leu Thr Gly Leu Leu Pro Gly Thr Ala Val Ala Val Ala
                255                     260                     265

AAT GTG GAC GCT CAT GTT TCG GTA CCG GCG GTC GGC ATT ACA GAG CCA        2583
Asn Val Asp Ala His Val Ser Val Pro Ala Val Gly Ile Thr Glu Pro
            270                     275                     280

GGG AAA ATG CTG ATG ATT ATG GGA ACC TCG ACG TGC CAT GTT CTA CTT        2631
Gly Lys Met Leu Met Ile Met Gly Thr Ser Thr Cys His Val Leu Leu
285                     290                     295                     300

GGT GAA GAG GTG CAT ATC GTT CCA GGA ATG TGC GGC GTT GTG GAC AAC        2679
Gly Glu Glu Val His Ile Val Pro Gly Met Cys Gly Val Val Asp Asn
                        305                     310                     315

GGA ATT CTC CCG GGC TAT GCG GGA TAT GAA GCC GGG CAG TCC TGT GTC        2727
Gly Ile Leu Pro Gly Tyr Ala Gly Tyr Glu Ala Gly Gln Ser Cys Val
                    320                     325                     330

GGC GAT CAT TTT GAC TGG TTT GTG AAA ACA TGT GTC CCG CCA GCT TAT        2775
Gly Asp His Phe Asp Trp Phe Val Lys Thr Cys Val Pro Pro Ala Tyr
                335                     340                     345

CAA GAG GAA GCA AAG GAA AAA AAC ATT GGC GTT CAT GAG CTG CTG AGT        2823
Gln Glu Glu Ala Lys Glu Lys Asn Ile Gly Val His Glu Leu Leu Ser
            350                     355                     360

GAG AAA GCA AAC CAT CAA GCG CCT GGT GAA AGC GGC TTG CTT GCT TTA        2871
```

```
Glu Lys Ala Asn His Gln Ala Pro Gly Glu Ser Gly Leu Leu Ala Leu
365                 370                 375                 380

GAT TGG TGG AAT GGA AAC CGT TCA ACT CTT GTT GAT GCA GAT TTA ACA       2919
Asp Trp Trp Asn Gly Asn Arg Ser Thr Leu Val Asp Ala Asp Leu Thr
                    385                 390                 395

GGG ATG CTG CTT GGC ATG ACA CTG CTG ACG AAG CCT GAA GAG ATT TAT       2967
Gly Met Leu Leu Gly Met Thr Leu Leu Thr Lys Pro Glu Glu Ile Tyr
                400                 405                 410

AGA GCG TTA GTT GAA GCG ACA GCT TAC GGA ACC CGG ATG ATT ATC GAA       3015
Arg Ala Leu Val Glu Ala Thr Ala Tyr Gly Thr Arg Met Ile Ile Glu
            415                 420                 425

ACA TTC AAA GAA AGC GGT GTT CCG ATT GAG GAA CTG TTC GCA GCC GGC       3063
Thr Phe Lys Glu Ser Gly Val Pro Ile Glu Glu Leu Phe Ala Ala Gly
        430                 435                 440

GGA ATA GCT GAG AAA AAC CCG TTT GTC ATG CAG ATT TAT GCG GAT GTG       3111
Gly Ile Ala Glu Lys Asn Pro Phe Val Met Gln Ile Tyr Ala Asp Val
445                 450                 455                 460

ACA AAC ATG GAC ATT AAA ATC TCT GGT TCA CCG CAA GCC CCA GCC TTA       3159
Thr Asn Met Asp Ile Lys Ile Ser Gly Ser Pro Gln Ala Pro Ala Leu
                    465                 470                 475

GGA TCT GCC ATT TTC GGC GCG CTT GCA GCA GGC AAA GAA AAA GGC GGC       3207
Gly Ser Ala Ile Phe Gly Ala Leu Ala Ala Gly Lys Glu Lys Gly Gly
                480                 485                 490

TAC GAT GAT ATC AAA AAG GCA GCG GCG AAC ATG GGA AAA CTG AAA GAT       3255
Tyr Asp Asp Ile Lys Lys Ala Ala Ala Asn Met Gly Lys Leu Lys Asp
            495                 500                 505

ATA ACT TAT ACG CCA AAT GCC GAA AAC GCC GCG GTT TAT GAA AAA TTG       3303
Ile Thr Tyr Thr Pro Asn Ala Glu Asn Ala Ala Val Tyr Glu Lys Leu
        510                 515                 520

TAC GCT GAA TAT AAA GAG CTG GTT CAT TAT TTC GGA AAA GAA AAC CAT       3351
Tyr Ala Glu Tyr Lys Glu Leu Val His Tyr Phe Gly Lys Glu Asn His
525                 530                 535                 540

GTC ATG AAG CGT CTG AAA ACG ATC AAA AAT CTT CAA TTT TCA TCT GCC       3399
Val Met Lys Arg Leu Lys Thr Ile Lys Asn Leu Gln Phe Ser Ser Ala
                    545                 550                 555

GCC AAA AAG AAT TGA TAA AGGGTGATGG AGC ATG CTT GAA ACA TTA AAA        3448
Ala Lys Lys Asn *   *                   Met Leu Glu Thr Leu Lys
                560                                 1               5

AAA GAA GTG CTG GCT GCC AAC CTG AAG CTT CAA GAG CAT CAG CTG GTA       3496
Lys Glu Val Leu Ala Ala Asn Leu Lys Leu Gln Glu His Gln Leu Val
                10                  15                  20

ACC TTT ACG TGG GGA AAT GTC AGC GGC ATT GAC CGT GAA AAA GAA AGA       3544
Thr Phe Thr Trp Gly Asn Val Ser Gly Ile Asp Arg Glu Lys Glu Arg
            25                  30                  35

ATT GTC ATC AAA CTA GCG GAG TCG AAT ACC AGC GAC CTG ACA GCC GAT       3592
Ile Val Ile Lys Leu Ala Glu Ser Asn Thr Ser Asp Leu Thr Ala Asp
        40                  45                  50

GAC TTG GTT GTT TTG AAC CTT GAT GGA GAG GTC GTC GAA GGC TCG CTT       3640
Asp Leu Val Val Leu Asn Leu Asp Gly Glu Val Val Glu Gly Ser Leu
55                  60                  65                  70

AAA CCT TCT TCA GAT ACA CCT ACC CAT GTT TAT CTA TAT AAA GCC TTT       3688
Lys Pro Ser Ser Asp Thr Pro Thr His Val Tyr Leu Tyr Lys Ala Phe
                75                  80                  85

CCG AAT ATC GGG GGA ATT GTC CAT ACC CAT TCT CAA TGG GCG ACA AGC       3736
Pro Asn Ile Gly Gly Ile Val His Thr His Ser Gln Trp Ala Thr Ser
            90                  95                  100

TGG GCG CAA TCG GGC AGA GAC ATC CCT CCG TTA GGC ACG ACC CAT GCT       3784
Trp Ala Gln Ser Gly Arg Asp Ile Pro Pro Leu Gly Thr Thr His Ala
        105                 110                 115
```

```
GAT TAT TTT GAC AGT GCG ATT CCA TGT ACT CGA GAA ATG TAC GAT GAA       3832
Asp Tyr Phe Asp Ser Ala Ile Pro Cys Thr Arg Glu Met Tyr Asp Glu
    120             125             130

GAA ATC ATT CAT GAC TAC GAA CTG AAT ACA GGA AAA GTC ATA GCG GAA       3880
Glu Ile Ile His Asp Tyr Glu Leu Asn Thr Gly Lys Val Ile Ala Glu
135             140             145             150

ACC TTT CAG CAT CAT AAT TAC GAA CAG GTG CCG GGT GTG CTC GTG AAT       3928
Thr Phe Gln His His Asn Tyr Glu Gln Val Pro Gly Val Leu Val Asn
                155             160             165

AAT CAC GGA CCG TTC TGC TGG GGC ACT GAC GCC TTA AAT GCC ATT CAT       3976
Asn His Gly Pro Phe Cys Trp Gly Thr Asp Ala Leu Asn Ala Ile His
            170             175             180

AAC GCA GTT GTA TTA GAA ACG GTT GCC GAA ATG GCC TAT CAC TCC ATT       4024
Asn Ala Val Val Leu Glu Thr Val Ala Glu Met Ala Tyr His Ser Ile
        185             190             195

ATG CTG AAC AAG GAT GTA ACC CCA ATC AAT ACA GTC CTG CAT GAA AAG       4072
Met Leu Asn Lys Asp Val Thr Pro Ile Asn Thr Val Leu His Glu Lys
200             205             210

CAT TTT TAT CGA AAA CAC GGA GCA AAT GCG TAT TAT GGC CAG TCA TGA       4120
His Phe Tyr Arg Lys His Gly Ala Asn Ala Tyr Tyr Gly Gln Ser  *
215             220             225             230

TACGCCTGTG TCACCGGCTG GCATTCTGAT TGACTTGGAC GGTACTGTAT TCAGAGGAAA     4180
TGAGTTGATC GAAGGAGCAA GAGAAGCGAT CAAAACGCTT AGGAGAATGG GAAAGAAAAT     4240
CGTCTTTTTA AGCAACCGGG GGAATATCTC CCGTGCCATG TGCAGAAAAA AACTTCTTGG     4300
CGCGGGGATT GAAACGGACG TAAACGACAT TGTTCTGTCA TCAAGCGTGA CAGCGGCTTT     4360
TCTGAAAAAA CATTATCGTT TTTCAAAGGT ATGGGTGCTT GGGGAGCAAG GCTTGGTTGA     4420
CGAGCTGAGG CTGGCCGGTG TGCAGAACGC GAGCGAACCG AAGGAAGCGG ATTGGCTCGT     4480
GATCTCCCTT CATGAAACGC TCACGTACGA CGATTTAAAT CAAGCCTTTC AAGCGGCTGC     4540
CGGCGGCGCT CGTATTATCG CTACAAACAA AGACCGCTCT TTTCCGAACG AAGACGGAAA     4600
TGCCATTGAT GTGGCCGGAA TGATCGGGGC AATTGAGACT TCTGCACAAG CGAAGACTGA     4660
ACTTGTTGTC GGAAAACCGT CATGGCTGAT GGCGGAGGCT GCCTGTACGG CAATGGGGCT     4720
GTCCGCACAT GAATGCATGA TTATAGGAGA CAGCATTGAA TCTGACATTG CGATGGGGAA     4780
GCTTTATGGC ATGAAAAGCG CCTTAGTGCT AACTGGTTCT GCGAAACAGG GTGAACAGCG     4840
TTTGTACACG CCGGATTATG TGCTGGATTC TATTAAGGAT GTAACCAAAT TGGCTGAGGA     4900

GGGGATTCTG AT ATG AAT CGT ATC GCA GCT GAC GTT CAG CGT GCT TTT        4948
              Met Asn Arg Ile Ala Ala Asp Val Gln Arg Ala Phe
              1               5                   10

GAA AAC GCC GGA GAA AAG ACG TTG CCT ATA AAA GTT GAA GAA ATT GTT       4996
Glu Asn Ala Gly Glu Lys Thr Leu Pro Ile Lys Val Glu Glu Ile Val
        15              20              25

CTC GGT AAG CAA GCA GCT GAT TCG CTT TTG GAT TAT GTA AAA CGA AAA       5044
Leu Gly Lys Gln Ala Ala Asp Ser Leu Leu Asp Tyr Val Lys Arg Lys
30              35              40

AAC AAT CAA CAT ATT GTC CTT GTC TGC GAC GCG AAT ACA CAC CGC ATT       5092
Asn Asn Gln His Ile Val Leu Val Cys Asp Ala Asn Thr His Arg Ile
45              50              55              60

GCA GGA ATT GAT TTA GAA AAC CGA CTG AAT CAA GAA GGA TTT CAG GCC       5140
Ala Gly Ile Asp Leu Glu Asn Arg Leu Asn Gln Glu Gly Phe Gln Ala
            65              70              75

GAG TGC CTG ATC ATT CCA GAA AAT GAA GCC GGA GAT GTG ACA GCT GAT       5188
Glu Cys Leu Ile Ile Pro Glu Asn Glu Ala Gly Asp Val Thr Ala Asp
        80              85              90

GAA CGA TCG CTC ATT CAT GTG CTG ATC CAT ACG AAA CAA CCA ACG GAT       5236
```

```
                                                              -continued

Glu Arg Ser Leu Ile His Val Leu Ile His Thr Lys Gln Pro Thr Asp
         95                 100                 105

GTC ATG ATC GCA GTC GGT TCG GGC ACG ATT CAT GAT ATC GTC CGC TTT         5284
Val Met Ile Ala Val Gly Ser Gly Thr Ile His Asp Ile Val Arg Phe
        110                 115                 120

GCG GCG TTT CAA AGA GAT TTG CCG TTT ATT TCT TAT CCG ACT GCT CCA         5332
Ala Ala Phe Gln Arg Asp Leu Pro Phe Ile Ser Tyr Pro Thr Ala Pro
125                 130                 135                 140

TCT GTA GAC GGT TTT ACA TCA GCC GGT GCG CCG ATT ATT TTA TAC GGC         5380
Ser Val Asp Gly Phe Thr Ser Ala Gly Ala Pro Ile Ile Leu Tyr Gly
                145                 150                 155

ACG AAA ACA ACC ATT CAA ACG AAG GCC CCA TCT GCG CTG TTC GCT GAT         5428
Thr Lys Thr Thr Ile Gln Thr Lys Ala Pro Ser Ala Leu Phe Ala Asp
            160                 165                 170

CTG GAT CTA TTA AAA GCG GCA CCG CAG TCA ATG GTG GCG GCT GGC TTT         5476
Leu Asp Leu Leu Lys Ala Ala Pro Gln Ser Met Val Ala Ala Gly Phe
        175                 180                 185

GGT GAC ATG CTC GGT AAA ATC ACG TCT TTA GCA GAT TGG GAA ATA TCC         5524
Gly Asp Met Leu Gly Lys Ile Thr Ser Leu Ala Asp Trp Glu Ile Ser
        190                 195                 200

CGG CAT CTT GCC GGT GAG CCT TAT TCG CCT GCA GGA GCT AAG ATC GTT         5572
Arg His Leu Ala Gly Glu Pro Tyr Ser Pro Ala Gly Ala Lys Ile Val
205                 210                 215                 220

CAG GAG GCG CTT GCT GCC TGC ATT GAA CAC ACA GAA GAC ATT GCG ATG         5620
Gln Glu Ala Leu Ala Ala Cys Ile Glu His Thr Glu Asp Ile Ala Met
                225                 230                 235

AAA ACG GAA ACT GGC ATA CGG GTT TTG ATG GAG TCT TTA CTT GTA TCG         5668
Lys Thr Glu Thr Gly Ile Arg Val Leu Met Glu Ser Leu Leu Val Ser
            240                 245                 250

GGG CTT GTC ATG CTG GCT TTA GAT CAT TCC CGA CCG GCA TCA GGC GGC         5716
Gly Leu Val Met Leu Ala Leu Asp His Ser Arg Pro Ala Ser Gly Gly
        255                 260                 265

GAG CAT CAT ATT TCA CAT TGG ATT GAA ATG GAG TTA ATG GAG AAA AAA         5764
Glu His His Ile Ser His Trp Ile Glu Met Glu Leu Met Glu Lys Lys
        270                 275                 280

CGG CCT CAG ATT CTT CAT GGG GCA AAG GTG GGC TGT GCC GCT GTT TTA         5812
Arg Pro Gln Ile Leu His Gly Ala Lys Val Gly Cys Ala Ala Val Leu
285                 290                 295                 300

TTA ACT GAC ACA TAC AGA AAG CTC GCT CAG GAT GAC GGG CTG AAC GAA         5860
Leu Thr Asp Thr Tyr Arg Lys Leu Ala Gln Asp Asp Gly Leu Asn Glu
                305                 310                 315

TTT TCA CCA AGC CGC CGG GAA GCC ATC CAA TCG GCT TAT CAA ACA CTC         5908
Phe Ser Pro Ser Arg Arg Glu Ala Ile Gln Ser Ala Tyr Gln Thr Leu
            320                 325                 330

CCG AGA GGA GAA GTG CTG GCT GAT TGG CTG AGA TCA GCC GGA GGC CCT         5956
Pro Arg Gly Glu Val Leu Ala Asp Trp Leu Arg Ser Ala Gly Gly Pro
        335                 340                 345

GCT GAT TTT GAC GAA ATC GGT GTC GGG CAG GAT TCC GTC AAA AAT GCC         6004
Ala Asp Phe Asp Glu Ile Gly Val Gly Gln Asp Ser Val Lys Asn Ala
        350                 355                 360

TTC AGA CAC GCG CAC ACC TTA AGA GAC CGA TGC ACC GGA TTA AGA ATC         6052
Phe Arg His Ala His Thr Leu Arg Asp Arg Cys Thr Gly Leu Arg Ile
365                 370                 375                 380

ATC AAT GAA AAC AAA ACG CTG ATC AAC CAT GGT CTA TAT GAA TAG             6097
Ile Asn Glu Asn Lys Thr Leu Ile Asn His Gly Leu Tyr Glu *
                385                 390                 395

CCCGCACCTC GAATGGAAGG GGTAACGCAG ATG AAA AAA ATG ACT GTC TGT TTT        6151
                                 Met Lys Lys Met Thr Val Cys Phe
                                  1                   5
```

```
CTT GTG CTC ATG ATG TTG CTG ACA TTA GTC ATT GCC GGG TGT TCA GCA      6199
Leu Val Leu Met Met Leu Leu Thr Leu Val Ile Ala Gly Cys Ser Ala
     10              15                  20

GAA AAA TCA TCC GGC AAA TCG GGT GAA ACT GAG CTG ACC TTT TGG ACA      6247
Glu Lys Ser Ser Gly Lys Ser Gly Glu Thr Glu Leu Thr Phe Trp Thr
 25              30                  35                          40

TTT AAC GGG CTT CAT GAG CAG TTC TAT GTG GAA ATG GTG AAG GAA TGG      6295
Phe Asn Gly Leu His Glu Gln Phe Tyr Val Glu Met Val Lys Glu Trp
                 45                  50                  55

AAC AAA AAA TAT CCT GAC CGC AAA ATT AAG CTG AAT ACG GTC GTT TAT      6343
Asn Lys Lys Tyr Pro Asp Arg Lys Ile Lys Leu Asn Thr Val Val Tyr
             60                  65                  70

CCA TAT GGA CAA ATG CAC GAT AAC TTA TCT ATC TCC CTA ATA GCG GGA      6391
Pro Tyr Gly Gln Met His Asp Asn Leu Ser Ile Ser Leu Ile Ala Gly
         75                  80                  85

GAA GGC GTT CCT GAT ATT GCA GAT GTC GAA TTG GCC CGT TTT TCA AAC      6439
Glu Gly Val Pro Asp Ile Ala Asp Val Glu Leu Ala Arg Phe Ser Asn
     90                  95                 100

TTT TTG AAG GGC TCT GAC ATA CCG CTT GCC GAC TTG ACT CCG CTG ATT      6487
Phe Leu Lys Gly Ser Asp Ile Pro Leu Ala Asp Leu Thr Pro Leu Ile
105             110                 115                 120

GAA AAG GAT CGC GAT AAA TTC GTT GAG GCG CGG CTG ACA TTG TAC AGC      6535
Glu Lys Asp Arg Asp Lys Phe Val Glu Ala Arg Leu Thr Leu Tyr Ser
                125                 130                 135

AAA AAC GGA AAG CTT TAC GGA CTC GAT ACA CAT GTA GGG ACA ACG GTC      6583
Lys Asn Gly Lys Leu Tyr Gly Leu Asp Thr His Val Gly Thr Thr Val
            140                 145                 150

ATG TTT TAT AAC ATG GAT GTG ATG AAA AAA GCC GGC GTC AAT CCT GAC      6631
Met Phe Tyr Asn Met Asp Val Met Lys Lys Ala Gly Val Asn Pro Asp
        155                 160                 165

GAT ATT AAA ACA TGG GAT GAT TAC CAT AAA GCC GGA CAG AAA GTG CGC      6679
Asp Ile Lys Thr Trp Asp Asp Tyr His Lys Ala Gly Gln Lys Val Arg
    170                 175                 180

AAA GTG ACC GGG AAG CCG ATG GGA ACG GTG GAA ACA AAT GAT TCC GCA      6727
Lys Val Thr Gly Lys Pro Met Gly Thr Val Glu Thr Asn Asp Ser Ala
185                 190                 195                 200

ACG TTC TTA TCT ATG ATT TCA CAG CAA AAC TCA GGC TAT TTT GAT AAA      6775
Thr Phe Leu Ser Met Ile Ser Gln Gln Asn Ser Gly Tyr Phe Asp Lys
                205                 210                 215

AAC GGC AAG CTG ATC CTC AAT AAT GAC ACC AAC GTA AAA ACA CTT CAA      6823
Asn Gly Lys Leu Ile Leu Asn Asn Asp Thr Asn Val Lys Thr Leu Gln
            220                 225                 230

TAT TTA AAA GAC ATG ATC AAT GAT AAA ACG ATG ATT CCT GCG CCG GGC      6871
Tyr Leu Lys Asp Met Ile Asn Asp Lys Thr Met Ile Pro Ala Pro Gly
        235                 240                 245

GGC GGG CAT CAC AGT GAA GAA TAC TAC GGC TTT ATG AAC CAA GGA GGA      6919
Gly Gly His His Ser Glu Glu Tyr Tyr Gly Phe Met Asn Gln Gly Gly
    250                 255                 260

GCT GCT TCA GTT CTC ATG CCG ATT TGG TAT ATG GGA AGA TTT ATC GAT      6967
Ala Ala Ser Val Leu Met Pro Ile Trp Tyr Met Gly Arg Phe Ile Asp
265                 270                 275                 280

TAT ATG CCT GAT CTG AAA GGG AAG ATT GCC ATC AGA CCG CTC CCG GCA      7015
Tyr Met Pro Asp Leu Lys Gly Lys Ile Ala Ile Arg Pro Leu Pro Ala
                285                 290                 295

TGG AAA GAG GGG GGC GAC CGC TCG GCA GGT TTG GGC GGT ACG GCA ACT      7063
Trp Lys Glu Gly Gly Asp Arg Ser Ala Gly Leu Gly Gly Thr Ala Thr
            300                 305                 310

GTT GTA CCG AAG CAA TCC AAG CAT GTT GAG TTA GCA AAA GAG TTT TTG      7111
Val Val Pro Lys Gln Ser Lys His Val Glu Leu Ala Lys Glu Phe Leu
        315                 320                 325
```

-continued

```
GCC TTT GCG AAG GGC TCT GAA GAA GGA AAT AAA AAA CTC TGG AGC GTA      7159
Ala Phe Ala Lys Gly Ser Glu Glu Gly Asn Lys Lys Leu Trp Ser Val
330             335                 340

CTC GGC TTT GAC CCG CTT CGC TGG GAT GTT TGG AGC TCC AAG GAA TTG      7207
Leu Gly Phe Asp Pro Leu Arg Trp Asp Val Trp Ser Ser Lys Glu Leu
345             350                 355                 360

AAA GAG AAA AAC AAA TAC ACG GAT TAC TTC CAA AAC GGA ACA GGC ATT      7255
Lys Glu Lys Asn Lys Tyr Thr Asp Tyr Phe Gln Asn Gly Thr Gly Ile
                365                 370                 375

TTT TCT GTG CTG CTC GAT ATC AAG GAT GAA ATC AAT CCA ATT TAT TTA      7303
Phe Ser Val Leu Leu Asp Ile Lys Asp Glu Ile Asn Pro Ile Tyr Leu
            380                 385                 390

CAT GAG GAT TTT GCC AAG GCT TCA GAC CTT GTC AAC AGA AGC GTA TTG      7351
His Glu Asp Phe Ala Lys Ala Ser Asp Leu Val Asn Arg Ser Val Leu
        395                 400                 405

TTC GAC GCG CTT AAA TCT CAG CAA AAA ACG CCT AAA CAA GCC TTG GAC      7399
Phe Asp Ala Leu Lys Ser Gln Gln Lys Thr Pro Lys Gln Ala Leu Asp
    410                 415                 420

AGA GCG GCA GGT GAA CTG AAA CAG AAA TAG AATCCCATTC AAAAAGTGAA        7449
Arg Ala Ala Gly Glu Leu Lys Gln Lys *
425                 430

AGCGGGGAGG TTCTC ATG AAA CCT GTG AAA ACG GGA ACG GTT CAT CCC GTT     7500
                 Met Lys Pro Val Lys Thr Gly Thr Val His Pro Val
                 1               5                   10

CCT TCA GCT GCG AAA CAA TCA GGC TGG CGA GAT CTG TTT TAT TCA AAA      7548
Pro Ser Ala Ala Lys Gln Ser Gly Trp Arg Asp Leu Phe Tyr Ser Lys
            15                  20                  25

AAA GCG GCG CCC TAT CTG TTT ACA GCG CCA TTC GTT TTA TCC TTT CTC      7596
Lys Ala Ala Pro Tyr Leu Phe Thr Ala Pro Phe Val Leu Ser Phe Leu
        30                  35                  40

GTA TTT TTT CTA TAC CCC ATC ATT AGT GTC TTC ATC ATG AGC TTC CAA      7644
Val Phe Phe Leu Tyr Pro Ile Ile Ser Val Phe Ile Met Ser Phe Gln
    45                  50                  55                  60

AGA ATT TTG CCG GGA GAG GTG TCC TTT GTC GGA TTG TCT AAT TAT ACA      7692
Arg Ile Leu Pro Gly Glu Val Ser Phe Val Gly Leu Ser Asn Tyr Thr
                65                  70                  75

GCG CTA AAC AAC CCG ACG TTC TAT ACC GCC CTT TGG AAT ACG CTG GAA      7740
Ala Leu Asn Asn Pro Thr Phe Tyr Thr Ala Leu Trp Asn Thr Leu Glu
            80                  85                  90

TAC ACC TTT TGG ACG CTG ATC GTG CTG ATT CCT GTT CCA TTG CTT CTG      7788
Tyr Thr Phe Trp Thr Leu Ile Val Leu Ile Pro Val Pro Leu Leu Leu
        95                  100                 105

GCC ATA TTC CTG AAT TCA AAG CTG GTC AAA TTT AGA AAT ATA TTT AAA      7836
Ala Ile Phe Leu Asn Ser Lys Leu Val Lys Phe Arg Asn Ile Phe Lys
    110                 115                 120

TCA GCA TTA TTT ATC CCG GCA TTG ACC TCA ACC ATT GTC GCG GGG ATC      7884
Ser Ala Leu Phe Ile Pro Ala Leu Thr Ser Thr Ile Val Ala Gly Ile
125                 130                 135                 140

ATT TTT CGG CTG ATC TTC GGA GAA ATG GAA ACG TCT CTG GCC AAT TCC      7932
Ile Phe Arg Leu Ile Phe Gly Glu Met Glu Thr Ser Leu Ala Asn Ser
                145                 150                 155

ATC CTA CTT AAA CTC GGC TTT TCA CCT CAG AAC TGG ATG AAC AAT GAA      7980
Ile Leu Leu Lys Leu Gly Phe Ser Pro Gln Asn Trp Met Asn Asn Glu
            160                 165                 170

CAT ACC GGC ATG TTT TTG ATG GTG CTG CTT GCT TCA TGG AAA TGG ATG      8028
His Thr Gly Met Phe Leu Met Val Leu Leu Ala Ser Trp Lys Trp Met
        175                 180                 185

GGA ATC AAC ATC CTT TAC TTT TTA GCA GGT TTG CAA AAT GTG CCG AAA      8076
Gly Ile Asn Ile Leu Tyr Phe Leu Ala Gly Leu Gln Asn Val Pro Lys
```

-continued

```
      190                 195                 200
GAG CTG TAC GAA GCC GCT GAT ATA GAC GGC GCG AAT ACA ATG AAA AAA      8124
Glu Leu Tyr Glu Ala Ala Asp Ile Asp Gly Ala Asn Thr Met Lys Lys
205                 210                 215                 220

TTT CTG CAC ATC ACG CTG CCG TTT CTC AAG CCT GTA ACC GTA TAT GTG      8172
Phe Leu His Ile Thr Leu Pro Phe Leu Lys Pro Val Thr Val Tyr Val
                225                 230                 235

CTG ACC ATC AGC ATC ATC GGC GGC TTC AGG ATG TTT GAG GAA AGC TAC      8220
Leu Thr Ile Ser Ile Ile Gly Gly Phe Arg Met Phe Glu Glu Ser Tyr
            240                 245                 250

GTC CTT TGG CAG AAT AAT TCC CCG GGT AAT ATT GGT CTG ACG CTT GTC      8268
Val Leu Trp Gln Asn Asn Ser Pro Gly Asn Ile Gly Leu Thr Leu Val
        255                 260                 265

GGA TAT TTG TAT CAG CAG GGA CTT GCC TAC AAT GAA ATG GGA TAC GGA      8316
Gly Tyr Leu Tyr Gln Gln Gly Leu Ala Tyr Asn Glu Met Gly Tyr Gly
    270                 275                 280

GCG GCC ATC GGC ATT GTG CTT TTG ATT GTG ATC CTT GTT GTC AGC CTG      8364
Ala Ala Ile Gly Ile Val Leu Leu Ile Val Ile Leu Val Val Ser Leu
285                 290                 295                 300

ATT TCA TTA AAG CTG TCA GGC TCG TTT AAG GGG GAG GGA TAA ATG TTG      8412
Ile Ser Leu Lys Leu Ser Gly Ser Phe Lys Gly Glu Gly  *  Met Leu
                305                 310                      1

CGG CAC AGT CCT CAG TTT AGC GTT TAT AGA ATT GCG CTG ACC CTG TTT      8460
Arg His Ser Pro Gln Phe Ser Val Tyr Arg Ile Ala Leu Thr Leu Phe
            5                   10                  15

TTT ATG ATG CTG AGC CTA TTG TAT CTT TTT CCG ATT TTC TGT TTG CTT      8508
Phe Met Met Leu Ser Leu Leu Tyr Leu Phe Pro Ile Phe Cys Leu Leu
        20                  25                  30

TTA GGA TCA TTA AAG CCG TCA TCT GAG CTT TTG CGT GTG GGG CTG AAT      8556
Leu Gly Ser Leu Lys Pro Ser Ser Glu Leu Leu Arg Val Gly Leu Asn
35                  40                  45                  50

CTT GAT ATT GAT CCA AAA GTG ATG AGT TTT GAT AAC TAC ACA TTT CTG      8604
Leu Asp Ile Asp Pro Lys Val Met Ser Phe Asp Asn Tyr Thr Phe Leu
                55                  60                  65

TTT AAT GGC GGC AGC ATT TAT TTC AAA TGG TTT TTT AAC AGT CTT GTA      8652
Phe Asn Gly Gly Ser Ile Tyr Phe Lys Trp Phe Phe Asn Ser Leu Val
            70                  75                  80

CTC GGA CTT TTT ACG ACT GTG CTC ACT CTG TTT TTT TCT TCG ATG ATC      8700
Leu Gly Leu Phe Thr Thr Val Leu Thr Leu Phe Phe Ser Ser Met Ile
        85                  90                  95

GGG TAC GGG CTT GCG GTT TAT GAT TTT AAG GGC AGA AAT ATC ATC TTT      8748
Gly Tyr Gly Leu Ala Val Tyr Asp Phe Lys Gly Arg Asn Ile Ile Phe
    100                 105                 110

GTT CTT GTG CTG ATT ATT ATG ATG GTT CCG CTG GAA GTG ATG ATG CTT      8796
Val Leu Val Leu Ile Ile Met Met Val Pro Leu Glu Val Met Met Leu
115                 120                 125                 130

CCT CTG TTT AAA CTT ACT GTC GGA CTG CAC TTG ATC GAT TCA TAT ACG      8844
Pro Leu Phe Lys Leu Thr Val Gly Leu His Leu Ile Asp Ser Tyr Thr
                135                 140                 145

GGT GTC ATA TTG CCG TTT ATC GTT TCA CCT GTT GCT GTT TTC TTT TTC      8892
Gly Val Ile Leu Pro Phe Ile Val Ser Pro Val Ala Val Phe Phe Phe
            150                 155                 160

AGG CAA TAT GCT CTT GGC CTT CCA AGA GAT CTG CTG GAC TCT GCA AGG      8940
Arg Gln Tyr Ala Leu Gly Leu Pro Arg Asp Leu Leu Asp Ser Ala Arg
        165                 170                 175

ATG GAC GGC TGT ACG GAA TTC GGC ATC TTT TTC AGG ATT ATG GCA CCG      8988
Met Asp Gly Cys Thr Glu Phe Gly Ile Phe Phe Arg Ile Met Ala Pro
    180                 185                 190

CTG ATG AAA CCG GCT TTC GGT GCG ATG ATT ATC CTT CAG TCC TTA AAC      9036
```

```
Leu Met Lys Pro Ala Phe Gly Ala Met Ile Ile Leu Gln Ser Leu Asn
195                 200                 205                 210

AGC TGG AAC AAC TTC TTG TGG CCG CTG ATT GTG CTT CGG TCG AAA GAA       9084
Ser Trp Asn Asn Phe Leu Trp Pro Leu Ile Val Leu Arg Ser Lys Glu
                215                 220                 225

ATG TTT ACG CTT CCA ATA GGG CTG TCC AGC TTG CTG AGC CCT TAT GGA       9132
Met Phe Thr Leu Pro Ile Gly Leu Ser Ser Leu Leu Ser Pro Tyr Gly
            230                 235                 240

AAT AAT TAC GAC ATG CTT ATA TCC GGC TCA GTA TTT GCG ATT TTG CCG       9180
Asn Asn Tyr Asp Met Leu Ile Ser Gly Ser Val Phe Ala Ile Leu Pro
            245                 250                 255

GTG ATT ATC ATT TTC TTG TTT TTC CAA AAG TAC TTT ATC TCC GGC CTG       9228
Val Ile Ile Ile Phe Leu Phe Phe Gln Lys Tyr Phe Ile Ser Gly Leu
260                 265                 270

ACG GTA GGG GGA GTC AAA GGT TAA TGA AGGAGGAAAC GTGTG ATG AAA AAA      9279
Thr Val Gly Gly Val Lys Gly  *   *                   Met Lys Lys
275                 280                                  1

GCG CGA ATG ATT GTA GAC AAA GAA TAT AAA ATC GGT GAA GTA GAT AAA       9327
Ala Arg Met Ile Val Asp Lys Glu Tyr Lys Ile Gly Glu Val Asp Lys
        5                   10                  15

CGG ATT TAT GGC TCG TTT ATC GAA CAT ATG GGT CGT GCG GTA TAT GAA       9375
Arg Ile Tyr Gly Ser Phe Ile Glu His Met Gly Arg Ala Val Tyr Glu
 20                  25                  30                  35

GGC ATA TAC GAG CCT GAT CAC CCT GAA GCG GAT GAA GAT GGA TTT AGA       9423
Gly Ile Tyr Glu Pro Asp His Pro Glu Ala Asp Glu Asp Gly Phe Arg
                40                  45                  50

AAA GAT GTC CAG TCG CTG ATC AAA GAA TTA CAG GTT CCC ATC ATC CGC       9471
Lys Asp Val Gln Ser Leu Ile Lys Glu Leu Gln Val Pro Ile Ile Arg
            55                  60                  65

TAT CCG GGC GGA AAC TTT TTA TCC GGA TAC AAC TGG GAG GAC GGT GTC       9519
Tyr Pro Gly Gly Asn Phe Leu Ser Gly Tyr Asn Trp Glu Asp Gly Val
        70                  75                  80

GGA CCA GTC GAA AAC CGC CCG AGA CGG CTT GAC TTG GCA TGG CAA ACG       9567
Gly Pro Val Glu Asn Arg Pro Arg Arg Leu Asp Leu Ala Trp Gln Thr
    85                  90                  95

ACA GAA ACC AAT GAA GTG GGA ACA AAT GAA TTT TTA TCT TGG GCA AAA       9615
Thr Glu Thr Asn Glu Val Gly Thr Asn Glu Phe Leu Ser Trp Ala Lys
100                 105                 110                 115

AAG GTG AAC ACT GAG GTC AAT ATG GCC GTC AAC CTT GGC ACA AGA GGC       9663
Lys Val Asn Thr Glu Val Asn Met Ala Val Asn Leu Gly Thr Arg Gly
                120                 125                 130

ATA GAT GCC GCC CGT AAT CTC GTT GAA TAT TGC AAC CAT CCG AAA GGC       9711
Ile Asp Ala Ala Arg Asn Leu Val Glu Tyr Cys Asn His Pro Lys Gly
            135                 140                 145

TCT TAC TGG AGT GAT TTA AGA AGA TCG CAT GGC TAT GAA CAG CCG TAT       9759
Ser Tyr Trp Ser Asp Leu Arg Arg Ser His Gly Tyr Glu Gln Pro Tyr
        150                 155                 160

GGC ATC AAA ACA TGG TGC TTA GGA AAC GAA ATG GAT GGA CCA TGG CAG       9807
Gly Ile Lys Thr Trp Cys Leu Gly Asn Glu Met Asp Gly Pro Trp Gln
    165                 170                 175

ATC GGC CAC AAA ACA GCT GAT GAA TAC GGA CGG CTT GCC GCA GAG ACA       9855
Ile Gly His Lys Thr Ala Asp Glu Tyr Gly Arg Leu Ala Ala Glu Thr
180                 185                 190                 195

GCA AAG GTC ATG AAG TGG GTT GAC CCA TCA ATT GAA CTC GTT GCC TGC       9903
Ala Lys Val Met Lys Trp Val Asp Pro Ser Ile Glu Leu Val Ala Cys
                200                 205                 210

GGC AGC TCA AAC AGC GGT ATG CCG ACC TTT ATC GAT TGG GAA GCG AAG       9951
Gly Ser Ser Asn Ser Gly Met Pro Thr Phe Ile Asp Trp Glu Ala Lys
            215                 220                 225
```

```
GTG CTT GAG CAT ACG TAT GAG CAT GTC GAC TAT ATC TCT CTT CAC ACT        9999
Val Leu Glu His Thr Tyr Glu His Val Asp Tyr Ile Ser Leu His Thr
    230                 235                 240

TAC TAC GGA AAC CGG GAT AAC AAT CTG CCA AAC TAC TTG GCA CGT TCT       10047
Tyr Tyr Gly Asn Arg Asp Asn Asn Leu Pro Asn Tyr Leu Ala Arg Ser
245                 250                 255

ATG GAT TTG GAT CAT TTT ATC AAA TCA GTC GCT GCG ACC TGT GAC TAT       10095
Met Asp Leu Asp His Phe Ile Lys Ser Val Ala Ala Thr Cys Asp Tyr
260                 265                 270                 275

GTA AAA GCA AAA ACA CGC AGC AAG AAA ACT ATC AAT CTC TCT CTG GAT       10143
Val Lys Ala Lys Thr Arg Ser Lys Lys Thr Ile Asn Leu Ser Leu Asp
                280                 285                 290

GAA TGG AAC GTC TGG TAC CAC TCA AAT GAG GCT GAT AAA AAA GTC GAG       10191
Glu Trp Asn Val Trp Tyr His Ser Asn Glu Ala Asp Lys Lys Val Glu
            295                 300                 305

CCG TGG ATC ACT GCG CGT CCG ATT TTA GAG GAT ATT TAC AAT TTT GAA       10239
Pro Trp Ile Thr Ala Arg Pro Ile Leu Glu Asp Ile Tyr Asn Phe Glu
            310                 315                 320

GAT GCC TTA TTA GTC GGC TCT CTG CTC ATT ACG ATG CTG CAG CAC GCA       10287
Asp Ala Leu Leu Val Gly Ser Leu Leu Ile Thr Met Leu Gln His Ala
    325                 330                 335

GAC CGT GTG AAA ATT GCG TGT CTT GCA CAG CTT GTT AAT GTC ATC GCG       10335
Asp Arg Val Lys Ile Ala Cys Leu Ala Gln Leu Val Asn Val Ile Ala
340                 345                 350                 355

CCG ATC ATG ACG GAA AAA GGC GGA GAA GCA TGG AGA CAG CCG ATT TTC       10383
Pro Ile Met Thr Glu Lys Gly Gly Glu Ala Trp Arg Gln Pro Ile Phe
                360                 365                 370

TAT CCA TAC ATG CAT GCT TCT GTT TAC GGA AGG GGC GAG TCA CTG AAA       10431
Tyr Pro Tyr Met His Ala Ser Val Tyr Gly Arg Gly Glu Ser Leu Lys
            375                 380                 385

CCG CTT ATT TCT TCT CCT AAG TAC GAT TGT TCT GAT TTC ACT GAT GTG       10479
Pro Leu Ile Ser Ser Pro Lys Tyr Asp Cys Ser Asp Phe Thr Asp Val
            390                 395                 400

CCA TAT GTT GAT GCT GCT GTT GTG TAC TCT GAA GAG GAA GAA ACA CTC       10527
Pro Tyr Val Asp Ala Ala Val Val Tyr Ser Glu Glu Glu Glu Thr Leu
    405                 410                 415

ACT ATT TTT GCG GTA AAC AAG GCT GAG GAT CAG ATG GAG ACG GAG ATT       10575
Thr Ile Phe Ala Val Asn Lys Ala Glu Asp Gln Met Glu Thr Glu Ile
420                 425                 430                 435

TCG CTC AGA GGC TTT GAA TCC TAC CAA ATC GCA GAG CAC ATC GTA CTT       10623
Ser Leu Arg Gly Phe Glu Ser Tyr Gln Ile Ala Glu His Ile Val Leu
                440                 445                 450

GAG CAT CAG GAT ATC AAA GCA ACA AAC CAG CAT AAC AGA AAA AAT GTC       10671
Glu His Gln Asp Ile Lys Ala Thr Asn Gln His Asn Arg Lys Asn Val
            455                 460                 465

GTT CCG CAT TCC AAC GGA TCA TCG TCT GTC AGC GAA AAC GGC TTA ACT       10719
Val Pro His Ser Asn Gly Ser Ser Ser Val Ser Glu Asn Gly Leu Thr
            470                 475                 480

GCT CAT TTC ACG CCG CTT TCC TGG AAT GTG ATC CGC CTG AAA AAA CAG       10767
Ala His Phe Thr Pro Leu Ser Trp Asn Val Ile Arg Leu Lys Lys Gln
    485                 490                 495

TCA TAA GAATAGCAAA GCCGGAGATT TCTCTCCGGC TTGTCTTTCA ACTGCCACGA        10823
Ser *
500

GCCGGCCCAT TCCAGCCGGC TTTTTGTATA GGAAAAAATG ACCGCTTTTC ACCATGAAAT    10883

TATGATATAT TTATGAAAAA CAGAAAAGGG GATG                                10917

(2) INFORMATION FOR SEQ ID NO:12:
```

(i) SEQUENCE CHARACTERISTICS:
    (A) LENGTH: 496 amino acids
    (B) TYPE: amino acid
    (D) TOPOLOGY: linear (ii) MOLECULE TYPE: protein (vi) ORIGINAL SOURCE:
    (A) ORGANISM: Bacillus subtilis (ix) FEATURE:
    (D) OTHER INFORMATION: /product= "araA"

(xi) SEQUENCE DESCRIPTION: SEQ ID NO:12:

```
Met Leu Gln Thr Lys Asp Tyr Glu Phe Trp Phe Val Thr Gly Ser Gln
 1               5                  10                  15

His Leu Tyr Gly Glu Glu Thr Leu Glu Leu Val Asp Gln His Ala Lys
             20                  25                  30

Ser Ile Cys Glu Gly Leu Ser Gly Ile Ser Ser Arg Tyr Lys Ile Thr
         35                  40                  45

His Lys Pro Val Val Thr Ser Pro Glu Thr Ile Arg Glu Leu Leu Arg
     50                  55                  60

Glu Ala Glu Tyr Ser Glu Thr Cys Ala Gly Ile Ile Thr Trp Met His
65                  70                  75                  80

Thr Phe Ser Pro Ala Lys Met Trp Ile Glu Gly Leu Ser Ser Tyr Gln
                 85                  90                  95

Lys Pro Leu Met His Leu His Thr Gln Tyr Asn Arg Asp Ile Pro Trp
            100                 105                 110

Gly Thr Ile Asp Met Asp Phe Met Asn Ser Asn Gln Ser Ala His Gly
        115                 120                 125

Asp Arg Glu Tyr Gly Tyr Ile Asn Ser Arg Met Gly Leu Ser Arg Lys
    130                 135                 140

Val Ile Ala Gly Tyr Trp Asp Asp Glu Val Lys Lys Glu Met Ser
145                 150                 155                 160

Gln Trp Met Asp Thr Ala Ala Leu Asn Glu Ser Arg His Ile Lys
                165                 170                 175

Val Ala Arg Phe Gly Asp Asn Met Arg His Val Ala Val Thr Asp Gly
            180                 185                 190

Asp Lys Val Gly Ala His Ile Gln Phe Gly Trp Gln Val Asp Gly Tyr
        195                 200                 205

Gly Ile Gly Asp Leu Val Glu Val Met Asp Arg Ile Thr Asp Asp Glu
    210                 215                 220

Val Asp Thr Leu Tyr Ala Glu Tyr Asp Arg Leu Tyr Val Ile Ser Glu
225                 230                 235                 240

Glu Thr Lys Arg Asp Glu Ala Lys Val Ala Ser Ile Lys Glu Gln Ala
                245                 250                 255

Lys Ile Glu Leu Gly Leu Thr Ala Phe Leu Glu Gln Gly Gly Tyr Thr
            260                 265                 270

Ala Phe Thr Thr Ser Phe Glu Val Leu His Gly Met Lys Gln Leu Pro
        275                 280                 285

Gly Leu Ala Val Gln Arg Leu Met Glu Lys Gly Tyr Gly Phe Ala Gly
    290                 295                 300

Glu Gly Asp Trp Lys Thr Ala Ala Leu Val Arg Met Met Lys Ile Met
305                 310                 315                 320

Ala Lys Gly Lys Arg Thr Ser Phe Met Glu Asp Tyr Thr Tyr His Phe
                325                 330                 335

Glu Pro Gly Asn Glu Met Ile Leu Gly Ser His Met Leu Glu Val Cys
```

```
                    340                 345                 350
Pro Thr Val Ala Leu Asp Gln Pro Lys Ile Glu Val His Ser Leu Ser
            355                 360                 365

Ile Gly Gly Lys Glu Asp Pro Ala Arg Leu Val Phe Asn Gly Ile Ser
370                 375                 380

Gly Ser Ala Ile Gln Ala Ser Ile Val Asp Ile Gly Gly Arg Phe Arg
385                 390                 395                 400

Leu Val Leu Asn Glu Val Asn Gly Gln Glu Ile Glu Lys Asp Met Pro
                405                 410                 415

Asn Leu Pro Val Ala Arg Val Leu Trp Lys Pro Glu Pro Ser Leu Lys
            420                 425                 430

Thr Ala Ala Glu Ala Trp Ile Leu Ala Gly Gly Ala His His Thr Cys
        435                 440                 445

Leu Ser Tyr Glu Leu Thr Ala Glu Gln Met Leu Asp Trp Ala Glu Met
    450                 455                 460

Ala Gly Ile Glu Ser Val Leu Ile Ser Arg Asp Thr Thr Ile His Lys
465                 470                 475                 480

Leu Lys His Glu Leu Lys Trp Asn Glu Ala Leu Tyr Arg Leu Gln Lys
                485                 490                 495
```

(2) INFORMATION FOR SEQ ID NO:13:

(i) SEQUENCE CHARACTERISTICS:
        (A) LENGTH: 560 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "araB"

(xi) SEQUENCE DESCRIPTION: SEQ ID NO:13:

```
Met Ala Tyr Thr Ile Gly Val Asp Phe Gly Thr Leu Ser Gly Arg Ala
1               5                   10                  15

Val Leu Val His Val Gln Thr Gly Glu Glu Leu Ala Ala Ala Val Lys
                20                  25                  30

Glu Tyr Arg His Ala Val Ile Asp Thr Val Leu Pro Lys Thr Gly Gln
            35                  40                  45

Lys Leu Pro Arg Asp Trp Ala Leu Gln His Pro Ala Asp Tyr Leu Glu
        50                  55                  60

Val Leu Glu Thr Thr Ile Pro Ser Leu Leu Glu Gln Thr Gly Val Asp
65                  70                  75                  80

Pro Lys Asp Ile Ile Gly Ile Gly Ile Asp Phe Thr Ala Cys Thr Ile
                85                  90                  95

Leu Pro Ile Asp Ser Ser Gly Gln Pro Leu Cys Met Leu Pro Glu Tyr
            100                 105                 110

Glu Glu Glu Pro His Ser Tyr Val Lys Leu Trp Lys His His Ala Ala
        115                 120                 125

Gln Lys His Ala Asp Arg Leu Asn Gln Ile Ala Glu Glu Gly Glu
    130                 135                 140

Ala Phe Leu Gln Arg Tyr Gly Gly Lys Ile Ser Ser Glu Trp Met Ile
145                 150                 155                 160

Pro Lys Val Met Gln Ile Ala Glu Glu Ala Pro His Ile Tyr Glu Ala
                165                 170                 175
```

```
Ala Asp Arg Ile Ile Glu Ala Ala Asp Trp Ile Val Tyr Gln Leu Cys
            180                 185                 190

Gly Ser Leu Lys Arg Ser Asn Cys Thr Ala Gly Tyr Lys Ala Met Trp
        195                 200                 205

Ser Glu Lys Ala Gly Tyr Pro Ser Asp Asp Phe Phe Glu Lys Leu Asn
        210                 215                 220

Pro Ser Met Lys Thr Ile Thr Lys Asp Lys Leu Ser Gly Ser Ile His
225                 230                 235                 240

Ser Val Gly Glu Lys Ala Gly Ser Leu Thr Glu Lys Met Ala Lys Leu
                245                 250                 255

Thr Gly Leu Leu Pro Gly Thr Ala Val Ala Val Ala Asn Val Asp Ala
                260                 265                 270

His Val Ser Val Pro Ala Val Gly Ile Thr Glu Pro Gly Lys Met Leu
            275                 280                 285

Met Ile Met Gly Thr Ser Thr Cys His Val Leu Leu Gly Glu Glu Val
            290                 295                 300

His Ile Val Pro Gly Met Cys Gly Val Val Asp Asn Gly Ile Leu Pro
305                 310                 315                 320

Gly Tyr Ala Gly Tyr Glu Ala Gly Gln Ser Cys Val Gly Asp His Phe
                325                 330                 335

Asp Trp Phe Val Lys Thr Cys Val Pro Pro Ala Tyr Gln Glu Glu Ala
                340                 345                 350

Lys Glu Lys Asn Ile Gly Val His Glu Leu Leu Ser Glu Lys Ala Asn
            355                 360                 365

His Gln Ala Pro Gly Glu Ser Gly Leu Leu Ala Leu Asp Trp Trp Asn
            370                 375                 380

Gly Asn Arg Ser Thr Leu Val Asp Ala Asp Leu Thr Gly Met Leu Leu
385                 390                 395                 400

Gly Met Thr Leu Leu Thr Lys Pro Glu Glu Ile Tyr Arg Ala Leu Val
                405                 410                 415

Glu Ala Thr Ala Tyr Gly Thr Arg Met Ile Ile Glu Thr Phe Lys Glu
                420                 425                 430

Ser Gly Val Pro Ile Glu Glu Leu Phe Ala Ala Gly Gly Ile Ala Glu
                435                 440                 445

Lys Asn Pro Phe Val Met Gln Ile Tyr Ala Asp Val Thr Asn Met Asp
450                 455                 460

Ile Lys Ile Ser Gly Ser Pro Gln Ala Pro Ala Leu Gly Ser Ala Ile
465                 470                 475                 480

Phe Gly Ala Leu Ala Ala Gly Lys Glu Lys Gly Gly Tyr Asp Asp Ile
                485                 490                 495

Lys Lys Ala Ala Ala Asn Met Gly Lys Leu Lys Asp Ile Thr Tyr Thr
                500                 505                 510

Pro Asn Ala Glu Asn Ala Ala Val Tyr Glu Lys Leu Tyr Ala Glu Tyr
            515                 520                 525

Lys Glu Leu Val His Tyr Phe Gly Lys Glu Asn His Val Met Lys Arg
            530                 535                 540

Leu Lys Thr Ile Lys Asn Leu Gln Phe Ser Ser Ala Ala Lys Lys Asn
545                 550                 555                 560

(2) INFORMATION FOR SEQ ID NO:14:

(i) SEQUENCE CHARACTERISTICS:
        (A) LENGTH: 229 amino acids
        (B) TYPE: amino acid
```

(D) TOPOLOGY: linear (ii) MOLECULE TYPE: protein (vi) ORIGINAL SOURCE:
          (A) ORGANISM: Bacillus subtilis (ix) FEATURE:
          (D) OTHER INFORMATION: /product= "araD"

(xi) SEQUENCE DESCRIPTION: SEQ ID NO:14:

Met Leu Glu Thr Leu Lys Lys Glu Val Leu Ala Ala Asn Leu Lys Leu
 1               5                  10                  15

Gln Glu His Gln Leu Val Thr Phe Thr Trp Gly Asn Val Ser Gly Ile
            20                  25                  30

Asp Arg Glu Lys Glu Arg Ile Val Ile Lys Leu Ala Glu Ser Asn Thr
        35                  40                  45

Ser Asp Leu Thr Ala Asp Asp Leu Val Val Leu Asn Leu Asp Gly Glu
    50                  55                  60

Val Val Glu Gly Ser Leu Lys Pro Ser Ser Asp Thr Pro Thr His Val
65                  70                  75                  80

Tyr Leu Tyr Lys Ala Phe Pro Asn Ile Gly Gly Ile Val His Thr His
                85                  90                  95

Ser Gln Trp Ala Thr Ser Trp Ala Gln Ser Gly Arg Asp Ile Pro Pro
            100                 105                 110

Leu Gly Thr Thr His Ala Asp Tyr Phe Asp Ser Ala Ile Pro Cys Thr
        115                 120                 125

Arg Glu Met Tyr Asp Glu Ile Ile His Asp Tyr Glu Leu Asn Thr
    130                 135                 140

Gly Lys Val Ile Ala Glu Thr Phe Gln His His Asn Tyr Glu Gln Val
145                 150                 155                 160

Pro Gly Val Leu Val Asn Asn His Gly Pro Phe Cys Trp Gly Thr Asp
                165                 170                 175

Ala Leu Asn Ala Ile His Asn Ala Val Val Leu Glu Thr Val Ala Glu
            180                 185                 190

Met Ala Tyr His Ser Ile Met Leu Asn Lys Asp Val Thr Pro Ile Asn
        195                 200                 205

Thr Val Leu His Glu Lys His Phe Tyr Arg Lys His Gly Ala Asn Ala
    210                 215                 220

Tyr Tyr Gly Gln Ser
225

(2) INFORMATION FOR SEQ ID NO:15:

(i) SEQUENCE CHARACTERISTICS:
          (A) LENGTH: 690 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: Bacillus subtilis (ix) FEATURE:
          (A) NAME/KEY: mat_peptide
          (B) LOCATION: 1..690

-continued (xi) SEQUENCE DESCRIPTION: SEQ ID NO:15:

```
ATGCTTGAAA CATTAAAAAA AGAAGTGCTG GCTGCCAACC TGAAGCTTCA AGAGCATCAG      60
CTGGTAACCT TTACGTGGGG AAATGTCAGC GGCATTGACC GTGAAAAAGA AAGAATTGTC     120
ATCAAACTAG CGGAGTCGAA TACCAGCGAC CTGACAGCCG ATGACTTGGT TGTTTTGAAC     180
CTTGATGGAG AGGTCGTCGA AGGCTCGCTT AAACCTTCTT CAGATACACC TACCCATGTT     240
TATCTATATA AAGCCTTTCC GAATATCGGG GGAATTGTCC ATACCCATTC TCAATGGGCG     300
ACAAGCTGGG CGCAATCGGG CAGAGACATC CCTCCGTTAG GCACGACCCA TGCTGATTAT     360
TTTGACAGTG CGATTCCATG TACTCGAGAA ATGTACGATG AAGAAATCAT TCATGACTAC     420
GAACTGAATA CAGGAAAAGT CATAGCGGAA ACCTTTCAGC ATCATAATTA CGAACAGGTG     480
CCGGGTGTGC TCGTGAATAA TCACGGACCG TTCTGCTGGG GCACTGACGC CTTAAATGCC     540
ATTCATAACG CAGTTGTATT AGAAACGGTT GCCGAAATGG CCTATCACTC CATTATGCTG     600
AACAAGGATG TAACCCCAAT CAATACAGTC CTGCATGAAA AGCATTTTTA TCGAAAACAC     660
GGAGCAAATG CGTATTATGG CCAGTCATGA                                      690
```

(2) INFORMATION FOR SEQ ID NO:16:

(i) SEQUENCE CHARACTERISTICS:
        (A) LENGTH: 500 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Escherichia coli (xi) SEQUENCE DESCRIPTION: SEQ ID NO:16:

```
Met Thr Ile Phe Asp Asn Tyr Glu Val Trp Phe Val Ile Gly Ser Gln
1               5                   10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
        35                  40                  45

Val Leu Lys Pro Leu Gly Thr Thr Pro Asp Glu Ile Thr Ala Ile Cys
    50                  55                  60

Arg Asp Ala Asn Tyr Asp Asp Arg Cys Ala Gly Leu Val Val Trp Leu
65                  70                  75                  80

His Thr Phe Ser Pro Ala Lys Met Trp Ile Asn Gly Leu Thr Met Leu
                85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
        115                 120                 125

Gly Gly Arg Glu Phe Gly Phe Ile Gly Ala Arg Met Arg Gln Gln His
    130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
                165                 170                 175

Lys Val Cys Arg Phe Gly Asp Asn Met Arg Glu Val Ala Val Thr Asp
            180                 185                 190
```

```
Gly Asp Lys Val Ala Ala Gln Ile Lys Phe Gly Phe Ser Val Asn Thr
            195                 200                 205

Trp Ala Val Gly Asp Leu Val Gln Val Val Asn Ser Ile Ser Asp Gly
210                 215                 220

Asp Val Asn Ala Leu Val Asp Glu Tyr Glu Ser Cys Tyr Thr Met Thr
225                 230                 235                 240

Pro Ala Thr Gln Ile His Gly Glu Lys Arg Gln Asn Val Leu Glu Ala
            245                 250                 255

Ala Arg Ile Glu Leu Gly Met Lys Arg Phe Leu Glu Gln Gly Gly Phe
            260                 265                 270

His Ala Phe Thr Thr Thr Phe Glu Asp Leu His Gly Leu Lys Gln Leu
            275                 280                 285

Pro Gly Leu Ala Val Gln Arg Leu Met Gln Gln Gly Tyr Gly Phe Ala
            290                 295                 300

Gly Glu Gly Asp Trp Lys Thr Ala Ala Leu Leu Arg Ile Met Lys Val
305                 310                 315                 320

Met Ser Thr Gly Leu Gln Gly Gly Thr Ser Phe Met Glu Asp Tyr Thr
            325                 330                 335

Tyr His Phe Glu Lys Gly Asn Asp Leu Val Leu Gly Ser His Met Leu
            340                 345                 350

Glu Val Cys Pro Ser Ile Ala Val Glu Glu Lys Pro Ile Leu Asp Val
            355                 360                 365

Gln His Leu Gly Ile Gly Gly Lys Asp Asp Pro Ala Arg Leu Ile Phe
            370                 375                 380

Asn Thr Gln Thr Gly Pro Ala Ile Val Ala Ser Leu Ile Asp Leu Gly
385                 390                 395                 400

Asp Arg Tyr Arg Leu Leu Val Asn Cys Ile Asp Thr Val Lys Thr Pro
            405                 410                 415

His Ser Leu Pro Lys Leu Pro Val Ala Asn Ala Leu Trp Lys Ala Gln
            420                 425                 430

Pro Asp Leu Pro Thr Ala Ser Glu Ala Trp Ile Leu Ala Gly Gly Ala
            435                 440                 445

His His Thr Val Phe Ser His Ala Leu Asn Leu Asn Asp Met Arg Gln
            450                 455                 460

Phe Ala Glu Met His Asp Ile Glu Ile Thr Val Ile Asp Asn Asp Thr
465                 470                 475                 480

Arg Leu Pro Ala Phe Lys Asp Ala Leu Arg Trp Asn Glu Val Tyr Tyr
            485                 490                 495

Gly Phe Arg Arg
            500

(2) INFORMATION FOR SEQ ID NO:17:

(i) SEQUENCE CHARACTERISTICS:
        (A) LENGTH: 500 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Salmonella typhimurium (xi) SEQUENCE DESCRIPTION: SEQ ID NO:17:
```

-continued

```
Met Thr Ile Phe Asp Asn Tyr Glu Val Trp Phe Val Ile Gly Ser Gln
1               5                   10                  15

His Leu Tyr Gly Ala Glu Thr Leu Arg Gln Val Thr Gln His Ala Glu
            20                  25                  30

His Val Val Asn Ala Leu Asn Thr Glu Ala Lys Leu Pro Cys Lys Leu
            35                  40                  45

Val Leu Lys Pro Leu Gly Thr Ser Pro Asp Glu Ile Thr Ala Ile Cys
50                  55                  60

Arg Asp Ala Asn Tyr Asp Asp Arg Cys Ala Gly Leu Val Val Trp Leu
65                  70                  75                  80

His Thr Phe Ser Pro Ala Lys Met Trp Ile Asn Gly Leu Ser Ile Leu
                85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
            115                 120                 125

Gly Gly Arg Glu Phe Gly Phe Ile Gly Ala Arg Met Arg Gln Gln His
130                 135                 140

Ala Val Val Thr Gly His Trp Gln Asp Lys Glu Ala His Thr Arg Ile
145                 150                 155                 160

Gly Ala Trp Met Arg Gln Ala Val Ser Lys Gln Asp Thr Arg Gln Leu
                165                 170                 175

Lys Val Cys Arg Phe Gly Asp Asn Met Arg Glu Val Ala Val Thr Asp
            180                 185                 190

Gly Asp Lys Val Ala Ala Gln Ile Lys Phe Gly Phe Ser Val Asn Thr
            195                 200                 205

Trp Ala Val Gly Asp Leu Val Gln Val Val Asn Ser Ile Gly Asp Gly
    210                 215                 220

Asp Ile Asn Ala Leu Ile Asp Glu Tyr Glu Ser Ser Tyr Thr Leu Thr
225                 230                 235                 240

Pro Ala Thr Gln Ile His Gly Asp Lys Arg Gln Asn Val Arg Glu Ala
                245                 250                 255

Ala Gly Ile Glu Leu Gly Met Lys Arg Phe Leu Glu Gln Gly Gly Phe
            260                 265                 270

His Ala Phe Thr Thr Thr Phe Glu Asp Leu His Gly Leu Lys Gln Leu
            275                 280                 285

Pro Gly Leu Ala Val Gln Arg Leu Met Gln Gln Gly Tyr Gly Phe Ala
            290                 295                 300

Gly Glu Gly Asp Trp Lys Thr Ala Ala Leu Leu Arg Ile Met Lys Val
305                 310                 315                 320

Met Ser Thr Gly Leu Gln Gly Gly Thr Ser Phe Met Glu Asp Tyr Thr
                325                 330                 335

Tyr His Phe Glu Lys Gly Asn Asp Leu Val Leu Gly Ser His Met Leu
            340                 345                 350

Glu Val Cys Pro Ser Ile Ala Val Glu Glu Lys Pro Ile Leu Asp Val
            355                 360                 365

Gln His Leu Gly Ile Gly Gly Lys Glu Asp Pro Ala Arg Leu Ile Phe
            370                 375                 380

Asn Thr Gln Thr Gly Pro Ala Ile Val Ala Ser Leu Ile Asp Leu Gly
385                 390                 395                 400

Asp Arg Tyr Arg Leu Leu Val Asn Cys Ile Asp Thr Val Lys Thr Pro
            405                 410                 415

His Ser Leu Pro Lys Leu Pro Val Arg Asn Ala Leu Trp Lys Ala Gln
```

```
                    420                 425                 430
Pro Asp Leu Pro Thr Ala Ser Glu Ala Trp Ile Leu Ala Gly Gly Ala
            435                 440                 445

His His Thr Val Phe Ser His Ala Leu Asp Leu Asn Asp Met Arg Gln
450                 455                 460

Phe Ala Glu Ile His Asp Ile Glu Ile Ala Val Ile Asp Asn Asp Thr
465                 470                 475                 480

His Leu Pro Ala Phe Lys Asp Ala Leu Arg Trp Asn Glu Val Tyr Tyr
            485                 490                 495

Gly Phe Lys Arg
            500
```

(2) INFORMATION FOR SEQ ID NO:18:

(i) SEQUENCE CHARACTERISTICS:
        (A) LENGTH: 566 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Escherichia coli (xi) SEQUENCE DESCRIPTION: SEQ ID NO:18:

```
Met Ala Ile Ala Ile Gly Leu Asp Phe Gly Ser Asp Ser Val Arg Ala
1               5                   10                  15

Leu Ala Val Asp Cys Ala Ser Gly Glu Glu Ile Ala Thr Ser Val Glu
            20                  25                  30

Trp Tyr Pro Arg Trp Gln Lys Gly Gln Phe Cys Asp Ala Pro Asn Asn
        35                  40                  45

Gln Phe Arg His His Pro Arg Asp Tyr Ile Glu Ser Met Glu Ala Ala
50                  55                  60

Leu Lys Thr Val Leu Ala Glu Leu Ser Val Glu Gln Arg Ala Ala Val
65                  70                  75                  80

Val Gly Ile Gly Val Asp Ser Thr Gly Ser Thr Pro Ala Pro Ile Asp
            85                  90                  95

Ala Asp Gly Asn Val Leu Ala Leu Arg Pro Glu Phe Ala Glu Asn Pro
                100                 105                 110

Asn Ala Met Phe Val Leu Trp Lys Asp His Thr Ala Val Glu Arg Ser
            115                 120                 125

Glu Glu Ile Thr Arg Leu Cys His Ala Pro Gly Asn Val Asp Tyr Ser
130                 135                 140

Arg Tyr Ile Gly Gly Ile Tyr Ser Ser Glu Trp Phe Trp Ala Lys Ile
145                 150                 155                 160

Leu His Val Thr Arg Gln Asp Ser Ala Val Ala Gln Ser Ala Ala Ser
            165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Ser
            195                 200                 205

Leu Trp His Glu Ser Trp Gly Gly Leu Pro Pro Ala Ser Phe Phe Asp
            210                 215                 220

Glu Leu Asp Pro Ile Leu Asn Arg His Leu Pro Ser Pro Leu Phe Thr
225                 230                 235                 240
```

```
Asp Thr Trp Thr Ala Asp Ile Pro Val Gly Thr Leu Cys Pro Glu Trp
                245                 250                 255
Ala Gln Arg Leu Gly Leu Pro Glu Ser Val Val Ile Ser Gly Gly Ala
            260                 265                 270
Phe Asp Cys His Met Gly Ala Val Gly Ala Gly Ala Gln Pro Asn Ala
        275                 280                 285
Leu Val Lys Val Ile Gly Thr Ser Thr Cys Asp Ile Leu Ile Ala Asp
    290                 295                 300
Lys Gln Ser Val Gly Glu Arg Ala Val Lys Gly Ile Cys Gly Gln Val
305                 310                 315                 320
Asp Gly Ser Val Val Pro Gly Phe Ile Gly Leu Glu Ala Gly Gln Ser
                325                 330                 335
Ala Phe Gly Asp Ile Tyr Ala Trp Phe Gly Arg Val Leu Ser Trp Pro
            340                 345                 350
Leu Glu Gln Leu Ala Ala Gln His Pro Glu Leu Lys Ala Gln Ile Asn
        355                 360                 365
Ala Ser Gln Lys Gln Leu Leu Pro Ala Leu Thr Glu Ala Trp Ala Lys
    370                 375                 380
Asn Pro Ser Leu Asp His Leu Pro Val Val Leu Asp Trp Phe Asn Gly
385                 390                 395                 400
Arg Arg Ser Pro Asn Ala Asn Gln Arg Leu Lys Gly Val Ile Thr Asp
                405                 410                 415
Leu Asn Leu Ala Thr Asp Ala Pro Leu Leu Phe Gly Gly Leu Ile Ala
            420                 425                 430
Ala Thr Ala Phe Gly Ala Arg Ala Ile Met Glu Cys Phe Thr Asp Gln
        435                 440                 445
Gly Ile Ala Val Asn Asn Val Met Ala Leu Gly Gly Ile Ala Arg Lys
    450                 455                 460
Asn Gln Val Ile Met Gln Ala Cys Cys Asp Val Leu Asn Arg Pro Leu
465                 470                 475                 480
Gln Ile Val Ala Ser Asp Gln Cys Cys Ala Leu Gly Ala Ala Ile Phe
                485                 490                 495
Ala Ala Val Ala Ala Lys Val His Ala Asp Ile Pro Ser Ala Gln Gln
            500                 505                 510
Lys Met Ala Ser Ala Val Glu Lys Thr Leu Gln Pro Arg Ser Glu Gln
        515                 520                 525
Ala Gln Arg Phe Glu Gln Leu Tyr Arg Arg Tyr Gln Gln Trp Ala Met
    530                 535                 540
Ser Ala Glu Gln His Tyr Leu Pro Thr Ser Ala Pro Ala Gln Ala Ala
545                 550                 555                 560
Gln Ala Val Ala Thr Leu
                565

(2) INFORMATION FOR SEQ ID NO:19:

(i) SEQUENCE CHARACTERISTICS:
        (A) LENGTH: 569 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Salmonella typhimurium
```

(xi) SEQUENCE DESCRIPTION: SEQ ID NO:19:

Met Ala Ile Ala Ile Gly Leu Asp Phe Gly Ser Asp Ser Val Arg Ala
1               5                   10                  15

Leu Ala Val Asp Cys Ala Thr Gly Asp Glu Ile Ala Thr Ser Val Glu
            20                  25                  30

Trp Tyr Pro Arg Trp Gln Glu Gly Arg Tyr Cys Asp Gly Pro Asn Asn
        35                  40                  45

Gln Phe Arg His His Pro Arg Asp Tyr Met Glu Ser Met Glu Ala Ala
    50                  55                  60

Leu Lys Ala Val Leu Ala Gln Leu Ser Ala Ala Gln Arg Ala Asn Val
65                  70                  75                  80

Val Gly Ile Gly Val Asp Ser Thr Gly Ser Thr Pro Ala Pro Ile Asp
            85                  90                  95

Ala Asp Gly Asn Val Leu Ala Leu Arg Pro Glu Phe Ala Glu Asn Pro
            100                 105                 110

Asn Ala Met Phe Val Leu Trp Lys Asp His Thr Ala Val Glu Glu Ala
            115                 120                 125

Asp Glu Ile Thr Arg Leu Cys His Lys Pro Gly Lys Val Asp Tyr Ser
    130                 135                 140

Arg Tyr Ile Gly Gly Ile Tyr Ser Ser Glu Trp Phe Trp Ala Lys Ile
145                 150                 155                 160

Leu His Val Thr Arg Gln Asp Ser Ala Val Ala Gln Ala Ala Val Ser
            165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Thr
        195                 200                 205

Leu Trp His Glu Ser Trp Gly Gly Leu Pro Pro Ala Ser Phe Phe Asp
        210                 215                 220

Glu Leu Asp Pro Cys Ile Asn Arg His Leu Arg Tyr Pro Leu Phe Ser
225                 230                 235                 240

Glu Thr Phe Thr Ala Asp Leu Pro Val Gly Thr Leu Cys Ala Glu Trp
            245                 250                 255

Ala Gln Arg Leu Asp Leu Pro Glu Ser Val Val Ile Ser Gly Gly Ala
            260                 265                 270

Phe Asp Cys His Met Gly Ala Val Gly Ala Gly Ala Gln Pro Asn Thr
        275                 280                 285

Leu Val Lys Val Ile Gly Thr Ser Thr Cys Asp Ile Leu Ile Ala Asp
        290                 295                 300

Lys Gln Ser Val Gly Asp Arg Ala Val Lys Gly Ile Cys Gly Gln Val
305                 310                 315                 320

Asp Gly Ser Val Val Pro Asn Phe Ile Gly Leu Glu Ala Gly Gln Ser
            325                 330                 335

Ala Phe Gly Asp Ile Tyr Ala Trp Phe Ser Arg Val Leu Ser Trp Pro
        340                 345                 350

Leu Glu Gln Leu Ala Ala Gln His Pro Glu Leu Lys Pro Gln Ile Asn
        355                 360                 365

Ala Ser Gln Lys Gln Leu Leu Pro Ala Leu Thr Asp Ala Trp Ala Lys
        370                 375                 380

Asn Pro Ser Leu Asp His Leu Pro Val Val Leu Asp Trp Phe Asn Gly
385                 390                 395                 400

Arg Arg Thr Pro Asn Ala Asn Gln Arg Leu Lys Gly Val Ile Thr Asp

-continued

```
                    405                 410                 415
Leu Asn Leu Ala Thr Asp Ala Pro Ala Leu Phe Gly Gly Leu Val Ala
                420                 425                 430

Ser Thr Ala Phe Gly Ala Arg Ala Ile Gln Glu Cys Phe Thr Asp Gln
            435                 440                 445

Gly Ile Ala Val Asn Asn Val Met Ala Leu Gly Gly Ile Ala Arg Lys
        450                 455                 460

Asn Gln Val Ile Met Gln Val Cys Cys Asp Val Leu Asn Arg Pro Leu
465                 470                 475                 480

Gln Ile Val Ala Ser Asp Gln Cys Cys Ala Leu Gly Ala Ala Ile Phe
                485                 490                 495

Ala Ala Val Ala Ala Lys Val His Ala Asp Ile Pro Ala Ala Gln Gln
            500                 505                 510

Ser Met Ala Ser Ala Val Glu Arg Thr Leu Arg Pro His Pro Glu Gln
        515                 520                 525

Ala Gln Arg Phe Glu Gln Leu Tyr Arg Arg Tyr Gln Gln Trp Ala Leu
    530                 535                 540

Ser Ala Glu Gln His Tyr Leu Pro Thr Ala Ala Pro Ala Pro Thr Thr
545                 550                 555                 560

Pro Ala Asn Gln Ala Ile Leu Thr His
                565
```

(2) INFORMATION FOR SEQ ID NO:20:

(i) SEQUENCE CHARACTERISTICS:
        (A) LENGTH: 231 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Escherichia coli (xi) SEQUENCE DESCRIPTION: SEQ ID NO:20:

```
Met Leu Glu Asp Leu Lys Arg Gln Val Leu Glu Ala Asn Leu Ala Leu
1               5                   10                  15

Pro Lys His Asn Leu Val Thr Leu Thr Trp Gly Asn Val Ser Ala Val
                20                  25                  30

Asp Arg Glu Arg Gly Val Phe Val Ile Lys Pro Ser Gly Val Asp Tyr
            35                  40                  45

Ser Ile Met Thr Ala Asp Met Val Val Ser Ile Glu Thr Gly
        50                  55                  60

Glu Val Val Glu Gly Ala Lys Lys Pro Ser Ser Asp Thr Pro Thr His
65                  70                  75                  80

Arg Leu Leu Tyr Gln Ala Phe Pro Ser Ile Gly Ile Val His Thr
                85                  90                  95

His Ser Arg His Ala Thr Ile Trp Ala Gln Ala Gly Gln Ser Ile Pro
            100                 105                 110

Ala Thr Gly Thr Thr His Ala Asp Tyr Phe Tyr Gly Thr Ile Pro Cys
        115                 120                 125

Thr Arg Lys Met Thr Asp Ala Glu Ile Asn Gly Glu Tyr Glu Trp Glu
    130                 135                 140

Thr Gly Asn Val Ile Val Glu Thr Phe Glu Lys Gln Gly Ile Asp Ala
145                 150                 155                 160
```

Ala Gln Met Pro Gly Val Leu Val His Ser His Gly Pro Phe Ala Trp
            165                 170                 175

Gly Lys Asn Ala Glu Asp Ala Val His Asn Ala Ile Val Leu Glu Glu
            180                 185                 190

Val Ala Tyr Met Gly Ile Phe Cys Arg Gln Leu Ala Pro Gln Leu Pro
            195                 200                 205

Asp Met Gln Gln Thr Leu Leu Asn Lys His Tyr Leu Arg Lys His Gly
210                 215                 220

Ala Lys Ala Tyr Tyr Gly Gln
225                 230

(2) INFORMATION FOR SEQ ID NO:21:

(i) SEQUENCE CHARACTERISTICS:
        (A) LENGTH: 240 amino acids
        (B) TYPE: amino acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: Salmonella typhimurium (xi) SEQUENCE DESCRIPTION: SEQ ID NO:21:

Met Leu Glu Asp Leu Lys Arg Gln Val Leu Glu Ala Asn Leu Ala Leu
1               5                   10                  15

Pro Lys His Asn Leu Val Thr Leu Thr Trp Gly Asn Val Ser Ala Val
            20                  25                  30

Asp Arg Glu Arg Gly Val Leu Val Ile Lys Pro Ser Gly Val Asp Tyr
            35                  40                  45

Ser Val Met Thr Ala Asp Asp Met Val Val Ser Leu Glu Ser Gly
            50                  55                  60

Glu Val Val Glu Gly His Lys Lys Pro Ser Ser Asp Thr Pro Thr His
65                  70                  75                  80

Arg Leu Leu Tyr Gln Ala Phe Pro Thr Ile Gly Gly Ile Val His Thr
            85                  90                  95

His Ser Arg His Ala Thr Ile Trp Ala Gln Ala Gly Gln Pro Ile Pro
            100                 105                 110

Ala Thr Gly Thr Thr His Ala Asp Tyr Phe Tyr Gly Thr Ile Pro Cys
            115                 120                 125

Thr Arg Lys Met Thr Glu Ala Glu Ile Asn Gly Glu Tyr Glu Trp Glu
130                 135                 140

Thr Gly Asn Val Ile Val Glu Thr Phe Glu Lys Gln Gly Ile Asp Ala
145                 150                 155                 160

Ala Gln Met Pro Gly Val Leu Val His Ser His Gly Pro Phe Ala Trp
            165                 170                 175

Gly Lys Asn Ala Glu Asp Ala Val His Asn Ala Ile Val Leu Glu Glu
            180                 185                 190

Val Ala Tyr Met Gly Ile Phe Cys Arg His Leu Arg Arg Ser Cys Pro
            195                 200                 205

Thr Cys Ser Asn Pro Cys Trp Ile Asn Thr Ile Tyr Ala Asn Thr Ala
            210                 215                 220

Gln Lys Pro Ile Thr Gly Ser Asn Ala Lys Asn Ala Ser His Gly
225                 230                 235                 240

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (D) OTHER INFORMATION: "araA" <---> "araB"

(xi) SEQUENCE DESCRIPTION: SEQ ID NO:22:

AAAGTAGAGG GGGATGTCAC ATGGCTT                                    27

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (D) OTHER INFORMATION: "araB" <---> "araD"

(xi) SEQUENCE DESCRIPTION: SEQ ID NO:23:

AATTGATAAA GGGTGATGGA GCATGCTT                                  28

(2) INFORMATION FOR SEQ ID NO:24:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..23

(xi) SEQUENCE DESCRIPTION: SEQ ID NO:24:

TTGACATATA AT                                                          12

(2) INFORMATION FOR SEQ ID NO:25:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..23

(xi) SEQUENCE DESCRIPTION: SEQ ID NO:25:

GAAGCATGTA AACTGCCCC                                                    19

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: misc_feature
        (B) LOCATION: 1..23

(xi) SEQUENCE DESCRIPTION: SEQ ID NO:26:

CCAGCGTCTC TTCCCCG                                                      17

(2) INFORMATION FOR SEQ ID NO:27:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (D) OTHER INFORMATION:   "araL" <---> "araD"

(xi) SEQUENCE DESCRIPTION: SEQ ID NO:27:

AAAACACGGA GCAAATGCGT ATTATGGCCA AGTCATGATA                              40

(2) INFORMATION FOR SEQ ID NO:28:

(i) SEQUENCE CHARACTERISTICS:
        (A) LENGTH: 12 base pairs
```

(B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: rRNA
        (B) LOCATION: 1..15

(xi) SEQUENCE DESCRIPTION: SEQ ID NO:28:

UCUUUCCCCA CU                                                                12

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (D) OTHER INFORMATION: "araA"

(xi) SEQUENCE DESCRIPTION: SEQ ID NO:29:

TTTATGAGAA AGGGGCAGTT TACATGCT                                               28

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:30:

GGCTGAGGAG GGGATTCTGA TATGAATCG                                              29

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:31:

AATAGCCCGC ACCTCGAATG GAAGGGGTAA CGCGATG                                     37

(2) INFORMATION FOR SEQ ID NO:32:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: rRNA
        (B) LOCATION: 1..15

(xi) SEQUENCE DESCRIPTION: SEQ ID NO:32:

UCUUUCCCCC U                                            11

(2) INFORMATION FOR SEQ ID NO:33:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:33:

ATAGAATCCC ATTCAAAAGT GAAAGAGGGG AGGTTCTCAT G            41

(2) INFORMATION FOR SEQ ID NO:34:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (vi) ORIGINAL SOURCE:
        (A) ORGANISM: Bacillus subtilis (ix) FEATURE:
        (A) NAME/KEY: rRNA
        (B) LOCATION: 1..15

(xi) SEQUENCE DESCRIPTION: SEQ ID NO:34:

UCUUUCCUCC ACU                                          13

(2) INFORMATION FOR SEQ ID NO:35:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear

```
    (ii) MOLECULE TYPE: cDNA (iii) HYPOTHETICAL: NO (vi) ORIGINAL SOURCE:
         (A) ORGANISM: Bacillus subtilis (xi) SEQUENCE DESCRIPTION: SEQ ID NO:35:

ATGCTTCAGA CAAAGGATTA TGAATTCTGG TTTGTGACAG GAAGCCAGCA CCTATACGGG        60

GAAGAGACGC TGGAACTCGT AGATCAGCAT GCTAAAAGCA TTTGTGAGGG GCTCAGCGGG       120

ATTTCTTCCA GATATAAAAT CACTCATAAG CCCGTCGTCA CTTCACCGGA AACCATTAGA       180

GAGCTGTTAA GAGAAGCGGA GTACAGTGAG ACATGTGCTG GCATCATTAC ATGGATGCAC       240

ACATTTTCCC CTGCAAAAAT GTGGATAGAA GGCCTTTCCT CTTATCAAAA ACCGCTTATG       300

CATTTGCATA CCCAATATAA TCGCGATATC CCGTGGGGTA CGATTGACAT GGATTTTATG       360

AACAGCAACC AATCCGCGCA TGGCGATCGA GAGTACGGTT ACATCAACTC GAGAATGGGG       420

CTTAGCCGAA AAGTCATTGC CGGCTATTGG GATGATGAAG AAGTGAAAAA AGAAATGTCC       480

CAGTGGATGG ATACGGCGGC TGCATTAAAT GAAAGCAGAC ATATTAAGGT TGCCAGATTT       540

GGAGATAACA TGCGTCATGT CGCGGTAACG GACGGAGACA AGGTGGGAGC GCATATTCAA       600

TTTGGCTGGC AGGTTGACGG ATATGGCATC GGGGATCTCG TTGAAGTGAT GGATCGCATT       660

ACGGACGACG AGGTTGACAC GCTTTATGCC GAGTATGACA GACTATATGT GATCAGTGAG       720

GAAACAAAAC GTGACGAAGC AAAGGTAGCG TCCATTAAAG AACAGGCGAA AATTGAACTT       780

GGATTAACCG CTTTTCTTGA GCAAGGCGGA TACACAGCGT TTACGACATC GTTTGAAGTG       840

CTGCACGGAA TGAAACAGCT GCCGGGACTT GCCGTTCAGC GCCTGATGGA GAAAGGCTAT       900

GGGTTTGCCG GTGAAGGAGA TTGGAAGACA GCGGCCCTTG TACGGATGAT GAAAATCATG       960

GCTAAAGGAA AAAGAACTTC CTTCATGGAA GATTACACGT ACCATTTTGA ACCGGGAAAT      1020

GAAATGATTC TGGGCTCTCA CATGCTTGAA GTGTGTCCGA CTGTCGCTTT GGATCAGCCG      1080

AAAATCGAGG TTCATTCGCT TTCGATTGGC GGCAAAGAGG ACCCTGCGCG TTTGGTATTT      1140

AACGGCATCA GCGGTTCTGC CATTCAAGCT AGCATTGTTG ATATTGGCGG GCGTTTCCGC      1200

CTTGTGCTGA ATGAAGTCAA CGGCCAGGAA ATTGAAAAAG ACATGCCGAA TTTACCGGTT      1260

GCCCGTGTTC TCTGGAAGCC GGAGCCGTCA TTGAAAACAG CAGCGGAGGC ATGGATTTTA      1320

GCCGGCGGTG CACACCATAC CTGCCTGTCT TATGAACTGA CAGCGGAGCA AATGCTTGAT      1380

TGGGCGGAAA TGGCGGGAAT CGAAAGTGTT CTCATTTCCC GTGATACGAC AATTCATAAA      1440

CTGAAACACG AGTTAAAATG GAACGAGGCG CTTTACCGGC TTCAAAAGTA G              1491

(2) INFORMATION FOR SEQ ID NO:36:

(i) SEQUENCE CHARACTERISTICS:
        (A) LENGTH: 1683 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
         (A) ORGANISM: Bacillus subtilis (xi) SEQUENCE DESCRIPTION: SEQ ID NO:36:

ATGGCTTACA CAATAGGGGT TGATTTTGGA ACTTTATCAG GAAGAGCAGT GCTCGTTCAT        60
```

-continued

```
GTCCAAACAG GGGAGGAACT TGCGGCTGCT GTAAAAGAAT ACAGGCATGC TGTCATTGAT      120

ACCGTCCTTC CAAAAACGGG TCAAAAGCTG CCGCGTGACT GGGCGCTGCA GCACCCTGCT      180

GATTACCTCG AAGTCTTGGA AACAACCATT CCGTCTTTAC TCGAACAGAC GGGCGTTGAC      240

CCGAAAGACA TTATCGGGAT TGGAATTGAT TTCACGGCAT GTACGATCCT TCCTATTGAC      300

AGCAGCGGGC AGCCGTTATG CATGCTGCCT GAATATGAAG AGGAGCCGCA CAGCTATGTG      360

AAGCTCTGGA AGCATCATGC GGCCCAAAAA CATGCTGATC GGCTCAATCA AATCGCGGAA      420

GAAGAAGGAG AGGCTTTTTT ACAGCGGTAC GGAGGAAAAA TTTCATCAGA ATGGATGATT      480

CCAAAGGTCA TGCAAATTGC CGAGGAAGCG CCTCACATTT ATGAAGCGGC TGACCGGATC      540

ATCGAGGCTG CGGACTGGAT CGTGTACCAG CTGTGCGGCT CGCTCAAGCG AAGCAATTGT      600

ACCGCAGGGT ATAAAGCGAT GTGGAGTGAA AAAGCGGGGT ATCCGTCAGA TGATTTCTTT      660

GAGAAATTAA ATCCTTCAAT GAAAACGATT ACAAAGGACA AATTGTCAGG TTCTATTCAT      720

TCAGTAGGAG AAAAAGCCGG CAGTCTGACT GAAAAAATGG CAAAGCTGAC AGGGCTTCTC      780

CCGGGAACGG CTGTTGCGGT TGCCAATGTG GACGCTCATG TTTCGGTACC GGCGGTCGGC      840

ATTACAGAGC CAGGGAAAAT GCTGATGATT ATGGGAACCT CGACGTGCCA TGTTCTACTT      900

GGTGAAGAGG TGCATATCGT TCCAGGAATG TGCGGCGTTG TGGACAACGG AATTCTCCCG      960

GGCTATGCGG GATATGAAGC CGGGCAGTCC TGTGTCGGCG ATCATTTTGA CTGGTTTGTG     1020

AAAACATGTG TCCCGCCAGC TTATCAAGAG GAAGCAAAGG AAAAAAACAT TGGCGTTCAT     1080

GAGCTGCTGA GTGAGAAAGC AAACCATCAA GCGCCTGGTG AAAGCGGCTT GCTTGCTTTA     1140

GATTGGTGGA ATGGAAACCG TTCAACTCTT GTTGATGCAG ATTTAACAGG GATGCTGCTT     1200

GGCATGACAC TGCTGACGAA GCCTGAAGAG ATTTATAGAG CGTTAGTTGA AGCGACAGCT     1260

TACGGAACCC GGATGATTAT CGAAACATTC AAAGAAAGCG GTGTTCCGAT TGAGGAACTG     1320

TTCGCAGCCG GCGGAATAGC TGAGAAAAAC CCGTTTGTCA TGCAGATTTA TGCGGATGTG     1380

ACAAACATGG ACATTAAAAT CTCTGGTTCA CCGCAAGCCC CAGCCTTAGG ATCTGCCATT     1440

TTCGGCGCGC TTGCAGCAGG CAAAGAAAAA GGCGGCTACG ATGATATCAA AAAGGCAGCG     1500

GCGAACATGG GAAAACTGAA AGATATAACT TATACGCCAA ATGCCGAAAA CGCCGCGGTT     1560

TATGAAAAAT TGTACGCTGA ATATAAAGAG CTGGTTCATT ATTTCGGAAA AGAAAACCAT     1620

GTCATGAAGC GTCTGAAAAC GATCAAAAAT CTTCAATTTT CATCTGCCGC CAAAAAGAAT     1680

TGA                                                                  1683
```

(2) INFORMATION FOR SEQ ID NO:37:

(i) SEQUENCE CHARACTERISTICS:
        (A) LENGTH: 690 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Bacillus subtilis (xi) SEQUENCE DESCRIPTION: SEQ ID NO:37:

```
ATGCTTGAAA CATTAAAAAA AGAAGTGCTG GCTGCCAACC TGAAGCTTCA AGAGCATCAG       60

CTGGTAACCT TTACGTGGGG AAATGTCAGC GGCATTGACC GTGAAAAAGA AAGAATTGTC      120

ATCAAACTAG CGGAGTCGAA TACCAGCGAC CTGACAGCCG ATGACTTGGT TGTTTTGAAC      180
```

```
CTTGATGGAG AGGTCGTCGA AGGCTCGCTT AAACCTTCTT CAGATACACC TACCCATGTT    240

TATCTATATA AAGCCTTTCC GAATATCGGG GGAATTGTCC ATACCCATTC TCAATGGGCG    300

ACAAGCTGGG CGCAATCGGG CAGAGACATC CCTCCGTTAG GCACGACCCA TGCTGATTAT    360

TTTGACAGTG CGATTCCATG TACTCGAGAA ATGTACGATG AAGAAATCAT TCATGACTAC    420

GAACTGAATA CAGGAAAAGT CATAGCGGAA ACCTTTCAGC ATCATAATTA CGAACAGGTG    480

CCGGGTGTGC TCGTGAATAA TCACGGACCG TTCTGCTGGG GCACTGACGC CTTAAATGCC    540

ATTCATAACG CAGTTGTATT AGAAACGGTT GCCGAAATGG CCTATCACTC CATTATGCTG    600

AACAAGGATG TAACCCCAAT CAATACAGTC CTGCATGAAA AGCATTTTTA TCGAAAACAC    660

GGAGCAAATG CGTATTATGG CCAGTCATGA                                     690
```

(2) INFORMATION FOR SEQ ID NO:38:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (xi) SEQUENCE DESCRIPTION: SEQ ID NO:38:

```
TTGACANNNN NNNNNNNNNN NNNTATAAT                                       29
```

(2) INFORMATION FOR SEQ ID NO:39:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Bacillus subtilis (ix) FEATURE:
    (D) OTHER INFORMATION: "araQ" <---> "abfA"

(xi) SEQUENCE DESCRIPTION: SEQ ID NO:39:

```
GTTAATGAAG GAGGAAACGT GTGATGA                                         27
```

(2) INFORMATION FOR SEQ ID NO:40:

(i) SEQUENCE CHARACTERISTICS:
    (A) LENGTH: 85 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Bacillus subtilis (ix) FEATURE:
           (D) OTHER INFORMATION: "abfA"

(xi) SEQUENCE DESCRIPTION: SEQ ID NO:40:

TCAATAAGAA TAGCAAAGCC GGAGATTTCT CTCCGGCTTG TCTTTCAACT GCCACGAGCC    60

GGCCCATTCC AGCCGGCTTT TTGTA    85

(2) INFORMATION FOR SEQ ID NO:41:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (xi) SEQUENCE DESCRIPTION: SEQ ID NO:41:

UCUUUCCCCC U    11

(2) INFORMATION FOR SEQ ID NO:42:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (xi) SEQUENCE DESCRIPTION: SEQ ID NO:42:

UCUUUCCUCC ACU    13

(2) INFORMATION FOR SEQ ID NO:43:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (xi) SEQUENCE DESCRIPTION: SEQ ID NO:43:

UCUUUCCCCA CU    12

(2) INFORMATION FOR SEQ ID NO:44:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (iii) HYPOTHETICAL: NO (xi) SEQUENCE DESCRIPTION: SEQ ID NO:44:

Glu Ala Ala Xaa Xaa Xaa Gly Xaa Xaa Xaa Xaa Xaa Xaa Ile Xaa Leu
1               5                   10                  15
Pro (2) INFORMATION FOR SEQ ID NO:45:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:45:

```
Ile Ala Gly Cys Ser Ala
1               5
```

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:46:

```
CCTCTTCGCT ATTACGC                                              17
```

(2) INFORMATION FOR SEQ ID NO:47:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:47:

```
Leu Xaa Xaa Leu Gly Lys Xaa Phe Glu Xaa Asp Xaa Xaa Gly Ile Lys
1               5                  10                  15

Val Xaa Val
```

(2) INFORMATION FOR SEQ ID NO:48:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:48:

```
Tyr Val Glu Met Val Lys Glu Trp Asn Lys Lys Tyr Pro Asp Arg Lys
1               5                  10                  15

Ile Lys Leu Asn Thr Val Val Tyr Pro Tyr
                20                  25
```

(2) INFORMATION FOR SEQ ID NO:49:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:49:

Met Lys Lys Ala Arg Met Ile Val Asp Lys Glu Tyr Lys Ile Gly Glu
1               5                   10                  15

Val Asp Lys Arg Ile Tyr Gly Ser Phe Ile Glu His Met Gly Arg Ala
            20                  25                  30

Val Tyr Glu Gly Ile Tyr Glu Pro Asp His Pro Glu Ala Asp Glu Asp
        35                  40                  45

Gly (2) INFORMATION FOR SEQ ID NO:50:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:50:

Ala Thr Lys Lys Ala Thr Met Ile Ile Glu Lys Asp Phe Lys Ile Ala
1               5                   10                  15

Glu Ile Asp Lys Arg Ile Tyr Gly Ser Phe Ile Glu His Leu Gly Arg
            20                  25                  30

Ala Val Tyr Gly Gly Ile Tyr Glu Pro Gly His Pro Gln Ala Asp Glu
        35                  40                  45

Asn Gly
    50

(2) INFORMATION FOR SEQ ID NO:51:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:51:

Gly Leu Gln Asn Val Pro Lys Glu Leu Tyr Glu Ala Ala Asp Ile Asp
1               5                   10                  15

Gly Ala Asn Thr Met Lys Lys Phe Leu His Ile Thr Leu Pro Phe Leu
            20                  25                  30

Lys Pro Val Thr Val Tyr Val Leu
        35                  40

(2) INFORMATION FOR SEQ ID NO:52:

-continued

```
    (i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:52:

Ala Leu Gln Ser Ile Pro Asp Ser Leu Ile Glu Ala Ala Lys Ile Asp
1               5                  10                  15

Gly Ala Gly Pro Phe Gln Arg Phe Trp Asn Ile Val Leu Pro Leu Leu
            20                  25                  30

Lys Pro Val Leu Ala Val Leu Leu
            35                  40

(2) INFORMATION FOR SEQ ID NO:53:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:53:

Tyr Ala Leu Gly Leu Pro Arg Asp Leu Leu Asp Ser Ala Arg Met Asp
1               5                  10                  15

Gly Cys Thr Glu Arg Gly Ile Phe Phe Arg Ile Met Ala Pro Leu Met
            20                  25                  30

Lys Pro Ala Phe Gly Ala Met Ile
            35                  40

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Bacillus subtilis (xi) SEQUENCE DESCRIPTION: SEQ ID NO:54:

TATAATAAAA TTGTTCGTAC AAA                                       23

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
              (A) ORGANISM: Bacillus subtilis (ix) FEATURE:
              (D) OTHER INFORMATION: "araP" <---> "araQ"

(xi) SEQUENCE DESCRIPTION: SEQ ID NO:55:

TTAAGGGGGA GGGATAAATG                                                    20

(2) INFORMATION FOR SEQ ID NO:56:

(i) SEQUENCE CHARACTERISTICS:
              (A) LENGTH: 18 amino acids
              (B) TYPE: amino acid
              (D) TOPOLOGY: linear (ii) MOLECULE TYPE: protein (xi) SEQUENCE DESCRIPTION: SEQ ID NO:56:

Met Leu Gln Thr Lys Asp Tyr Glu Phe Trp Phe Val Thr Gly Ser Gln
 1               5                  10                  15

His Leu (2) INFORMATION FOR SEQ ID NO:57:

(i) SEQUENCE CHARACTERISTICS:
              (A) LENGTH: 94 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vi) ORIGINAL SOURCE:
              (A) ORGANISM: Bacillus subtilis (ix) FEATURE:
              (A) NAME/KEY: CDS
              (B) LOCATION: 1..94

(xi) SEQUENCE DESCRIPTION: SEQ ID NO:57:

ATG GCC AGT CAT GAT ACG CCT GTG TCA CCG GCT GGC ATT CTG ATT GAC          48
Met Ala Ser His Asp Thr Pro Val Ser Pro Ala Gly Ile Leu Ile Asp
 1               5                  10                  15

TTG GAC GGT ACT GTA TTC AGA GGA AAT GAG TTG ATC GAA GGA GCA A            94
Leu Asp Gly Thr Val Phe Arg Gly Asn Glu Leu Ile Glu Gly Ala
            20                  25                  30

(2) INFORMATION FOR SEQ ID NO:58:

(i) SEQUENCE CHARACTERISTICS:
              (A) LENGTH: 31 amino acids
              (B) TYPE: amino acid
              (D) TOPOLOGY: linear (ii) MOLECULE TYPE: protein (xi) SEQUENCE DESCRIPTION: SEQ ID NO:58:

Met Ala Ser His Asp Thr Pro Val Ser Pro Ala Gly Ile Leu Ile Asp
 1               5                  10                  15

Leu Asp Gly Thr Val Phe Arg Gly Asn Glu Leu Ile Glu Gly Ala
            20                  25                  30

(2) INFORMATION FOR SEQ ID NO:59:

(i) SEQUENCE CHARACTERISTICS:
        (A) LENGTH: 269 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "araL"

(xi) SEQUENCE DESCRIPTION: SEQ ID NO:59:

```
Met Ala Ser His Asp Thr Pro Val Ser Pro Ala Gly Ile Leu Ile Asp
 1               5                  10                  15

Leu Asp Gly Thr Val Phe Arg Gly Asn Glu Leu Ile Glu Gly Ala Arg
             20                  25                  30

Glu Ala Ile Lys Thr Leu Arg Arg Met Gly Lys Lys Ile Val Phe Leu
         35                  40                  45

Ser Asn Arg Gly Asn Ile Ser Arg Ala Met Cys Arg Lys Lys Leu Leu
     50                  55                  60

Gly Ala Gly Ile Glu Thr Asp Val Asn Asp Ile Val Leu Ser Ser Ser
 65                  70                  75                  80

Val Thr Ala Ala Phe Leu Lys Lys His Tyr Arg Phe Ser Lys Val Trp
                 85                  90                  95

Val Leu Gly Glu Gln Gly Leu Val Asp Glu Leu Arg Leu Ala Gly Val
            100                 105                 110

Gln Asn Ala Ser Glu Pro Lys Glu Ala Asp Trp Leu Val Ile Ser Leu
        115                 120                 125

His Glu Thr Leu Thr Tyr Asp Asp Leu Asn Gln Ala Phe Gln Ala Ala
    130                 135                 140

Ala Gly Gly Ala Arg Ile Ile Ala Thr Asn Lys Asp Arg Ser Phe Pro
145                 150                 155                 160

Asn Glu Asp Gly Asn Ala Ile Asp Val Ala Gly Met Ile Gly Ala Ile
                165                 170                 175

Glu Thr Ser Ala Gln Ala Lys Thr Glu Leu Val Val Gly Lys Pro Ser
            180                 185                 190

Trp Leu Met Ala Glu Ala Ala Cys Thr Ala Met Gly Leu Ser Ala His
        195                 200                 205

Glu Cys Met Ile Ile Gly Asp Ser Ile Glu Ser Asp Ile Ala Met Gly
    210                 215                 220

Lys Leu Tyr Gly Met Lys Ser Ala Leu Val Leu Thr Gly Ser Ala Lys
225                 230                 235                 240

Gln Gly Glu Gln Arg Leu Tyr Thr Pro Asp Tyr Val Leu Asp Ser Ile
                245                 250                 255

Lys Asp Val Thr Lys Leu Ala Glu Glu Gly Ile Leu Ile
            260                 265
```

(2) INFORMATION FOR SEQ ID NO:60:

(i) SEQUENCE CHARACTERISTICS:
        (A) LENGTH: 394 amino acids
        (B) TYPE: amino acid
        (D) TOPOLOGY: linear (ii) MOLECULE TYPE: protein (vi) ORIGINAL SOURCE:

(A) ORGANISM: Bacillus subtilis (ix) FEATURE:
    (D) OTHER INFORMATION: /product= "araM"

(xi) SEQUENCE DESCRIPTION: SEQ ID NO:60:

```
Met Asn Arg Ile Ala Ala Asp Val Gln Arg Ala Phe Glu Asn Ala Gly
 1               5                  10                  15

Glu Lys Thr Leu Pro Ile Lys Val Glu Glu Ile Val Leu Gly Lys Gln
                20                  25                  30

Ala Ala Asp Ser Leu Leu Asp Tyr Val Lys Arg Lys Asn Asn Gln His
            35                  40                  45

Ile Val Leu Val Cys Asp Ala Asn Thr His Arg Ile Ala Gly Ile Asp
50                  55                  60

Leu Glu Asn Arg Leu Asn Gln Glu Gly Phe Gln Ala Glu Cys Leu Ile
65                  70                  75                  80

Ile Pro Glu Asn Glu Ala Gly Asp Val Thr Ala Asp Glu Arg Ser Leu
                85                  90                  95

Ile His Val Leu Ile His Thr Lys Gln Pro Thr Asp Val Met Ile Ala
                100                 105                 110

Val Gly Ser Gly Thr Ile His Asp Ile Val Arg Phe Ala Ala Phe Gln
            115                 120                 125

Arg Asp Leu Pro Phe Ile Ser Tyr Pro Thr Ala Pro Ser Val Asp Gly
130                 135                 140

Phe Thr Ser Ala Gly Ala Pro Ile Ile Leu Tyr Gly Thr Lys Thr Thr
145                 150                 155                 160

Ile Gln Thr Lys Ala Pro Ser Ala Leu Phe Ala Asp Leu Asp Leu Leu
                165                 170                 175

Lys Ala Ala Pro Gln Ser Met Val Ala Ala Gly Phe Gly Asp Met Leu
            180                 185                 190

Gly Lys Ile Thr Ser Leu Ala Asp Trp Glu Ile Ser Arg His Leu Ala
            195                 200                 205

Gly Glu Pro Tyr Ser Pro Ala Gly Ala Lys Ile Val Gln Glu Ala Leu
        210                 215                 220

Ala Ala Cys Ile Glu His Thr Glu Asp Ile Ala Met Lys Thr Glu Thr
225                 230                 235                 240

Gly Ile Arg Val Leu Met Glu Ser Leu Leu Val Ser Gly Leu Val Met
                245                 250                 255

Leu Ala Leu Asp His Ser Arg Pro Ala Ser Gly Glu His His Ile
            260                 265                 270

Ser His Trp Ile Glu Met Glu Leu Met Glu Lys Lys Arg Pro Gln Ile
            275                 280                 285

Leu His Gly Ala Lys Val Gly Cys Ala Ala Val Leu Leu Thr Asp Thr
        290                 295                 300

Tyr Arg Lys Leu Ala Gln Asp Asp Gly Leu Asn Glu Phe Ser Pro Ser
305                 310                 315                 320

Arg Arg Glu Ala Ile Gln Ser Ala Tyr Gln Thr Leu Pro Arg Gly Glu
                325                 330                 335

Val Leu Ala Asp Trp Leu Arg Ser Ala Gly Pro Ala Asp Phe Asp
            340                 345                 350

Glu Ile Gly Val Gly Gln Asp Ser Val Lys Asn Ala Phe Arg His Ala
            355                 360                 365

His Thr Leu Arg Asp Arg Cys Thr Gly Leu Arg Ile Ile Asn Glu Asn
370                 375                 380
```

Lys Thr Leu Ile Asn His Gly Leu Tyr Glu
385                 390

(2) INFORMATION FOR SEQ ID NO:61:

(i) SEQUENCE CHARACTERISTICS:
        (A) LENGTH: 433 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "araN"

(xi) SEQUENCE DESCRIPTION: SEQ ID NO:61:

Met Lys Lys Met Thr Val Cys Phe Leu Val Leu Met Met Leu Leu Thr
1               5                   10                  15

Leu Val Ile Ala Gly Cys Ser Ala Glu Lys Ser Ser Gly Lys Ser Gly
            20                  25                  30

Glu Thr Glu Leu Thr Phe Trp Thr Phe Asn Gly Leu His Glu Gln Phe
        35                  40                  45

Tyr Val Glu Met Val Lys Glu Trp Asn Lys Lys Tyr Pro Asp Arg Lys
50                  55                  60

Ile Lys Leu Asn Thr Val Val Tyr Pro Tyr Gly Gln Met His Asp Asn
65                  70                  75                  80

Leu Ser Ile Ser Leu Ile Ala Gly Glu Gly Val Pro Asp Ile Ala Asp
                85                  90                  95

Val Glu Leu Ala Arg Phe Ser Asn Phe Leu Lys Gly Ser Asp Ile Pro
            100                 105                 110

Leu Ala Asp Leu Thr Pro Leu Ile Glu Lys Asp Arg Asp Lys Phe Val
            115                 120                 125

Glu Ala Arg Leu Thr Leu Tyr Ser Lys Asn Gly Lys Leu Tyr Gly Leu
        130                 135                 140

Asp Thr His Val Gly Thr Thr Val Met Phe Tyr Asn Met Asp Val Met
145                 150                 155                 160

Lys Lys Ala Gly Val Asn Pro Asp Asp Ile Lys Thr Trp Asp Asp Tyr
                165                 170                 175

His Lys Ala Gly Gln Lys Val Arg Lys Val Thr Gly Lys Pro Met Gly
            180                 185                 190

Thr Val Glu Thr Asn Asp Ser Ala Thr Phe Leu Ser Met Ile Ser Gln
        195                 200                 205

Gln Asn Ser Gly Tyr Phe Asp Lys Asn Gly Lys Leu Ile Leu Asn Asn
210                 215                 220

Asp Thr Asn Val Lys Thr Leu Gln Tyr Leu Lys Asp Met Ile Asn Asp
225                 230                 235                 240

Lys Thr Met Ile Pro Ala Pro Gly Gly His His Ser Glu Glu Tyr
                245                 250                 255

Tyr Gly Phe Met Asn Gln Gly Gly Ala Ala Ser Val Leu Met Pro Ile
            260                 265                 270

Trp Tyr Met Gly Arg Phe Ile Asp Tyr Met Pro Asp Leu Lys Gly Lys
        275                 280                 285

Ile Ala Ile Arg Pro Leu Pro Ala Trp Lys Glu Gly Gly Asp Arg Ser
290                 295                 300

Ala Gly Leu Gly Gly Thr Ala Thr Val Val Pro Lys Gln Ser Lys His

-continued

```
305                 310                 315                 320

Val Glu Leu Ala Lys Glu Phe Leu Ala Phe Ala Lys Gly Ser Glu Glu
                325                 330                 335

Gly Asn Lys Lys Leu Trp Ser Val Leu Gly Phe Asp Pro Leu Arg Trp
                340                 345                 350

Asp Val Trp Ser Ser Lys Glu Leu Lys Glu Lys Asn Lys Tyr Thr Asp
                355                 360                 365

Tyr Phe Gln Asn Gly Thr Gly Ile Phe Ser Val Leu Leu Asp Ile Lys
        370                 375                 380

Asp Glu Ile Asn Pro Ile Tyr Leu His Glu Asp Phe Ala Lys Ala Ser
385                 390                 395                 400

Asp Leu Val Asn Arg Ser Val Leu Phe Asp Ala Leu Lys Ser Gln Gln
                405                 410                 415

Lys Thr Pro Lys Gln Ala Leu Asp Arg Ala Ala Gly Glu Leu Lys Gln
                420                 425                 430

Lys
```

(2) INFORMATION FOR SEQ ID NO:62:

(i) SEQUENCE CHARACTERISTICS:
        (A) LENGTH: 313 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "araP"

(xi) SEQUENCE DESCRIPTION: SEQ ID NO:62:

```
Met Lys Pro Val Lys Thr Gly Thr Val His Pro Val Pro Ser Ala Ala
 1               5                  10                  15

Lys Gln Ser Gly Trp Arg Asp Leu Phe Tyr Ser Lys Lys Ala Ala Pro
                20                  25                  30

Tyr Leu Phe Thr Ala Pro Phe Val Leu Ser Phe Leu Val Phe Phe Leu
            35                  40                  45

Tyr Pro Ile Ile Ser Val Phe Ile Met Ser Phe Gln Arg Ile Leu Pro
        50                  55                  60

Gly Glu Val Ser Phe Val Gly Leu Ser Asn Tyr Thr Ala Leu Asn Asn
65                  70                  75                  80

Pro Thr Phe Tyr Thr Ala Leu Trp Asn Thr Leu Glu Tyr Thr Phe Trp
                85                  90                  95

Thr Leu Ile Val Leu Ile Pro Val Pro Leu Leu Leu Ala Ile Phe Leu
                100                 105                 110

Asn Ser Lys Leu Val Lys Phe Arg Asn Ile Phe Lys Ser Ala Leu Phe
            115                 120                 125

Ile Pro Ala Leu Thr Ser Thr Ile Val Ala Gly Ile Ile Phe Arg Leu
130                 135                 140

Ile Phe Gly Glu Met Glu Thr Ser Leu Ala Asn Ser Ile Leu Leu Lys
145                 150                 155                 160

Leu Gly Phe Ser Pro Gln Asn Trp Met Asn Asn Glu His Thr Gly Met
                165                 170                 175

Phe Leu Met Val Leu Leu Ala Ser Trp Lys Trp Met Gly Ile Asn Ile
                180                 185                 190
```

-continued

```
Leu Tyr Phe Leu Ala Gly Leu Gln Asn Val Pro Lys Glu Leu Tyr Glu
        195                 200                 205

Ala Ala Asp Ile Asp Gly Ala Asn Thr Met Lys Lys Phe Leu His Ile
210                 215                 220

Thr Leu Pro Phe Leu Lys Pro Val Thr Val Tyr Val Leu Thr Ile Ser
225                 230                 235                 240

Ile Ile Gly Gly Phe Arg Met Phe Glu Glu Ser Tyr Val Leu Trp Gln
                245                 250                 255

Asn Asn Ser Pro Gly Asn Ile Gly Leu Thr Leu Val Gly Tyr Leu Tyr
                260                 265                 270

Gln Gln Gly Leu Ala Tyr Asn Glu Met Gly Tyr Gly Ala Ala Ile Gly
                275                 280                 285

Ile Val Leu Leu Ile Val Ile Leu Val Val Ser Leu Ile Ser Leu Lys
        290                 295                 300

Leu Ser Gly Ser Phe Lys Gly Glu Gly
305                 310
```

(2) INFORMATION FOR SEQ ID NO:63:

(i) SEQUENCE CHARACTERISTICS:
        (A) LENGTH: 281 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "araQ"

(xi) SEQUENCE DESCRIPTION: SEQ ID NO:63:

```
Met Leu Arg His Ser Pro Gln Phe Ser Val Tyr Arg Ile Ala Leu Thr
  1                 5                  10                  15

Leu Phe Phe Met Met Leu Ser Leu Leu Tyr Leu Phe Pro Ile Phe Cys
                 20                  25                  30

Leu Leu Leu Gly Ser Leu Lys Pro Ser Ser Glu Leu Leu Arg Val Gly
         35                  40                  45

Leu Asn Leu Asp Ile Asp Pro Lys Val Met Ser Phe Asp Asn Tyr Thr
 50                  55                  60

Phe Leu Phe Asn Gly Gly Ser Ile Tyr Phe Lys Trp Phe Phe Asn Ser
 65                  70                  75                  80

Leu Val Leu Gly Leu Phe Thr Thr Val Leu Thr Leu Phe Phe Ser Ser
                 85                  90                  95

Met Ile Gly Tyr Gly Leu Ala Val Tyr Asp Phe Lys Gly Arg Asn Ile
                100                 105                 110

Ile Phe Val Leu Val Leu Ile Ile Met Met Val Pro Leu Glu Val Met
        115                 120                 125

Met Leu Pro Leu Phe Lys Leu Thr Val Gly Leu His Leu Ile Asp Ser
130                 135                 140

Tyr Thr Gly Val Ile Leu Pro Phe Ile Val Ser Pro Val Ala Val Phe
145                 150                 155                 160

Phe Phe Arg Gln Tyr Ala Leu Gly Leu Pro Arg Asp Leu Leu Asp Ser
                165                 170                 175

Ala Arg Met Asp Gly Cys Thr Glu Phe Gly Ile Phe Phe Arg Ile Met
                180                 185                 190

Ala Pro Leu Met Lys Pro Ala Phe Gly Ala Met Ile Ile Leu Gln Ser
```

```
                    195                 200                 205
Leu Asn Ser Trp Asn Asn Phe Leu Trp Pro Leu Ile Val Leu Arg Ser
        210                 215                 220

Lys Glu Met Phe Thr Leu Pro Ile Gly Leu Ser Ser Leu Leu Ser Pro
225                 230                 235                 240

Tyr Gly Asn Asn Tyr Asp Met Leu Ile Ser Gly Ser Val Phe Ala Ile
            245                 250                 255

Leu Pro Val Ile Ile Ile Phe Leu Phe Phe Gln Lys Tyr Phe Ile Ser
            260                 265                 270

Gly Leu Thr Val Gly Gly Val Lys Gly
            275                 280
```

(2) INFORMATION FOR SEQ ID NO:64:

(i) SEQUENCE CHARACTERISTICS:
        (A) LENGTH: 500 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis (ix) FEATURE:
        (D) OTHER INFORMATION: /product= "abfA"

(xi) SEQUENCE DESCRIPTION: SEQ ID NO:64:

```
Met Lys Lys Ala Arg Met Ile Val Asp Lys Glu Tyr Lys Ile Gly Glu
1               5                   10                  15

Val Asp Lys Arg Ile Tyr Gly Ser Phe Ile Glu His Met Gly Arg Ala
            20                  25                  30

Val Tyr Glu Gly Ile Tyr Glu Pro Asp His Pro Glu Ala Asp Glu Asp
        35                  40                  45

Gly Phe Arg Lys Asp Val Gln Ser Leu Ile Lys Glu Leu Gln Val Pro
    50                  55                  60

Ile Ile Arg Tyr Pro Gly Gly Asn Phe Leu Ser Gly Tyr Asn Trp Glu
65                  70                  75                  80

Asp Gly Val Gly Pro Val Glu Asn Arg Pro Arg Arg Leu Asp Leu Ala
                85                  90                  95

Trp Gln Thr Thr Glu Thr Asn Glu Val Gly Thr Asn Glu Phe Leu Ser
            100                 105                 110

Trp Ala Lys Lys Val Asn Thr Glu Val Asn Met Ala Val Asn Leu Gly
        115                 120                 125

Thr Arg Gly Ile Asp Ala Ala Arg Asn Leu Val Glu Tyr Cys Asn His
    130                 135                 140

Pro Lys Gly Ser Tyr Trp Ser Asp Leu Arg Arg Ser His Gly Tyr Glu
145                 150                 155                 160

Gln Pro Tyr Gly Ile Lys Thr Trp Cys Leu Gly Asn Glu Met Asp Gly
                165                 170                 175

Pro Trp Gln Ile Gly His Lys Thr Ala Asp Glu Tyr Gly Arg Leu Ala
            180                 185                 190

Ala Glu Thr Ala Lys Val Met Lys Trp Val Asp Pro Ser Ile Glu Leu
        195                 200                 205

Val Ala Cys Gly Ser Ser Asn Ser Gly Met Pro Thr Phe Ile Asp Trp
    210                 215                 220

Glu Ala Lys Val Leu Glu His Thr Tyr Glu His Val Asp Tyr Ile Ser
225                 230                 235                 240
```

-continued

```
Leu His Thr Tyr Tyr Gly Asn Arg Asp Asn Asn Leu Pro Asn Tyr Leu
            245                 250                 255

Ala Arg Ser Met Asp Leu Asp His Phe Ile Lys Ser Val Ala Ala Thr
            260                 265                 270

Cys Asp Tyr Val Lys Ala Lys Thr Arg Ser Lys Lys Thr Ile Asn Leu
            275                 280                 285

Ser Leu Asp Glu Trp Asn Val Trp Tyr His Ser Asn Glu Ala Asp Lys
    290                 295                 300

Lys Val Glu Pro Trp Ile Thr Ala Arg Pro Ile Leu Glu Asp Ile Tyr
305                 310                 315                 320

Asn Phe Glu Asp Ala Leu Leu Val Gly Ser Leu Leu Ile Thr Met Leu
            325                 330                 335

Gln His Ala Asp Arg Val Lys Ile Ala Cys Leu Ala Gln Leu Val Asn
            340                 345                 350

Val Ile Ala Pro Ile Met Thr Glu Lys Gly Gly Glu Ala Trp Arg Gln
            355                 360                 365

Pro Ile Phe Tyr Pro Tyr Met His Ala Ser Val Tyr Gly Arg Gly Glu
    370                 375                 380

Ser Leu Lys Pro Leu Ile Ser Ser Pro Lys Tyr Asp Cys Ser Asp Phe
385                 390                 395                 400

Thr Asp Val Pro Tyr Val Asp Ala Ala Val Val Tyr Ser Glu Glu Glu
            405                 410                 415

Glu Thr Leu Thr Ile Phe Ala Val Asn Lys Ala Glu Asp Gln Met Glu
            420                 425                 430

Thr Glu Ile Ser Leu Arg Gly Phe Glu Ser Tyr Gln Ile Ala Glu His
            435                 440                 445

Ile Val Leu Glu His Gln Asp Ile Lys Ala Thr Asn Gln His Asn Arg
    450                 455                 460

Lys Asn Val Val Pro His Ser Asn Gly Ser Ser Ser Val Ser Glu Asn
465                 470                 475                 480

Gly Leu Thr Ala His Phe Thr Pro Leu Ser Trp Asn Val Ile Arg Leu
            485                 490                 495

Lys Lys Gln Ser
            500
```